United States Patent
Ramunas et al.

(10) Patent No.: US 11,872,243 B2
(45) Date of Patent: Jan. 16, 2024

(54) COMPOUNDS, COMPOSITIONS, METHODS, AND KITS RELATING TO TELOMERE EXTENSION

(71) Applicant: THE BOARD OF TRUSTEES OF THE LELAND STANFORD JUNIOR UNIVERSITY, Stanford, CA (US)

(72) Inventors: John Ramunas, Menlo Park, CA (US); Eduard Yakubov, Houston, TX (US); Helen M. Blau, Menlo Park, CA (US); John Cooke, Houston, TX (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 722 days.

(21) Appl. No.: 16/735,683

(22) Filed: Jan. 6, 2020

(65) Prior Publication Data
US 2020/0281959 A1  Sep. 10, 2020

Related U.S. Application Data

(62) Division of application No. 14/187,265, filed on Feb. 22, 2014, now Pat. No. 10,525,075.

(60) Provisional application No. 61/768,047, filed on Feb. 22, 2013.

(51) Int. Cl.
| | |
|---|---|
| *C12N 9/12* | (2006.01) |
| *A61K 31/7088* | (2006.01) |
| *A61K 38/45* | (2006.01) |
| *C12N 15/52* | (2006.01) |

(52) U.S. Cl.
CPC .......... *A61K 31/7088* (2013.01); *A61K 38/45* (2013.01); *C12N 9/1276* (2013.01); *C12N 15/52* (2013.01); *C12Y 207/07049* (2013.01)

(58) Field of Classification Search
CPC .................................................... C12N 9/1276
See application file for complete search history.

(56) References Cited

U.S. PATENT DOCUMENTS

| | | |
|---|---|---|
| 5,583,016 A | 12/1996 | Villeponteau et al. |
| 5,686,306 A | 11/1997 | West et al. |
| 5,770,422 A | 6/1998 | Collins |
| 6,166,178 A | 12/2000 | Cech et al. |
| 6,927,285 B2 | 8/2005 | Cech et al. |
| 7,879,609 B2 | 2/2011 | Morin et al. |
| 7,897,752 B2 | 3/2011 | McSwiggen et al. |
| 8,278,036 B2 | 10/2012 | Kariko et al. |
| 8,323,975 B2 | 12/2012 | Kool |
| 8,497,124 B2 | 7/2013 | Angel et al. |
| 8,802,438 B2 | 8/2014 | Rossi |
| 9,127,248 B2 | 9/2015 | Angel et al. |
| 9,399,761 B2 | 7/2016 | Angel et al. |
| 9,562,218 B2 | 2/2017 | Angel et al. |
| 9,695,401 B2 | 7/2017 | Angel et al. |
| 9,879,228 B2 | 1/2018 | Angel et al. |
| 9,969,983 B2 | 5/2018 | Angel et al. |
| 10,131,882 B2 | 11/2018 | Angel et al. |
| 10,525,075 B2 | 1/2020 | Ramunas et al. |
| 11,007,210 B2 | 5/2021 | Ramunas et al. |
| 2009/0286852 A1 | 11/2009 | Kariko et al. |
| 2009/0286853 A1 | 11/2009 | Gryaznov et al. |
| 2011/0143397 A1 | 6/2011 | Kariko et al. |
| 2012/0046346 A1 | 2/2012 | Rossi et al. |
| 2014/0242154 A1 | 8/2014 | Ramunas et al. |
| 2020/0215095 A1 | 7/2020 | Ramunas et al. |

FOREIGN PATENT DOCUMENTS

| | | |
|---|---|---|
| RU | 2443777 C2 | 2/2012 |
| WO | 2006/008154 A1 | 1/2006 |
| WO | 2007024708 A2 | 3/2007 |
| WO | 2007/041090 A2 | 4/2007 |
| WO | 2009/050483 A1 | 4/2009 |
| WO | 2010/036813 A1 | 4/2010 |
| WO | 2011071931 A2 | 6/2011 |
| WO | 2011130624 A2 | 10/2011 |
| WO | 2012009682 A2 | 1/2012 |
| WO | 2013086008 A1 | 6/2013 |
| WO | 2013090648 A1 | 6/2013 |

OTHER PUBLICATIONS

Bodnar et al. (1998, Science, vol. 279, pp. 349-352) (Year: 1998).*
Kariko et al. (Sep. 2, 2011, Nucleci Acids Res., pp. 1-10) (Year: 2011).*
Xiong et al. (2011, Parmazie, vol. 66, pp. 158-164) (Year: 2011).*
Katzenellenbogen et al. (2010, J. Virology, vol. 84(24), pp. 12934-12944) (Year: 2010).*
Kariko et al. (2012) Molecular Therapy 20:948-93.
Kimura et al. (2010) Nat Protoc. 5:1596-607; doi: 10.1038/nprot.2010.124.
Kormann et al. (2011) Nature Biotechnology 29:154-157.
Lakhal and Wood (2011) Bioessays 33:737-741.
Lansdorp et al. (1996) Hum. Mol. Genet. 5:685-691.
Lawless et al. (2010) Exp Gerontol. 45:772-778.

(Continued)

*Primary Examiner* — Anoop K Singh
*Assistant Examiner* — David A Montanari
(74) *Attorney, Agent, or Firm* — Kilpatrick Townsend & Stockton LLP

(57) ABSTRACT

Compounds and compositions for the transient expression of exogenous telomerase activity in a cell are provided. The compounds and compositions, which relate to a ribonucleic acid coding for a telomerase reverse transcriptase, are useful in the extension of telomeres in cells needing such treatment. Such cells include, for example, cells that contain shortened telomeres and cells from subjects that may benefit from telomere extension, for example subjects that suffer from, or are at risk of suffering from, age-related or other illnesses. Also provided are methods of extending telomeres through the administration of the provided compounds and compositions to animal cells, either in vitro or in vivo, and kits including the compounds or compositions and instructions for use.

28 Claims, 33 Drawing Sheets

Specification includes a Sequence Listing.

(56) References Cited

OTHER PUBLICATIONS

Le et al. (2013) Cell Stem Cell. [published online ahead of print: Nov. 19, 2013]; doi: 10.1016/j.stem.2013.11.005.
Lee et al. (2010) The Journal of Biological Chemistry 285:42033-42045.
Leri et al. (2003) EMBO J. 22:131-139.
Lin and Elledge (2003) Cell 113:881-889.
Lindvall et al. (2003) Cancer Research 63:1743-1747.
Liu et al. (2010) Ageing Research Reviews 9:245-256.
Lopez-Otin et al. (2013) Cell. 153:1194-1217.
Mackenzie et al. (2000) Exp. Cell Res. 259:336-350.
Malone et al. (1989) Proc. Natl Acad. Sci. USA 86:6077-6081.
Martens et al. (1998) Nat. Genet. 18:76-80.
Matsushita et al. (2001) Circ. Res. 89:793-798.
Meyerson et al. (1997) Cell 90:785-795.
Mizrak et al. (2013) Molecular Therapy 21:101-108; doi:10.1038/mt.2012.161.
Mohsin et al. (2012) Journal of the American College of Cardiology doi: 10.1016/j.jacc.2012.04.0474.
Mohsin et al. (2013) Circ Res. 113:1169-1179.
Mourkioti et al. (2013) Nat Cell Biol. 15:895-904.
Nakamura et al. (1997) Science 277:955-959.
Nicholls et al. (2011) Protein Cell 2:726-738.
O"Connor et al. (2004) The Journal of Biological Chemistry 279:28585-28591.
O"Doherty et al. (1994) Immunology 82:487-493.
OSullivan and Karlseder (2010) Nat. Rev. Mol. Cell Biol. 11:171-181.
Park et al. (2007) International Journal of Cancer 120:813-820.
Park et al. (2009) Nature 460:66-72.
Pathology, edited by Qiu Xueshan, Shanghai Scientific Technical Publishers, pp. 9-10, published in Jul. 2011.
Pearce et al. (2008) Oncogene 27:2365-2374.
Perez-Rivero et al. (2006) Circulation 114:309-317.
Perona et al. (2016) INTECH "Telomere—A Complex End of a Chromosome", Ch. 5.
Perrault et al. (2005) Biochemical and Biophysical Research Communications 335:925-936.
Podlevsky and Chen (2012) Mutat. Res. 730:3-11.
Prade-Houdellier et al. (2007) Leukemia 21:2304-2310.
Sacco et al. (2010) Cell 143:1059-1071.
Sahin et al. (2011) Nature. 470:359-365.
Sitte et al. (1998) Free Radic. Biol. Med. 24:885-893.
Smith et al. (2003) Nature Cell Biology 5:474-479.
Steinert et al. (2000) Biochem. Biophys. Res. Commun. 273:1095-1098.
Stern and Bryan (2008) Cytogenetic and Genome Research 122:243-254.
Testa et al. (2011) Diabetic Medicine 28:1388-1394.
Jeda et al. (1997) Cancer Research 57:370-374.
Untergasser et al. (2012) Nucleic Acids Res. 40:e115.
Vaiserman et al. (2016) Ageing Res. Rev. ARR-696.
Van Den Boorn et al. (2011) Nature Biotechnology 29:325-326.
Von Zglinicki et al. (2000) Free Radic. Biol. Med. 28:64-74.
Von Zglinicki et al. (2000) Laboratory Investigation; a Journal of Technical Methods and Pathology 80:1739-1747.
Wang et al. (2012) Cell Res. 22:757-768.
Wentzensen et al. (2011) Cancer Epidemiol. Biomarkers Prev. 20:1238-1250.
Wick et al. (1999) Gene 232:97-106.
Wojtyla et al. (2011) Molecular Biology Reports 38:3339-3349.
Wolff et al. (1990) Science 247:1465-1468.
Wu et al. (2005) Cytotechnology 49:95-107.
Wyatt (2009) "Structure-Function Analysis of the Human Telomerase Reverse Transcriptase" University of Calgary, Ph.D. Thesis (http://dspace.ucalgary.ca/bitstream/1880/47511/1/2009_Wyatt_PhD.pdf).
Xu et al. (1999) Br J Cancer. 80:1156-1161.
Yakubov et al. (2010) Biochem. Biophys. Res. Commun. 394:189-193.
Young et al. (2003) The Journal of Biological Chemistry 278:19904-19908.
Zhu et al. (2007) Aging Cell. 6:515-523.
Zimmermann and Martens (2008) Cell Tissue Res. 331:79-90.
Zvereva et al. (2010) Biochemistry Biokhimiia 75:1563-1583.
Moderna Clinical Study Protocol for mRNA-1273-P301, dated Aug. 20, 2020.
Lu et al. (2012) Oncology Reports 28:1945-1952.
Rubtsova et al. (2012) ACTA Naturae 4:44-61.
Abreu et al. (2010) Molecular and Cellular Biology 30:2971-2982.
Ahmed et al. (2008) J. Cell. Sci. 121:1046-1053.
Ahmed et al. (2017) World J. Exp. Med. 7:1-10.
Akiyama et al. (2011) Leukemia Research 35:416-418.
Allsopp et al. (1992) Proc Natl Acad Sci U S A. 89:10114-10118.
Alter et al. (2009) Blood 113:6549-6557.
Alvarez-Erviti et al. (2011) Nature Biotechnology 29:341-345.
Anti-senescence Theory, edited by Liu Qi, Military Medical Science Press, pp. 19-20, published on Oct. 31, 2006.
Armanios (2009) Ann. Rev. Genomics Hum. Genet. 10: 45-61.
Artandi Depinho (2010) Carcinogenesis 31:9-18.
Aubert et al. (2012) Mutat. Res. 730:59-67.
Autexier and Lue (2006) Annu Rev Biochem. 75:493-517.
Bagheri et al. (2006) Proc. Natl Acad. Sci. U.S.A. 103:11306-11311.
Bar and Blasco (2016) F1000Res. Faculty Rev-89.
Beitzinger et al. (2006) Oncogene 25:813-826.
Binet et al. (2009) Cancer Res. 69:9183-9191.
Blackburn et al. (2011) Cancer Prevention Research 4:473-475.
Blasco et al. (1997) Cell 91:25-34.
Britt-Compton et al. (2009) FEBS Lett. 583:3076-3080.
Brouilette et al. (2003) Arteriosclerosis, Thrombosis, and Vascular Biology 23:842-846.
Buchner et al. (2010) Antioxidants Redox Signaling 13:551-558.
Calado et al. (2012) Leukemia 26:700-707.
Cawthon (2002) Nucleic Acids Res. 30(10):e47.
Cawthon (2009) Nucleic Acids Res. 37(3):e21.
Chawla et al. (2011) The EMBO Journal 30:4047-4058.
Cifuentes-Rojas and Shippen (2011) Mutat. Res. 730:20-27; doi:10.1016/j.mrfmmm.2011.10.003.
Cong et al. (2002) Microbiology and Molecular Biology Reviews 66:407-425.
Counter et al. (1998) Proc Natl Acad Sci U S A. 95:14723-14728.
Cristofalo and Kritchevsky (1969) Med Exp Int J Exp Med. 19:313-320.
Cristofalo et al. (2004) Mech Ageing Dev. 125:827-848.
Di Mitri et al. (2011) Journal of Immunology 187:2093-2100.
Dimri et al. (1995) Proc Natl Acad Sci U S A. 92:9363-9367.
Ding et al. (2012) Cell 148:896-907.
Fath et al. (2011) PLoS One 6:3.
Galliot et al. (2017) Development 144:357-364.
Gilbert et al. (2010) Science. 329:1078-1081.
Gladych et al. (2011) Biochemistry and Cell Biology 89:359-376.
Glezer et al. (2006) FASEB J. 10.1096/fj.05-5234fje.
Greber et al. (2011) EMBO J. 30:4874-4884.
Haendeler et al. (2003) FEBS Letters 536:180-186.
Hajj and Whitehead (2017) Nature Rev. 2:17056.
Harley et al. (2011) Rejuvenation Res. 14:45-56.
Hayflick and Moorhead (1961) Exp Cell Res. 25:585-621.
Holt et al. (1997) Proc Natl Acad Sci U S A. 94:10687-10692.
Hooijberg (2000) J. Immunol. 165:4239-4245.
Imuro et al. (2007) J. Gastroent. Hepatol. 22:S57-S58.
Manishi et al. (2005) Journal of Hypertension 23:1699-1706.
Jaskelioff (2011) Nature 469:102-107.
Jirikowski et al. (1992) Science 255:996-998.
Kabnick and Housman (1988) Mol Cell Biol. 8:3244-3250.
Banks et al. (1997) JAMA 278:1345.
Neinrich et al. (1997) Nature Genetics 17:498.
Bodnar et al. (1998) Science 279:349.
Nen et al. (1998) Human Mol. Gen. 7:1137.
Liu et al. (1999) Proc. Nat'l Acad. Sci. USA 96:5147.
Takubo et al. (1999) Age 22:95.
Nair et al. (2000) Nature Med. 6:1011.
Hiyama et al. (2001) Neoplasia 3:17.
Yi et al. (2001) Nucleic Acids Res. 29:4818.

(56) References Cited

OTHER PUBLICATIONS

Sæbøe-Larssen et al. (2002) J. Immunolog. Meth. 259:191.
Shin et al. (2004) Clin. Cancer Res. 10:2551.
Kariko et al. (2005) Immunity 23:165.
Su et al. (2005) J. Immunol. 174:3798.
Wu et al. (2006) Journal of Cell Science 119:13.
Hiatakeyama et al. (2008) Mechanisms of Ageing and Development 129:9.
Kariko et al. (2008) Mol. Ther. 16:1833.
Katzenellenbogen et al. (2010) J. Virology 84:12934.
Takubo et al. (2010) Geriatr. Gerontol. Int. 2010 10:S197.
Warren et al. (2010) Cell Stem Cell 7:618.
Harley et al. (2011) Rejuvenation Res. 14:45.
Kariko et al. (2011) Nucleic Acids Res. 2011:1.
Steczkiewicz et al. (2011) Proc. Nat'l Acad. Sci. USA 108:9443.
Suso et al. (2011) Cancer Immunol. Immunother. 60:809.
Van Den Boorn et al. (2011) Nature Biotechnol. 29:325.
Xiong et al. (2011) Pharmazie 66:158.
Arnold et al. (2012) ISRN Cell Biol. 2012:124878.
Boccardi et al. (2012) EMBO Mol. Med. 4 685-687.
Cao et al. (2012) Oncogene 21:3130.
Dashinimaev et al. (2012) Molekulyaraya Meditsina 6 46-51.
Dashinimaev et al. (2012) Molekulyaraya Meditsina 6 46-51 (machine translation into English).
Fossel (2012) Curr. Tran. Geriatr. Gerontol. Rep. 1:121.
Mizrak et al. (2012) Mol. Ther. 21:101.
Wang et al. (2012) Methods in Molecular Biology 969 221-233.
Zhong et al. (2012) Cell 150 481-494.
Kannan et al. (2013) Stem Cell Reports 1:28.
Mandal et al. (2013) Nature Protocols 8 568-582.
Extended European Search Report dated Nov. 22, 2016 for related European Patent Application No. 14754545.3 (PCT/US2014/017867).
Ramunas et al. (2015) FASEB Journal 29:1930.
Bernardes De Jesus et al. (2012) EMBO Mol. Med. 4 691-704.
Calado et al. (2009) Proc. Nat'l Acad. Sci. USA 106 1187-1192.
Fossel (1998) JAMA 279:1732.
Greider (1990) BioEssays 12:363.
McIvor (2011) Mol. Ther. 19:822.
Arya, S. et al., "Strong Immune Responses Induced by Direct Local Injections of Modified mRNA-Lipid Nanocomplexes," Molecular Therapy Nucleic Acids, 19:1098-1109, 2020.
Billström, G. et al., "A Surprisingly Poor Correlation between In Vitro and In Vivo Testing of Biomaterials for Bone Regeneration: Results of a Multicentre Analysis," European Cells and Materials, 31:312-322, 2016.
Chien, K. et al., "Synthetic Chemically Modified mRNA (modRNA): Toward a New Technology Platform for Cardiovascular Biology and Medicine," Cold Spring Harb Perspect Med, 5:a014035, 9 pages, 2015.
Fight Aging!, "Can Cellular Senescence be Reversed in the Near Future, and is Reversal Desirable?" published online at <https://www.fightaging.org/archives/2016/12/can-cellular-senescence-be-reversed-in-the-near-future-and-is-reversal-desirable/>, 4 pages, Dec. 13, 2016.
Nazari-Shafti, T. and J. Cooke, "Telomerase Therapy to Reverse Cardiovascular Senescence," Methodist Debakey Cardiovasc J., 11(3):172-175, 2015.
Rezaee, R. and M. Abdollahi, "The Importance of Translatability in Drug Discovery," Expert Opinion on Drug Discovery, 12(3):237-239, 2017.
Verywell Health, "What does in vivo and in vitro mean, definition, similarities and differences," published online at <https://www.verywellhealth.com/what-does-in-vivo-and-in-vitro-mean-2249118?print>, 4 pages, Nov. 18, 2019.

\* cited by examiner

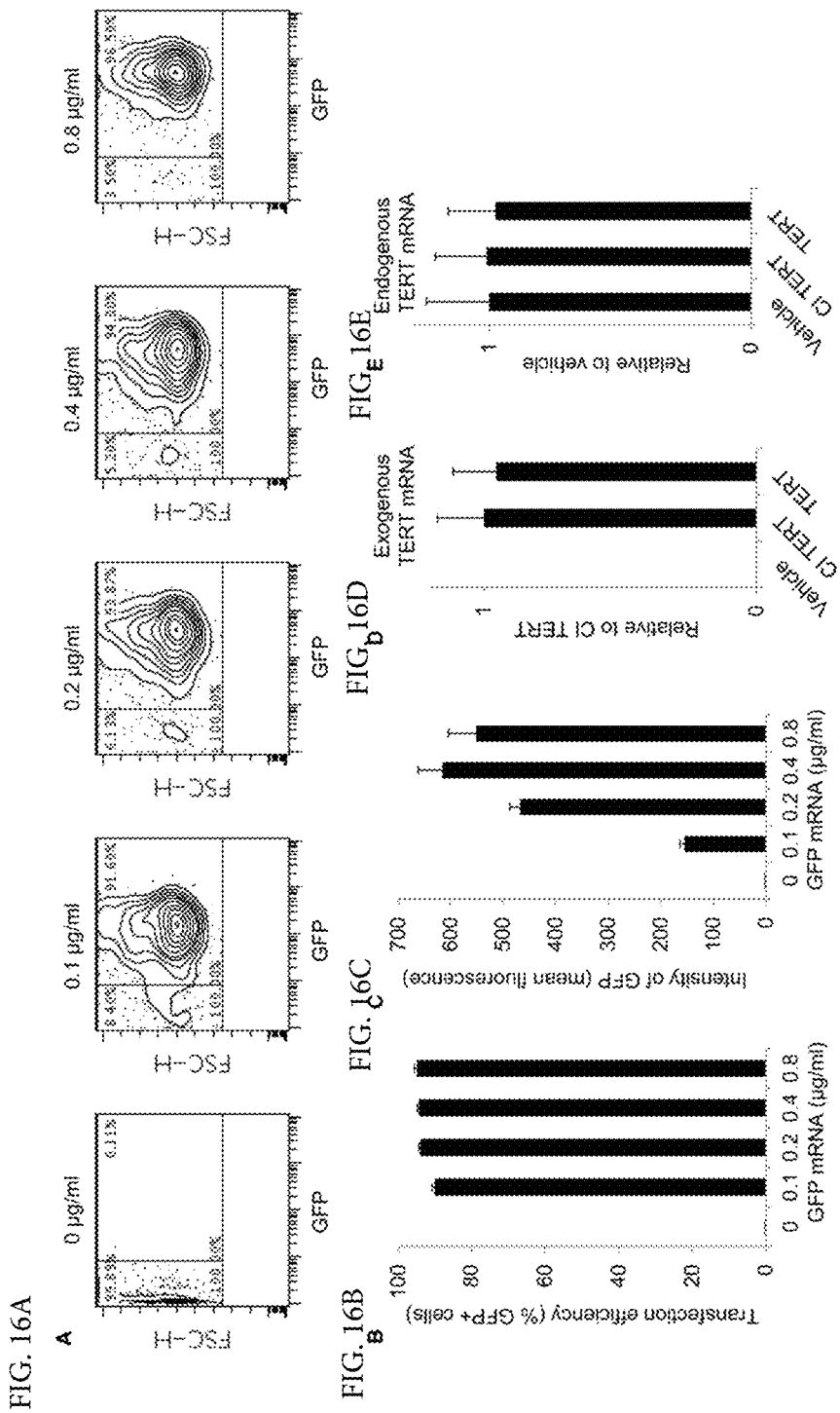

FIG. 20
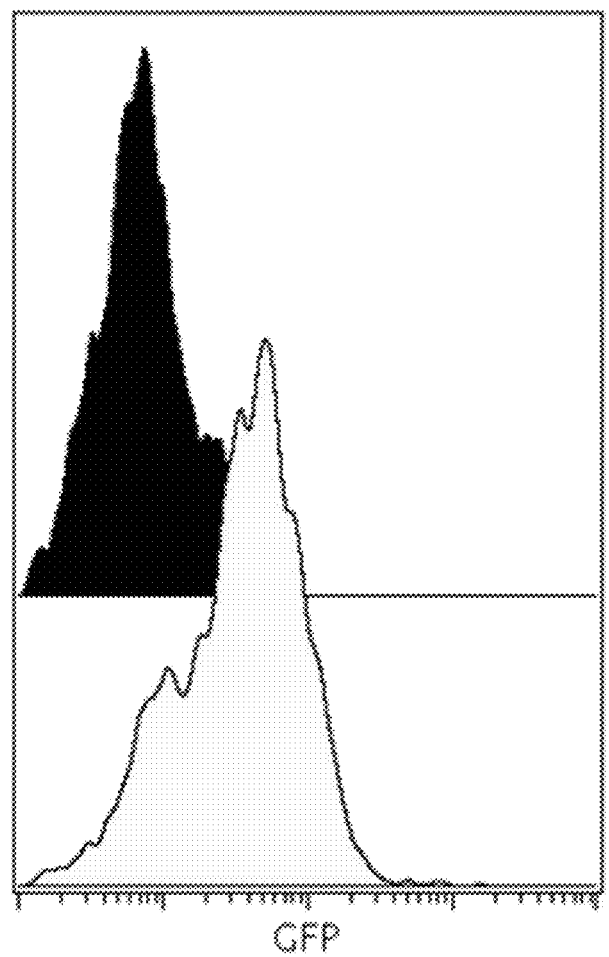
10.36  31.26  52.16
Calculated Raw
values of Means
using X-Axis
channel(s): GFP
GFP - Panel 1
| 0 | 10.36 |
|---|---|
| 1 | 52.16 |

COMPOUNDS, COMPOSITIONS, METHODS, AND KITS RELATING TO TELOMERE EXTENSION

CROSS-REFERENCE TO RELATED APPLICATIONS

This application is a divisional of U.S. patent application Ser. No. 14/187,265, filed on Feb. 22, 2014, which claims the benefit of U.S. Provisional Application No. 61/768,047, filed on Feb. 22, 2013, the disclosures of which are incorporated herein by reference in their entireties.

STATEMENT OF GOVERNMENT SUPPORT

This invention was made with government support under contract AR063963 awarded by the National Institutes of Health. The government has certain rights in the invention.

SEQUENCE LISTING

This application includes a Sequence Listing, as set forth in an ASCII-compliant text file named "S12-001U04_ST25.txt", created on Jan. 6, 2020, and containing 2,179 bytes, which is incorporated herein by reference in its entirety.

BACKGROUND OF THE INVENTION

Telomeres comprise repetitive DNA sequences at the ends of linear chromosomes that, when sufficiently long, allow each chromosome end to form a loop that protects the ends from acting as double-stranded or single-stranded DNA breaks. Artandi & DePinho (2010) Carcinogenesis 31:9-18. Telomeres shorten over time, due in part to oxidative damage and incomplete DNA replication, eventually leading to critically short telomeres unable to form the protective loop, exposure of the chromosome ends, chromosome-chromosome fusions, DNA damage responses, and cellular senescence, apoptosis, or malignancy. O'Sullivan and Karlseder (2010) Nat. Rev. Mol. Cell Biol. 11:171-181; Calado et al. (2012) Leukemia 26:700-707; Artandi and DePinho (2010) Carcinogenesis 31:9-18.

The enzyme complex telomerase extends telomeres and comprises two essential components: the telomerase reverse transcriptase (TERT), and an RNA component known as telomerase RNA component (TERC). Other components of the telomerase complex include the proteins TCAB1, Dyskerin, Gar1, Nhp2, Nop10, and RHAU. Brouilette et al. (2003) Arteriosclerosis, Thrombosis, and Vascular Biology 23:842-846. TERT is a limiting component of the telomerase complex, and thus treatments that increase TERT can increase telomerase activity. Telomerase activity is typically measured using the telomeric repeat amplification protocol (TRAP) assay, which quantifies the ability of a cell lysate or other sample to extend a synthetic telomere-like DNA sequence.

As would be expected due to the importance of telomere length maintenance in preventing cellular senescence and apoptosis and resulting cellular dysfunction, genetic mutations of TERT and TERC are linked to fatal inherited diseases of inadequate telomere maintenance, including forms of idiopathic pulmonary fibrosis, dyskeratosis congenita, and aplastic anemia. The effects of premature cellular senescence and apoptosis due to short telomeres in these diseases are devastating in themselves, and may be compounded by increased risk of cancer. Artandi and DePinho (2010) Carcinogenesis 31:9-18; Alter et al. (2009) Blood 113:6549-6557. In addition to abundant correlative data linking short telomeres to cancer (Wentzensen et al. (2011) Cancer Epidemiol. Biomarkers Prev. 20:1238-1250), aplastic anemia provides some of the first direct evidence that critically short telomeres and resulting chromosomal instability predispose cells to malignant transformation in humans (Calado et al. (2012) Leukemia 26:700-707). There is evidence that short telomeres make the difference between fatal and non-fatal muscular dystrophy (Sacco et al. (2010) Cell 143:1059-1071), and that telomere extension averts endothelial cell senescence (Matsushita et al. (2001) Circ. Res. 89:793-798), which is associated with atherosclerosis, hypertension, and heart disease (Pérez-Rivero et al. (2006) Circulation 114:309-317). In addition to being implicated in these and other diseases, short telomeres also limit cell amplification for cell therapies and bioengineering applications. Mohsin et al. (2012) Journal of the American College of Cardiology doi:10.1016/j.jacc.2012.04.0474.

A natural product-derived telomerase activator, TA-65®, has been sold commercially as a nutraceutical by T.A. Sciences, Inc. Harley et al. (2011) Rejuvenation Research 14:45-56. This compound purportedly turns on the endogenous hTERT gene, thus activating expression of native telomerase. It is not clear, however, how this treatment overcomes the normal regulation of the native telomerase activity.

Human cells with little or no telomerase activity have been transfected with vectors encoding human TERT (hTERT). See, e.g., Bodnar et al. (1998) Science 279:349-352. The transfected cells were found to express telomerase, to display elongated telomeres, to divide vigorously, and to display reduced senescence compared to cells lacking telomerase, but the genomic modification resulting from this treatment increases the risk and limits the utility of the approach.

A limited capacity to replicate is one of the defining characteristics of most normal cells. An end-point of this limited replicative process is senescence, an arrested state in which the cell remains viable but no longer divides. Senescent cells are often characterized by an altered pattern of gene expression, altered morphology, and reduced or abrogated ability to perform their normal functions.

The shortening of telomeres plays a direct role in cellular senescence in animal tissues during aging. Furthermore, there is accumulating evidence implicating short telomeres in a variety of diseases, including those described above. The prospect of preventing disease by telomere extension motivates a need for safe and effective treatments to extend telomeres in animal cells in vivo and/or in vitro. Further, there is a need to safely and rapidly extend telomeres in cells for use in cell therapy, cell and tissue engineering, and regenerative medicine.

At the same time, however, there is a danger in the constitutive activation of telomerase activity. Indeed for cell therapy applications, avoiding the risk of cell immortalization is of paramount importance. To this end, transient, rather than constitutive, telomerase activity may be advantageous for safety, especially if the elevated telomerase activity is not only brief but extends telomeres rapidly enough that the treatment does not need to be repeated continuously. Current methods of extending telomeres include viral delivery of TERT under an inducible promoter, delivery of TERT using vectors based on adenovirus and adeno-associated virus, and small molecule activators of telomerase. These methods risk either insertional mutagenesis, continual elevation of telomerase activity, or both.

Thus, there is strong motivation to develop a therapy that safely extends telomeres to potentially prevent, delay, ameliorate, or treat these and other conditions and diseases, to do the same for the gradual decline in physical form and function and mental function that accompanies chronological aging, and to enable cell therapies and regenerative medicine. Such a therapy would be of great use in the rejuvenation of all animals, including humans, pets, livestock, zoo animals, and animals of endangered species.

SUMMARY OF THE INVENTION

The present invention addresses these and other problems by providing an alternative that offers the benefits of a highly transient increase in telomerase activity, combined with rapid telomere extension so that the treatment does not need to be continuous or even frequent, and with no risk of genomic insertional mutagenesis. Specifically, the invention provides compositions, methods, and kits for the extension of telomeres by the transient translation of exogenous telomerase activity in a cell.

In one aspect, the invention provides compounds for the extension of telomeres comprising:
 a synthetic ribonucleic acid comprising at least one modified nucleoside and coding for a telomerase reverse transcriptase;
 wherein telomeres are extended within a cell treated with the compound.

In some embodiments, the telomerase reverse transcriptase is a mammalian, avian, reptilian, or fish telomerase reverse transcriptase or a variant that retains telomerase catalytic activity, and in specific embodiments is a human telomerase reverse transcriptase.

In some embodiments, the ribonucleic acid comprises a 5' cap, a 5' untranslated region, a 3' untranslated region, and a poly-A tail. The 5' cap may be non-immunogenic and the 5' cap may have been treated with phosphatase.

In preferred embodiments, the poly-A tail increases stability of the ribonucleic acid.

In other preferred embodiments, the 5' untranslated region or the 3' untranslated region comprise a sequence from a stable mRNA or an mRNA that is efficiently translated, or they both comprise a sequence from a stable mRNA or an mRNA that is efficiently translated.

In still other preferred embodiments, the 5' cap, the 5' untranslated region, or the 3' untranslated region stabilizes the ribonucleic acid, increases the rate of translation of the ribonucleic acid, or modulates the immunogenicity of the ribonucleic acid.

In highly preferred embodiments, the at least one modified nucleoside modulates immunogenicity of the ribonucleic acid.

In some embodiments, the ribonucleic acid is a purified synthetic ribonucleic acid.

In preferred embodiments, the synthetic ribonucleic acid is purified to remove immunogenic components.

In certain specific embodiments, the ribonucleic acid codes for a human, cat, dog, mouse, horse, cow, sheep, pig, African elephant, chicken, rat, zebrafish, Japanese medaka, or chimpanzee telomerase reverse transcriptase, or a polypeptide with at least 95% sequence identity to the telomerase reverse transcriptase.

In another aspect, the invention provides compositions comprising a compound of the invention and a telomerase RNA component, which, in some embodiments, is a mammalian, avian, reptilian, or fish telomerase RNA component. In more specific embodiments, the telomerase RNA component is a human telomerase RNA component. In some embodiments, the compounds and compositions of the invention further comprise a delivery vehicle.

In some embodiments, the delivery vehicle is an exosome, a lipid nanoparticle, a polymeric nanoparticle, a natural or artificial lipoprotein particle, a cationic lipid, a protein, a protein-nucleic acid complex, a liposome, a virosome, or a polymer. In specific embodiments, the delivery vehicle is a cationic lipid.

In preferred embodiments, the delivery vehicle is non-immunogenic. In other preferred embodiments, the delivery vehicle is partly immunogenic. In particular, under some circumstances, it may be desirable for the vehicle to retain some immunogenicity.

According to another aspect of the invention, methods of extending telomeres are provided, comprising the step of administering any of the disclosed compounds or compositions to an animal cell, wherein at least one telomere is extended within the cell.

In some method embodiments, the cell has at least one shortened telomere prior to the administering step.

In some embodiments, the cell is from or in a subject suffering from or at risk of an age-related illness, an age-related condition, or an age-related decline in function or appearance.

In some embodiments, the cell is from or in a subject suffering from or at risk of cancer, heart disease, stroke, diabetes, diabetic ulcers, Alzheimer's disease, osteoporosis, a decline in physical ability or appearance, physical trauma or chronic physical stress, psychological trauma or chronic psychological stress, reduced immune function, immunosenescence, or macular degeneration.

In some embodiments, the cell is a somatic cell of endodermal, mesodermal, or ectodermal lineage, or a germ line or embryonic cell.

In some embodiments, the cell is an induced pluripotent stem cell or a cell used to produce an induced pluripotent stem cell.

In some embodiments, the cell is a transdifferentiated cell or a cell used to produce a transdifferentiated cell.

In some embodiments, the cell is an isolated cell, and the administering step lasts no longer than 48 hours. In other embodiments, the cell is an isolated cell, and the administering step lasts at least 2 hours.

In some embodiments, the cell is an isolated cell, and the administering step is performed no more than four times. In other embodiments, the cell is an isolated cell, and the administering step is performed at least two times.

In some embodiments, the cell is an isolated cell, and the method further comprises the step of measuring telomerase activity in the cell. In specific embodiments, the administering step increases telomerase activity in the cell, and in even more specific embodiments, the telomerase activity is transiently increased by at least 5%. In other specific embodiments, the half-life of increased telomerase activity is no longer than 48 hours.

In some embodiments, the method further comprises the step of measuring telomere length in the cell. In specific embodiments, average telomere length is increased by at least 0.1 kb.

In some embodiments, the cell is an isolated cell, and the method further comprises the step of measuring population doubling capacity in the cell. In specific embodiments, the population doubling capacity increases, in some cases by at least one population doubling.

In preferred embodiments, the cell is from or in a mammalian subject, and in even more preferred embodiments, the cell is from or in a human subject.

In some embodiments, the cell is an isolated cell, and in other embodiments, the cell is not an isolated cell. In some embodiments, the administering step comprises electroporation. In some embodiments, the at least one telomere is transiently extended within the cell.

According to yet another aspect of the invention, kits for extending telomeres in an animal cell are provided, the kits comprising any of the above compounds or compositions and instructions for using the compound or composition to extend telomeres.

In some embodiments, the kits further comprise packaging materials. In some specific embodiments, the packaging materials are air-tight. In some specific embodiments, the packaging materials comprise a metal foil container.

In some embodiments, the kits further comprise a desiccant, a culture medium, or an RNase inhibitor.

In some embodiments, the composition is sterile. In some embodiments, the kit comprises a compound of the invention, instructions for using the composition to extend telomeres, and a telomerase RNA component, a delivery vehicle, or both a telomerase RNA component and a delivery vehicle.

In yet another aspect, the invention provides methods of treatment, comprising administering a compound or composition of the invention to an animal subject in need of, or that may benefit from, telomere extension. In some embodiments, the animal subject suffers from or is at risk of a disease or condition resulting from shortened telomeres.

BRIEF DESCRIPTION OF THE DRAWINGS

FIG. 1A: Schematic of the modRNA construct and approach used in these studies. The modRNA construct encodes human TERT and has 5' and 3' UTRs that confer stability, such as from β-globin mRNA. CI TERT has a single bp mutation. FIG. 1B: Transfection of TERT or CI TERT modRNA results in increased exogenous TERT modRNA levels in treated cells, but not untreated controls, above endogenous TERT RNA levels. FIG. 1C: Levels of protein recognized by anti-TERT antibody are significantly higher in MRC-5 cells 24 hours after transfection with modRNA encoding TERT or CI TERT (P<0.03 or 0.01, respectively) than in untreated or vehicle-only cells. FIG. 1D: Treatment with modRNA encoding TERT, but not CI TERT, causes transient increase in telomerase activity in MRC-5 cells.

FIG. 4A: Treatment and assay schedule used in these studies. Treatments lasted 5 hours. FIG. 4B: Image of TRF Southern blot (inset) and its quantification in which the chemoluminescent signal was normalized to account for the number of probes per unit of telomere length, and the average intensity of each pixel row in each gel lane was then plotted relative to telomere length (n=3 biological replicates for each treatment). FIG. 4C: Averages of telomere length distributions in FIG. 4B, revealing that telomeres in cells treated with TERT modRNA are significantly (P<0.014) longer than in untreated or vehicle only-treated controls. FIG. 4D: Proportion of telomeres longer than an arbitrary threshold (4.2 kb) is greater in cells treated with TERT modRNA than in untreated and vehicle only-treated controls. FIG. 4E: Representative fluorescence micrograph of metaphase spread of MRC-5 fibroblasts used in quantitative in situ hybridization (Q-FISH) to compare telomere lengths, showing telomere probe (light, punctate) and DNA (smooth shading). FIG. 4F: Quantification of Q-FISH measurements of telomere length in treated and control cells (n=15 cells for each of two biological replicates for each treatment), showing rapid telomere extension in treated cells. (Note that TRF measures the length of both telomeric and subtelomeric DNA, whereas Q-FISH measures only telomeric DNA, thus explaining the differences between the Q-FISH and TRF results.) FIG. 4G: (i) Standard curve relating cumulative population doublings of MRC-5 cells following receipt from the supplier to telomere length as measured using Q-FISH to quantify average total telomere probe fluorescence per cell, which is linearly proportional to telomere length. (ii) Quantification of average telomere length per cell in MRC-5 cells treated three times with TERT modRNA at 48 hour intervals, as measured using Q-FISH.

FIG. 5A: Growth curves of cells treated with TERT modRNA once, twice, or three times, or three times followed by an additional treatment 8 weeks after the first treatment. Controls comprise either no treatment, or treatment with vehicle only or CI TERT four times. (n=3 for each treatment). FIG. 5B: Growth curves of cells treated with TERT modRNA and TERC RNA in a 1:5 molar ratio (n=3). FIG. 5C: Treatment once, twice, or three times with TERT modRNA confers additional replicative capacity to MRC-5 cells beyond that of untreated cells, in a dose-dependent manner. The incremental increase in proliferative capacity conferred by the second and third treatments, delivered at 48 hours after the first treatment, is not as great as the increase in proliferative capacity conferred by the first treatment; however, an additional fourth treatment several weeks after the first three treatments confers as much additional proliferative capacity as did the first treatment, indicating that the timing of the treatments is important for optimizing the amount of proliferative capacity conferred by the treatment. Treatment three times with TERT modRNA and TERC modRNA together in a 1:5 molar ratio confers greater proliferative capacity than treatment three times with TERT modRNA alone. Treatment with vehicle only or CI TERT modRNA confers no additional replicative capacity. (n=3).

FIG. 6A: Percentage of cells with fluorescence more than two SD above the mean of untreated cells (n=10000). FIG. 6B: Mean fluorescence (n=10000). FIG. 6C: Fluorescence micrograph of nGFP in transfected MRC-5 cells, counterstained with DAPI.

FIG. 8A: MRC-5 cells in early passages (left) are several times smaller area than cells in later passages (right), as shown in typical micrographs of PD 2 and PD 53 untreated cells as seen on a hemocytometer. FIG. 8B: Early (PD 2) and mid (PD 35) passage MRC-5 cells exhibit little swelling, defined as having a diameter greater than 25 microns as measured visually on a hemocytometer (where one small square is 50 microns across), whereas a significantly greater fraction of late passage (PD 53) cells are swollen. In contrast, PD 53 cells that had been treated with TERT modRNA, but not those treated with CI TERT modRNA, at PD 40 exhibit little swelling.

FIG. 13A: Schematic of modified mRNA comprising the coding sequence of the full length functional form of TERT or a catalytically-inactive (CI) form of TERT, flanked by untranslated regions (UTRs) of HBB and a 151 nt poly-A tail, synthesized using modified nucleotides pseudouridine and 5-methylcytidine. FIG. 13B: Transfection efficiency of myoblasts (n=2,000) treated with 0.8 µg/ml modified mRNA encoding GFP measured by flow cytometry 24 h post-transfection exceeded 95% (additional plots in FIG. 16A). FIG. 13C: Total TERT protein levels were measured by quantitative Western blot (panel C, left; FIG. 13D: Detection of telomerase activity in fibroblasts and myoblasts transfected with 1 µg/ml modified TERT mRNA, as measured using the telomere repeat amplification protocol (TRAP). Arrow indicates internal controls for PCR efficiency.

FIG. 14A: Mean telomere lengths in untreated fibroblasts decreased over time in culture as measured by MMqPCR and by SpectraCell (correlation coefficient 0.97, P<0.001). Experiment was repeated twice with four technical replicates each. FIG. 14B: Mean telomere lengths in fibroblasts transfected with 1 µl TERT modRNA, CI TERT mRNA, or vehicle only, once, twice, or three times in succession at 48 h intervals. Experiment was repeated twice with four technical replicates each. P<0.01, *P<0.001 compared to vehicle only-treated cells. FIG. 14C: Mean telomere lengths in myoblasts treated as in FIG. 14B. Experiment was repeated twice with four technical replicates each. ***P<0.001 compared to vehicle only-treated cells. FIG. 14D: Growth curves of fibroblasts treated as in FIG. 14B, with green arrows indicating treatments times. Growth curves were repeated twice with each population cultured in triplicate. Replicative capacity increased in a dose-dependent manner (right panel). *P<0.05, **P<0.01 compared to vehicle only-treated cells. FIG. 14E: Proliferation capacity of myoblasts, treated as in FIG. 14B (green arrows). Growth curves were repeated twice, with each population cultured in triplicate. All data are presented as means±s.e.m.

FIG. 15A: Quantification of β-gal-expressing fibroblasts after modified TERT mRNA transfection three times in succession at 48 h intervals (green arrows). The control cells, comprising untreated, vehicle only, and CI TERT mRNA-treated populations, stopped expanding at PD 53, and the TERT modRNA-treated population stopped expanding at PD 80. Each experiment was conducted twice with >50 cells per sample scored manually. Representative images show β-gal-stained TERT modRNA-treated fibroblasts at PD 53 (top) and PD 80 (bottom). Scale bar length is 200 microns. FIG. 15B: Quantification of β-gal expression in myoblasts treated as in FIG. 15A. Controls are as in FIG. 15A. The control and TERT modRNA-treated populations stopped expanding at PD 8 and PD 11, respectively. Each experiment was conducted twice, with >50 cells per sample scored manually. Representative images show myoblasts at PD 2 (top) and TERT modRNA-treated myoblasts at PD 11 (bottom). FIG. 15C Quantification of enlarged cells associated with replicative senescence in fibroblasts transfected three times with modified TERT mRNA. Population plateaus are as in FIG. 15A. Controls are vehicle only and CI TERT mRNA-treated. Each experiment was conducted twice, with >50 cells per sample scored manually. Representative images show untreated fibroblasts at PD 2 (top) and PD 53 (bottom). All data are presented as means±s.e.m. Scale bar length is 200 microns.

FIGS. 16A-16E. High efficiency transfection of modified mRNA into human myoblasts. FIGS. 16A and 16B: Quantification of GFP fluorescent myoblasts (n=2000) transfected with 0.1-0.8 µg/ml of modified mRNA encoding GFP as measured by flow cytometry 24 h after start of treatment. FIG. 16C: Mean fluorescence of modified GFP mRNA-transfected myoblasts in response to increasing doses. FIG. 16D: Quantification of exogenous TERT modRNA in fibroblasts 24 h after transfection with 1 µg/ml of TERT or CI TERT modRNA, as measured using RT-qPCR. Ratio of TERT to CI TERT was calculated using the Pfaffl method with RPL37A and GAPDH as reference genes (n=3). FIG. 16E: Quantification of endogenous TERT modRNA in fibroblasts 24 h after transfection with 1 µg/ml of TERT or CI TERT modRNA, as measured using qPCR, calculated as in FIG. 16D. All data are presented as means±s.e.m.

FIG. 17. Expression of TERT after modified mRNA delivery. TERT protein expression in fibroblasts harvested 24 h after start of treatment with 1 µg/ml TERT modRNA was measured by multiplexed infrared Western blot. The serial dilution of total protein was used to generate a standard curve to compare relative amounts of TERT protein to controls. The specificity of the TERT antibody used here has been extensively tested (Wu, 2006).

FIG. 20. Electroporation of GFP modRNA into human leukocytes (mononuclear cells) results in high transfection efficiency.

DETAILED DESCRIPTION OF THE INVENTION

Figure 1A:
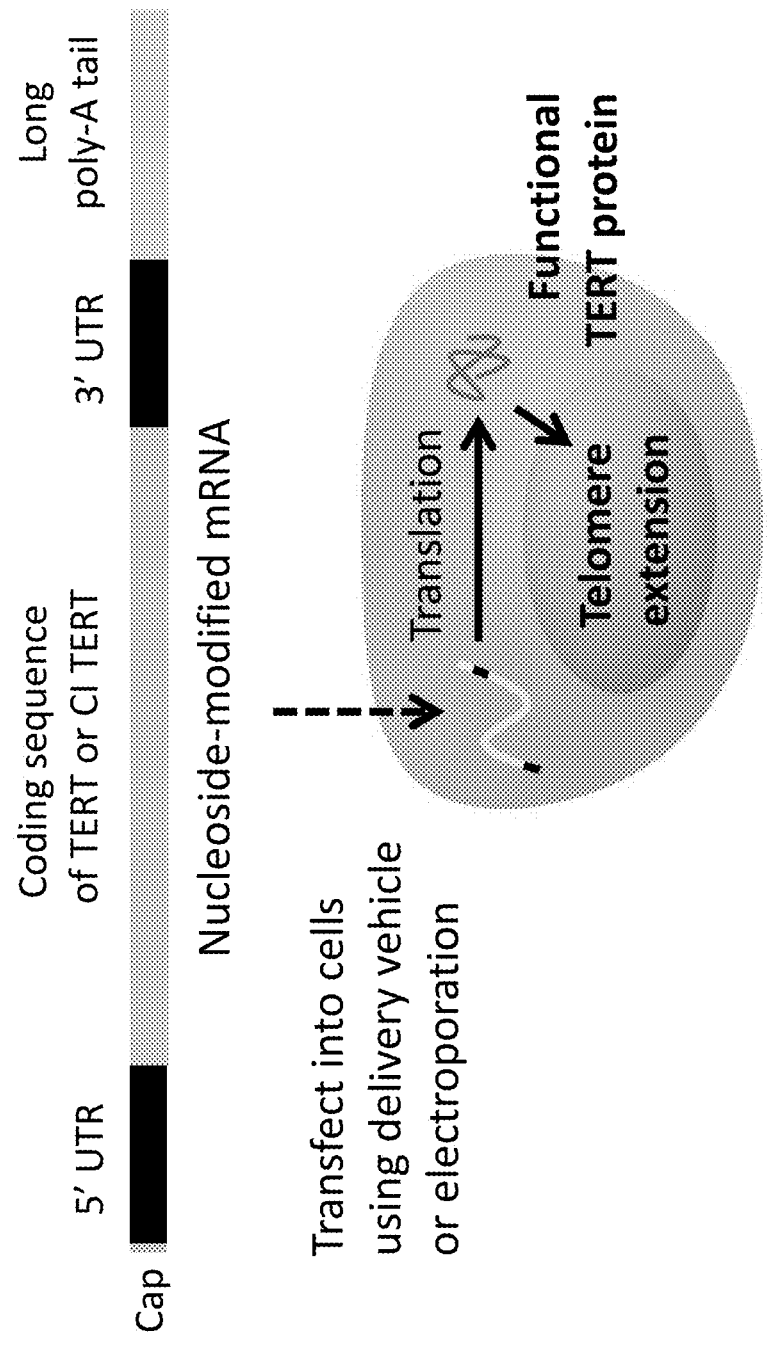
FIGS. 1A-1D. Transfection of MRC-5 cells with a modified ribonucleic acid (modRNA) encoding TERT, but not catalytically-inactive TERT (CI TERT), transiently increases telomerase activity.

Telomeres are DNA sequences at the ends of chromosomes that protect the ends of the chromosomes but that shorten over time. Critically short telomeres may cause cells to stop functioning correctly or to die. Critically short telomeres may also lead to chromosome fusions that may in turn lead to cancer. Even in the absence of a specific diagnosed disease, short telomeres are implicated in the gradual decline in function of the mind and body and in the appearance of aging.

At the same time, however, telomere shortening can play a protective role against cancer, for example in the situation where a cell acquires a mutation that causes it to profilerate faster than normal cells. In that situation, telomere shortening prevents the cell from proliferating indefinitely and causing cancer. It is therefore not necessarily beneficial to extend telomeres continually.

In mammals, telomeres comprise tandem repeats of the sequence TTAGGG, and in other animals such as birds, reptiles, and fish, the repeated sequence varies. In all of these types of animals, the telomeres are double stranded for many kilobases (kb). Average telomere lengths differ between species as shown in Table 1.

TABLE 1

Average telomere length in adult fibroblasts of different species

| Species | Average telomere length (kb) |
| --- | --- |
| Cow | 18 |
| Sheep | 18 |
| Pig | 15 |
| Horse | 14 |
| Dog | 15 |
| Panda | 25 |
| Tiger | 50 |
| House mouse | 40 |
| Sonoran deer mouse | 9 |
| Norway rat | 40 |
| Naked mole rat | 16 |
| European white rabbit | 50 |
| Black-tailed jack rabbit | 25 |
| Spider monkey | 7 |
| Squirrel monkey | 9 |
| Rhesus monkey | 16 |
| Orangutang | 10 |
| Bonobo | 10 |
| Human | 9 |
| Indian elephant | 15 |
| African elephant | 14 |
| Cat | 11 |

In humans, telomeres start out before birth with lengths of 15-20 kb, and at birth with lengths of 12-15 kb. Telomeres shorten rapidly during childhood, and then by about 0-100 bp per year on average in adulthood, a rate which varies depending on the cell type, exposure to psychological or oxidative stress, and other factors.

Telomeres are part of the telomere complex, which protects the ends of chromosomes. The telomere complex also comprises a set of proteins collectively called Shelterin. Telomere complex proteins include POT1, TPP1, ATM, DAT, TRF1, TRF2, Rap1, Rif1, TIN2, NBS, MRE17, and RAD50 and their homologs in different mammalian species. Podlevsky and Chen (2012) *Mutat. Res.* 730:3-11. In many species the telomere terminates in a single-stranded 3' overhang which inserts itself into the double stranded region, in association with telomere complex proteins, forming a loop within the telomere complex.

Telomeres shorten over time, due to oxidative damage and sister chromatid exchange, and also due to the end replication problem, in which the ends of chromosomes are not completely duplicated during mitosis. When telomeres become critically short, the telomere complex is no longer able to protect the chromosome ends, and the chromosome ends become "uncapped". Uncapping of the chromosome ends may result in chromosome-chromosome fusions, which may in turn result in cancer. O'Sullivan and Karlseder (2010) *Nat. Rev. Mol. Cell Biol.* 11:171-181; Calado et al. (2012) *Leukemia* 26:700-707; Artandi and DePinho (2010) *Carcinogenesis* 31:9-18. Uncapping can also result in the chromosome ends being recognized as damaged DNA, activating DNA damage responses and triggering cell apoptosis or senescence. Senescence is an arrested state in which the cell remains viable but no longer divides, and senescent cells typically cease to perform their normal, pre-senescence, useful functions adequately or at all. Thus telomere shortening leads to tissue dysfunction, loss of physical ability and youthful appearance, loss of mental ability, and disease in part due to the accumulation of senescent cells, and in part due to the loss of cells by apoptosis. Indeed, aged people with short telomeres are approximately 200-750% more likely to develop myocardial infarction (200%) (von Zglinicki et al. (2000) *Laboratory Investigation; a Journal of Technical Methods and Pathology* 80:1739-1747), vascular dementia (200%) (Testa et al. (2011) *Diabetic Medicine* 28:1388-1394, diabetes with complications (400%) (Blackburn et al. (2010) *Cancer Prevention Research* 3:394-402, cancer (Stern and Bryan (2008) *Cytogenetic and Genome Research* 122:243-254), stroke, Alzheimer's disease, infection (750%), idiopathic pulmonary fibrosis, and other disease. People with short telomeres in one tissue are likely to also have short telomeres in most of their other tissues, and thus short telomeres correlate with increased risk for many diseases in one individual. Takubo et al. (2010) *Geriatr Gerontol Int.* 10 Suppl 1:S197-206; doi: 10.1111/j.1447-0594.2010.00605.x. Short telomeres also limit cell replicative capacity which in turn limits cell therapies and regenerative therapies. Conversely, increasing telomere length in mice with short telomeres using virus-based genetic engineering methods rejuvenates the mice by several parameters, including skin thickness and elasticity, liver function, and sense of smell. Jaskelioff (2011) *Nature* 469:102-107.

Since telomerase extends telomeres, a useful approach to extending telomeres is to increase the level of telomerase activity in cells. Many agents and conditions have been reported to increase telomerase activity in cells, including the agents and conditions listed in Table 2.

TABLE 2

Examples of agents and conditions that increase telomerase activity

| Type | Examples |
| --- | --- |
| Growth factors | EGF, IGF-1, FGF-2, VEGF (Liu et al. (2010) *Ageing Research Reviews* 9: 245-256) |
| Genetic treatments | Viral delivery of DNA encoding TERT (Matsushita (2001) *Circ. Res.* 89: 793-798; Hooijberg (2000) *J. Immunol.* 165: 4239-4245); electroporation of plasmid encoding TERT (Bodnar et al. (1998) *Science* 279: 349-352); transfection of mRNA encoding TERT (Sæbe-Larssen et al. (2002) *J. Immunol. Methods* 259: 191-203) |
| Hormones | Estrogen (Imanishi et al. (2005) *Journal of Hypertension* 23: 1699-1706), erythropoietin (Akiyama et al. (2011) *Leukemia Research* 35: 416-418) |
| Physical treatments | UV radiation (Ueda et al. (1997) *Cancer Research* 57: 370-374), hypoxia (Gladych et al. (2011) *Biochemistry and Cell Biology* 89: 359-376) |
| Cytokines | IL-2, IL-4, IL-6, IL-7, IL-13, and IL-15 (Liu et al. (2010) *Ageing Research Reviews* 9: 245-256) |
| Small molecules from plants | Resveratrol (Pearce et al. (2008) *Oncogene* 27: 2365-2374), compounds extracted from *Astragalus membranaceus* including cycloastragenol (TAT2), TA-65, or TAT153 (Zvereva et al. (2010) *Biochemistry. Biokhimiia* 75: 1563-1583; Harley et al. (2011) *Rejuvenation Research* 14: 45-56) |
| Other | Inhibitors of Menin, SIP1 (Lin and Elledge (2003) *Cell* 113: 881-889), pRB, p38 (Di Mitri et al. (2011) *Journal of Immunology* 187: 2093-2100, p53, p73 (Beitzinger et al. (2006) *Oncogene* 25: 813-826, MKRN1, CHIP, Hsp70 (Lee et al. (2010) *The Journal of Biological Chemistry* 285: 42033-42045), androgens (Nicholls et al. (2011) *Protein & Cell* 2: 726-738), and TGF-beta (Prade-Houdellier et al. (2007) *Leukemia* 21: 2304-2310) |

The treatment examples of Table 2 are not without undesired effects, however. For example, treatment with growth factors, hormones, or cytokines may cause side effects, may activate multiple signaling pathways, may cause unwanted cell replication, may trigger an immune response, and are generally non-specific. Genetic treatments using plasmids or viruses carry a risk of genomic modification by insertional mutagenesis and a risk of cancer. Transfection with unmodified RNA causes a strong immune response and has not been shown to extend telomeres. Physical treatments can damage genomic DNA. Treatment with small molecules from plants have been found to only extend telomeres in some subjects and cells, only extend telomeres very slowly, and require chronic delivery, therefore risking cancer.

The expression in cells of nucleic acid sequences encoding hTERT and TERC, and the use of these components themselves, have been proposed to be useful in the diagnosis, prognosis, and treatment of human diseases (see, e.g., U.S. Pat. Nos. 5,583,016 and 6,166,178), but telomere extension in a manner that is both rapid and transient, and thus potentially safe for the reasons described above, has not been demonstrated. Sæbe-Larssen et al. (2002) *J. Immunol. Methods* 259:191-203 reported the transfection of dendritic cells with mRNA encoding hTERT, and that such cells acquired telomerase activity, but the transfection used standard mRNA and resulted in a strong hTERT cytotoxic T lymphocyte (CTL) response rather than an extension of telomeres.

Furthermore, all existing small-molecule treatments are largely ineffective and slow (Harley et al. (2011) *Rejuvenation Research* 14:45-56), primarily because they act through the catalytic component of telomerase, TERT, which is heavily regulated post-translationally, limiting existing treatments' effects to a small subset of cells, and excluding cells in interphase or G0 such as many stem and progenitor cells. Cifuentes-Rojas and Shippen (2012) *Mutat. Res.* 730: 20-27; doi:10.1016/j.mrfmmm.2011.10.003; Cong et al. (2002) *Microbiology and Molecular Biology Reviews* 66:407-425. This regulation is mediated in part by interactions between components of the telomerase complex, the telomere complex, and other molecules. For example, TERT is phosphorylated or dephosphorylated at multiple sites by multiple kinases and phosphatases, and at some sites, phosphorylation results in increased telomerase activity (for example phosphorylation by Akt), while at others sites phosphorylation reduces telomerase activity (for example, phosphorylation by Src1 or cAb1). Also, TERT is ubiquitinated or deubiquitinated at specific sites. TERT also interacts with other proteins at specific sites on TERT, and these interactions can inactivate TERT (for example interactions with Pinx1 or cAb1), or transport TERT away from the chromosomes (for example, interactions with CRM1 and Pinx1), preventing or slowing telomere extension. Further, some proteins bind to telomeres or the telomere complex, blocking TERT (for example POT1), preventing telomere extension. Further, some proteins aid telomere extension indirectly, for example helicases and UPF1. Due to regulatory mechanisms, telomerase activity peaks during S phase of the cell cycle, and thus rapidly-dividing cells may tend to benefit more from treatments that increase telomerase activity. However, it is often desirable to keep cells in a slow-dividing or non-dividing state; for example, stem or progenitor cells are often slow-dividing, and thus may spend the majority of their time in interphase or $G_0$. Thus, existing treatments are slow and ineffective in most cell types generally, and in all cell types during interphase and $G_0$. Treatments that are slow are less safe, because they require treatment for a longer time. Since telomere-shortening provides a protective safety mechanism against run-away cell proliferation, such as in cancer, a treatment that extends telomeres rapidly is generally safer, because it may be delivered for short periods of time and infrequently, thus allowing the normal telomere-shortening safety mechanism to remain in effect for much of the time. Therefore a method capable of transiently overcoming telomerase regulation to rapidly extend telomeres during a brief treatment is needed.

TERT regulates hundreds of genes including those listed in Table 3.

TABLE 3

Examples of genes and pathways regulated by TERT

| Type | Examples |
| --- | --- |
| | Upregulated |
| Epigenetic state modulators | DNA 5-methylcytosine transferase I (Young et al. (2003) *The Journal of Biological Chemistry* 278: 19904-19908) |
| Proto-oncogenes | Hepatocyte growth factor receptor (MET), AKT-2, CRK (Perrault et al. (2005) *Biochemical and Biophysical Research Communications* 335: 925-936) |
| Differentiation, cell fate | Sox-13 (Perrault et al. (2005) *Biochemical and Biophysical Research Communications* 335: 925-936), Wnt (Park et al. (2009) *Nature* 460: 66-72) |
| Glycolysis | Phosphofructokinase (Bagheri et al. (2006) *Proc. Nat'l Acad. Sci. U.S.A.* 103: 11306-11311), aldolase C (Bagheri et al. (2006) *Proc. Nat'l Acad. Sci. U.S.A.* 103: 11306-11311) |
| Proliferation enhancers | Activating transcription factor-3, Xbox protein-1, FGF, EGFR (Smith et al. (2003) *Nature Cell Biology* 5: 474-479), Insulin-like growth factor 2 (Perrault et al. (2005) *Biochemical and Biophysical Research Communications* 335: 925-936), Wnt (Park et al. (2009) *Nature* 460: 66-72), tp53bp1 (Perrault et al. (2005) *Biochemical and Biophysical Research Communications* 335: 925-936), epiregulin (Lindvall et al. (2003) *Cancer Research* 63: 1743-1747) |
| Metastasis-related genes | Mac-2 binding protein (Park et al. (2007) *International Journal of Cancer* 120: 813-820) |
| | Downregulated |
| Proliferation inhibitors | Interleukin 1 receptor antagonist, parathyroid hormone-related peptide, integrin-associated protein, TNF-related apoptosis-inducing ligand (Smith et al. (2003) *Nature Cell Biology* 5: 474-479), IGF binding protein-5 (Perrault et al. (2005) *Biochemical and Biophysical Research Communications* 335: 925-936), Melanoma inhibitory activity (Perrault et al. (2005) *Biochemical and Biophysical Research Communications* 335: 925-936), p21, p53 |
| Differentiation, cell fate | Transforming growth factor B2 (Perrault et al. (2005) *Biochemical and Biophysical Research Communications* 335: 925-936) |

In many cases, modulating the genes or pathways of Table 3 is undesirable because doing so can cause unwanted changes in cells. For example, TERT activates epigenetic regulators, which can change cell phenotype or interfere with efforts to reprogram or transdifferentiate cells for therapeutic purposes. TERT activates growth enhancers, but often proliferation is not desired, for example often stem cells with the most regenerative potential are those which divide slowly. TERT modulates regulators of cell fate and differentiation, which can impair efforts to differentiate cells into specific cell types. TERT also activates proto-oncogenes, which could lead to cancer. Thus, it is desirable to minimize the amount of time during which TERT levels are artificially elevated, including any treatment that extends telomeres using TERT. A treatment that extends telomeres by only transiently increasing telomerase activity levels is therefore needed.

In some cell types TERT has been shown to affect expression of other genes (Young et al. (2003) *J. Biol. Chem.* 278:19904-19908; Perrault et al. (2005) *Biochem. Biophys. Res. Commun.* 335:925-936), and this may not be desirable in some cases. Thus, a treatment that minimizes the amount of time during which TERT levels are increased is needed.

Compounds

The present invention addresses these problems by providing in one aspect novel compounds for the transient expression of exogenous telomerase in a cell. The compounds comprise a synthetic ribonucleic acid comprising at least one modified nucleoside and coding for a telomerase reverse transcriptase (TERT), wherein telomeres are extended within a cell treated with the compound.

Synthetic Ribonucleic Acids

The ribonucleic acids used in the transient expression of TERT according to various aspects of the instant invention comprise a ribonucleic acid coding for a TERT protein. The ribonucleic acids typically further comprise sequences that affect the expression and/or stability of the ribonucleic acid in the cell. For example, as shown in FIG. 1A, the ribonucleic acids may contain a 5' cap and untranslated region (UTR) to the 5' and/or 3' side of the coding sequence. The ribonucleic acids may further contain a 3' tail, such as a poly-A tail. The poly-A tail may, for example, increase the stability of the ribonucleic acid. In some embodiments, the poly-A tail is at least 75 nucleotides, 100 nucleotides, 125 nucleotides, 150 nucleotides, or even longer.

In some embodiments, the 5' cap of the ribonucleic acid is a non-immunogenic cap. In some embodiments, the 5' cap may increase the translation of the ribonucleic acid. In some embodiments, the 5' cap may be treated with phosphatase to modulate the innate immunogenicity of the ribonucleic acid. In some embodiments, the 5' cap is an anti-reverse cap analog ("ARCA"), such as a 3'-O-Me-m7G(5')ppp(5')G RNA cap structure analog.

As is well-known in the art, the above features, or others, may increase translation of the TERT protein encoded by the ribonucleic acid, may improve the stability of the ribonucleic acid itself, or may do both. In some embodiments, the 5' UTR and/or the 3' UTR are from a gene that has a very stable mRNA and/or an mRNA that is rapidly translated, for example, α-globin or β-globin, c-fos, or tobacco etch virus. In some embodiments, the 5' UTR and 3' UTR are from different genes, or are from different species than the species into which the compositions are being delivered. The UTRs may also be assemblies of parts of UTRs from the mRNAs of different genes, where the parts are selected to achieve a certain combination of stability and efficiency of translation.

The ribonucleic acids of the invention are preferably nucleoside-modified RNAs ("modRNA"). Most mature RNA molecules in eukaryotic cells contain nucleosides that are modified versions of the canonical unmodified RNA nucleosides, adenine, cytidine, guanosine, and uridine. Those modifications may prevent the RNA from being recognized as a foreign RNA. Karikó et al. (2005) *Immunity* 23:165-175. Synthetic RNA molecules made using certain nucleosides are much less immunogenic than unmodified RNA. The immunogenicity can be reduced even further by purifying the synthetic modRNA, for example by using high performance liquid chromatography (HPLC). The modified nucleosides may be, for example, chosen from the nucleosides shown in Table 4. The nucleosides are, in some embodiments, pseudouridine, 2-thiouridine, or 5-methylcytidine. Under some circumstances, it may be desirable for the modified RNA to retain some immunogenicity.

TABLE 4

Modified nucleosides found in eukaryotic RNA

| symbol | common name |
|---|---|
| $m^1A$ | 1-methyladenosine |
| $m^6A$ | $N^6$-methyladenosine |
| Am | 2'-O-methyladenosine |
| $i^6A$ | $N^6$-isopentenyladenosine |
| $io^6A$ | $N^6$-(cis-hydroxyisopentenyl)adenosine |
| $ms^2io^6A$ | 2-methylthio-$N^6$-(cis-hydroxyisopentenyl) adenosine |
| $g^6A$ | $N^6$-glycinylcarbamoyladenosine |
| $t^6A$ | $N^6$-threonylcarbamoyladenosine |
| $ms^2t^6A$ | 2-methylthio-$N^6$-threonyl carbamoyladenosine |
| Ar(p) | 2'-O-ribosyladenosine (phosphate) |
| $m^6_2A$ | $N^6,N^6$-dimethyladenosine |
| $m^6Am$ | $N^6,2'$-O-dimethyladenosine |
| $m^6_2Am$ | $N^6,N^6,2'$-O-trimethyladenosine |
| $m^1Am$ | 1,2'-O-dimethyladenosine |
| $m^3C$ | 3-methylcytidine |
| $m^5C$ | 5-methylcytidine |
| Cm | 2'-O-methylcytidine |
| $ac^4C$ | $N^4$-acetylcytidine |
| $f^5C$ | 5-formylcytidine |
| $m^4C$ | $N^4$-methylcytidine |
| $hm^5C$ | 5-hydroxymethylcytidine |
| $f^5Cm$ | 5-formyl-2'-O-methylcytidine |
| $m^1G$ | 1-methylguanosine |
| $m^2G$ | $N^2$-methylguanosine |
| $m^7G$ | 7-methylguanosine |
| Gm | 2'-O-methylguanosine |
| $m^2_2G$ | $N^2,N^2$-dimethylguanosine |
| Gr(p) | 2'-O-ribosylguanosine (phosphate) |
| yW | wybutosine |
| $o_2yW$ | peroxywybutosine |
| OHyW | hydroxywybutosine |
| OHyW* | undermodified hydroxywybutosine |
| imG | wyosine |
| $m^{2,7}G$ | $N^2,7$-dimethylguanosine |
| $m^{2,2,7}G$ | $N^2,N^2,7$-trimethylguanosine |
| I | inosine |

TABLE 4-continued

Modified nucleosides found in eukaryotic RNA

| symbol | common name |
|---|---|
| $m^1I$ | 1-methylinosine |
| Im | 2'-O-methylinosine |
| Q | queuosine |
| galQ | galactosyl-queuosine |
| manQ | mannosyl-queuosine |
| Ψ | pseudouridine |
| D | dihydrouridine |
| $m^5U$ | 5-methyluridine |
| Um | 2'-O-methyluridine |
| $m^5Um$ | 5,2'-O-dimethyluridine |
| $m^1Ψ$ | 1-methylpseudouridine |
| Ψm | 2'-O-methylpseudouridine |
| $s^2U$ | 2-thiouridine |
| $ho^5U$ | 5-hydroxyuridine |
| $chm^5U$ | 5-(carboxyhydroxymethyl)uridine |
| $mchm^5U$ | 5-(carboxyhydroxymethyl)uridine methyl ester |
| $mcm^5U$ | 5-methoxycarbonylmethyluridine |
| $mcm^5Um$ | 5-methoxycarbonylmethyl-2'-O-methyluridine |
| $mcm^5s^2U$ | 5-methoxycarbonylmethyl-2-thiouridine |
| $ncm^5U$ | 5-carbamoylmethyluridine |
| $ncm^5Um$ | 5-carbamoylmethyl-2'-O-methyluridine |
| $cmnm^5U$ | 5-carboxymethylaminomethyluridine |
| $m^3U$ | 3-methyluridine |
| $m^1acp^3Ψ$ | 1-methyl-3-(3-amino-3-carboxypropyl) pseudouridine |
| $cm^5U$ | 5-carboxymethyluridine |
| $m^3Um$ | 3,2'-O-dimethyluridine |
| $m^5D$ | 5-methyldihydrouridine |
| $τm^5U$ | 5-taurinomethyluridine |
| $τm^5s^2U$ | 5-taurinomethyl-2-thiouridine |

Without intending to be bound by theory, the presence of the modified nucleosides enables modRNA to avoid activation of an immune response mediated by various receptors, including the Toll-like receptors and RIG-1. Non-immunogenic modRNA has been used as a therapeutic agent in mice via topical delivery. Kormann et al. (2011) *Nature Biotechnology* 29:154-157. The discovery of nucleotide-modified mRNA facilitates the delivery of RNA-encoded therapeutic proteins, or mutants thereof, to cells, and the expression of those proteins in cells.

Accordingly, in some embodiments, the ribonucleic acids of the instant compositions comprise a pseudouridine, a 2-thiouridine, a 5-methylcytidine, or a nucleoside from Table 4. In some embodiments, the ribonucleic acids comprise more than one of the above nucleosides or combination of the above nucleosides. In highly preferred embodiments, the ribonucleic acids comprise pseudouridine and 5-methylcytidine.

In some embodiments, an immune response to the modRNA may be desired, and the RNA may be modified to induce an optimal level of innate immunity. In other embodiments, an immune response to the modRNA may not be desired, and the RNA may be modified in order to minimize such a reaction. The RNA can be modified for either situation.

The ribonucleic acids of the instant invention are preferably synthetic ribonucleic acids. The term "synthetic", as used herein, means that the ribonucleic acids are in some embodiments prepared using the tools of molecular biology under the direction of a human, for example as described below. The synthetic ribonucleic acids may, for example, be prepared by in vitro synthesis using cellular extracts or purified enzymes and nucleic acid templates. The synthetic ribonucleic acids may in some embodiments be prepared by chemical synthesis, either partially or completely. Alternatively, or in addition, the synthetic ribonucleic acids may in some embodiments be prepared by engineered expression in a cell, followed by disruption of the cell and at least partial purification of the ribonucleic acid. A synthetic ribonucleic acid is not, however, a naturally-occurring ribonucleic acid, as it is expressed in an unmodified cell without extraction or purification.

The ribonucleic acids of the instant invention may be prepared using a variety of standard techniques, as would be understood by one of ordinary skill in the art. In some embodiments, the ribonucleic acids may be prepared by in vitro synthesis, as described, for example, in U.S. Patent Application Publication Nos. 2009/0286852 and 2011/0143397. In some embodiments, the ribonucleic acids may be prepared by chemical synthesis. In some embodiments, the ribonucleic acids may be prepared by a combination of in vitro synthesis and chemical synthesis. As described above, the term "synthetic" should be understood to include ribonucleic acids that are prepared either by chemical synthesis, by in vitro synthesis, by expression in vivo and at least partial purification, or by a combination of such, or other, chemical or molecular biological methods.

The ribonucleic acids of the instant invention may, in some embodiments, be purified. As noted above, purification may reduce immunogenicity of the ribonucleic acids and may be advantageous in some circumstances. See also U.S. Patent Application Publication No. 2011/0143397. In preferred embodiments, the ribonucleic acids are purified by HPLC or by affinity capture and elution.

The protein structure of TERT includes at least three distinct domains: a long extension at the amino-terminus (the N-terminal extension, NTE) that contains conserved domains and an unstructured linker region; a catalytic reverse-transcriptase domain in the middle of the primary sequence that includes seven conserved RT motifs; and a short extension at the carboxyl-terminus (the C-terminal extension, CTE). Autexier and Lue (2006) *Annu Rev Biochem.* 75:493-517. In some embodiments, the ribonucleic acid of the instant invention codes for a full-length TERT. In some embodiments, the ribonucleic acid codes for a catalytic reverse transcriptase domain of TERT. In some embodiments, the ribonucleic acid codes for a polypeptide having TERT activity.

The TERT encoded by the ribonucleic acids of the instant disclosure is preferably a mammalian, avian, reptilian, or fish TERT. More preferably, the TERT is a mammalian TERT, such as human TERT. Meyerson et al. (1997) *Cell* 90:785-795; Nakamura et al. (1997) *Science* 277:955-959; Wick et al. (1999) *Gene* 232:97-106. The amino acid sequence of two human TERT isoforms are available as NCBI Reference Sequences: NP_937983.2 and NP_001180305.1. Other non-limiting exemplary amino acid sequences usefully encoded by the ribonucleic acids of the instant compositions include TERT from cat (NCBI Reference Sequence: XP_003981636.1), dog (NCBI Reference Sequence: NP_001026800.1), mouse (NCBI Reference Sequence: NP_033380.1), cow (NCBI Reference Sequence: NP_001039707.1), sheep NCBI Reference Sequence: XP_004017220.1), pig (NCBI Reference Sequence: NP_001231229.1), African elephant (NCBI Reference Sequence: XP_003408191.1), chicken (NCBI Reference Sequence: NP_001026178.1), rat (NCBI Reference Sequence: NP_445875.1), zebrafish (NCBI Reference Sequence: NP_001077335.1); Japanese medaka (NCBI Reference Sequence: NP_001098286.1); and chimpanzee (NCBI Reference Sequences: XP_003950543.1 and XP_003950544.1).

It should be understood that the ribonucleic acids of the instant invention may code for variants of any of the above-listed amino acid sequences, particularly variants that retain telomerase catalytic activity, including truncated variants. In some embodiments, the ribonucleic acids of the instant compositions code for one of the above-listed amino acid sequences or a sequence with at least 95% sequence identity to that sequence. In some embodiments, the nucleic acids of the instant compositions code for one of the above-listed amino acid sequences or a sequence with at least 98%, 99%, 99.9%, or even higher sequence identity to that sequence.

It should also be understood that the instant ribonucleic acids may correspond to the native gene sequences coding for the above-listed TERT proteins or may correspond to variants that are made possible due to the redundancy of the genetic code, as would be understood by one of ordinary skill in the art. In some embodiments, the codon selection may be optimized to optimize protein expression using algorithms and methods known by those of ordinary skill in the art. Fath et al. (2011) *PLoS ONE* 6:3.

Compositions

In another aspect, the present invention provides compositions for the extension of telomeres in a cell, the compositions comprising a compound of the invention, as described above, and a further component. In some embodiments, the compositions further comprise a telomerase RNA component (TERC). (See also Table 6 below.) In some embodiments, the compositions further comprise a delivery vehicle.

Delivery Vehicles

As just noted, the compositions of the instant disclosure may further comprise a delivery vehicle for the ribonucleic acid. The delivery vehicle may, in some cases, facilitate targeting and uptake of the ribonucleic acid of the composition to the target cell. In particular, the compositions of the instant disclosure may comprise any gene delivery vehicle known in the field, for example nanoparticles, liposomes, gene gun ballistic particles, viruses, cationic lipids, commercial products, such as Lipofectamine® RNAiMax, or other vehicles. In some embodiments, the delivery vehicle is an exosome, a lipid nanoparticle, a polymeric nanoparticle, a natural or artificial lipoprotein particle, a cationic lipid, a protein, a protein-nucleic acid complex, a liposome, a virosome, or a polymer. In some preferred embodiments, the delivery vehicle is a cationic lipid formulation. Viral delivery is typically not preferred, however, as it can lead to insertional mutagenesis.

In some preferred embodiments, the delivery vehicle is an exosome, a lipid nanoparticle, or a polymeric nanoparticle. In highly preferred embodiments, the delivery vehicle is an exosome. Exosomes are naturally-occurring lipid bilayer vesicles 40-100 nm in diameter. Exosomes contain a set of specific proteins, including the membrane protein Lamp-1 and Lamp-2, which are particularly abundant. Lakhal and Wood (2011) *BioEssays: News and Reviews in Molecular, Cellular and Developmental Biology* 33:737-741. In 2007, exosomes were discovered to be natural carriers of RNA and protein, including over 1,300 types of mRNA and 121 types of non-coding microRNA. Exosomes can also transmit mRNA between species: exposure of human cells to mouse exosomes carrying mouse mRNA results in translation in the human cells of the mouse mRNA.

Figure 2:
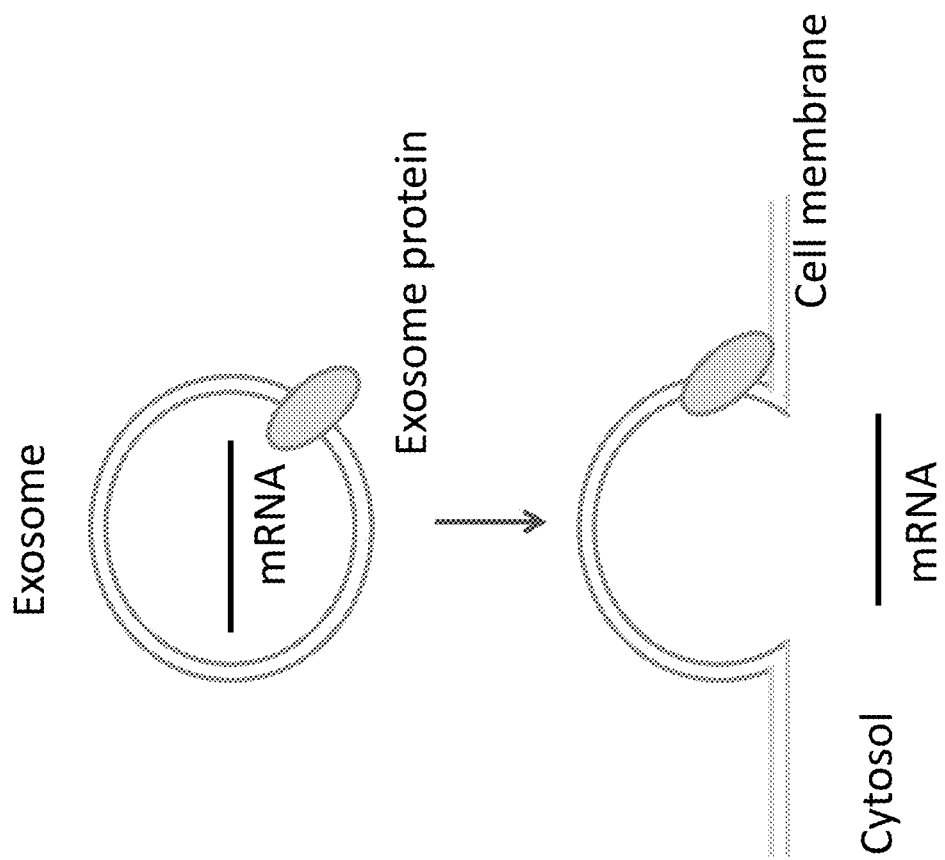
FIG. 2. Use of exosomes as a delivery vehicle for ribonucleic acid therapeutics.

As delivery vehicles for RNA, protein, or DNA, exosomes have a number of advantages over alternative vehicles. Specifically, exosomes can be generated from a patient's own cells, making them non-immunogenic—they are therefore not attacked by antibodies, complement, coagulation factors, or opsonins. In addition, exosomes can be loaded with nucleic acids by electroporation, and they are naturally-occurring vehicles that carry mRNA and protein between human cells. Exosomes protect their RNA and protein cargo during transport, and the cargo is delivered directly into the cytosol. They can extravasate from the blood stream to extravascular tissues, even crossing the blood-brain barrier, and they can be targeted. Furthermore, exosomes avoid being accumulated in untargeted organs, such as, for example, liver. Exosomes may therefore be used as cell-derived "liposomes" to deliver therapeutic mRNA or other cargo in the treatment of disease. Mizrak et al. (2013) *Molecular Therapy* 21:101-108; doi:10.1038/mt.2012.161. A graphic illustration of an exosome delivering an mRNA to a cell is shown in FIG. 2. See also van den Boom et al. (2011) *Nature Biotechnology* 29:325-326.

Most cell types are believed to be capable of generating exosomes, and exosomes are found in most biological fluids including blood, saliva, urine, cerebrospinal fluid, breast milk, and amniotic fluid. Exosomes are produced by most cell types, in different abundance. Abundant exosomes, devoid of T-cell activators, can be derived from immature dendritic cells, which are present in human blood. O'Doherty et al. (1994) *Immunology* 82:487-493. Exosomes may also be produced artificially, for example by combining recombinant exosomal proteins with lipids and phospholipids such as are found in exosomal membranes. Alternatively, exosomes may be constructed by in vitro self-assembly of liposomes with a subset of exosomal surface proteins.

The drug delivery potential of exosomes was first demonstrated in 2011. Alvarez-Erviti et al. (2011) *Nature Biotechnology* 29:341-345. Specifically, exosomes were harvested from dendritic cells engineered to express a Lamp2B fusion protein fused to a 28 a.a. targeting ligand from rabies virus glycoprotein (RVG), then electroporated siRNA into the exosomes and injected the exosomes into mice immunocompatible with the mice from which they obtained the dendritic cells. The exosomes were thus autologous, and did not generate an immune response, as measured by IL-6, IP-10, TNF-α, and IFN-α levels. Further, repeated doses over one month elicited similar responses, demonstrating that there was no adaptive immune response either.

As described above, exosomes can be autologous and thus have low immunogenicity. Since modRNA also has low immunogenicity, the combination of modRNA as the ribonucleic acid and an exosome as the delivery vehicle in the compositions of the instant disclosure is particularly preferred. In these embodiments, the disclosure thus provides a new way of delivering mRNA or modRNA to cells or tissues, using exosomes. Such delivery provides a useful method to temporarily increase the level of any protein in a cell in vivo using RNA delivered in exosomes by intravenous or topical injection, and particularly in the delivery of an RNA encoding TERT. Accordingly, in preferred embodiments, the delivery vehicles of the instant compositions are non-immunogenic. Under some circumstances, however, it may be desirable for the vehicle to retain some immunogenicity.

Additional Components

The compositions disclosed herein may further comprise additional components that either enhance the delivery of the composition to the target cell, enhance the extension of telomeres within the cell, or both. For example, the compositions may further comprise one or more of the compounds and conditions of Table 2. As would be understood by one of ordinary skill in the art, combinations of active ingredients often display synergistic effects on a desired activity, such as, for example, the transient expression of exogenous telomerase activity in a cell, and such combinations are understood to fall within the scope of the invention. Additional examples of proteins that may be included within the compositions of the instant disclosure are listed in Table 5. It should be understood that the compositions could either include the proteins themselves, or nucleic acid sequences, preferably RNAs or modRNAs, that encode these proteins, or proteins with high sequence identity that retain the activity of the listed protein.

TABLE 5

Proteins usefully delivered in combination with TERT

| Species | Protein | Activity | Advantages | Reference |
|---|---|---|---|---|
| Human | UPF1 | Sustains telomere leading strand-replication | Increased rate or amount of telomere extension. | Chawla et al. (2011) *The EMBO Journal* 30: 4047-4058 |
| Human | HSP90 | Prevents dephosphorylation of Akt kinase by PP2A. Akt needs to be phosphorylated to phosphorylate TERT. Also complexes with TERT and keeps TERT serine 823 phosphorylated, keeping TERT activated. Büchner et al. (2010) *Antioxidants & Redox Signaling* 13: 551-558. | Increased TERT activity. | Haendeler et al. (2003) *FEBS Letters* 536: 180-186; Büchner et al. (2010) *Antioxidants & Redox Signaling* 13: 551-558 |
| Human | Akt kinase (aka protein kinase B) | Complexes with TERT and HSP90, phosphorylates TERT at serine 823, increasing TERT activity. Büchner et al. (2010) *Antioxidants & Redox Signaling* 13: 551-558 | Increased TERT activity. | Wojtyla et al. (2011) *Molecular Biology Reports* 38: 3339-3349; Büchner et al. (2010) *Antioxidants & Redox Signaling* 13: 551-558 |
| Human | Protein kinase C (PKC) (its various isoenzymes) | Phosphorylates TERT, allowing it to bind nuclear translocator. | Nuclear translocation. | Wojtyla et al. (2011) *Molecular Biology Reports* 38: 3339-3349 |

TABLE 5-continued

Proteins usefully delivered in combination with TERT

| Species | Protein | Activity | Advantages | Reference |
|---|---|---|---|---|
| Human | Shp-2 | Inhibits phosphorylation of TERT Y707 by Src1, keeping TERT in nucleus. Transport of TERT to nucleus. | Nuclear translocation. | Wojtyla et al. (2011) *Molecular Biology Reports* 38: 3339-3349 |
| Human | TPP1 | Recruits telomerase to the telomere. | | Abreu et al. (2010) *Molecular and Cellular Biology* 30: 2971-2982 |
| Human | NFkB p65 | Transport of TERT to nucleus. | Nuclear translocation. | Wojtyla et al. (2011) *Molecular Biology Reports* 38: 3339-3349 |
| Human | Rap1 | regulator of telomere length. | Extension of telomeres. | O'Connor et al. (2004) *The Journal of Biological Chemistry* 279: 28585-28591 |

Other examples of agents that may usefully be included within the compositions of the instant disclosure are listed in Table 6.

TABLE 6

Other agents usefully delivered in combination with TERT

| Molecule | Activity | Advantages | Reference |
|---|---|---|---|
| Okadaic acid | Inhibits PP2A. PP2A dephosphorylates AKT and or TERT. AKT phosphorylates TERT, activating it. | Increased telomerase activity due to TERT phosphorylation. | Wojtyla et al. (2011) *Molecular Biology Reports* 38: 3339-3349 |
| TERRA or anti-sense TERRA (ARRET) | TERRA inhibits telomerase by binding to TERC, to which it is complementary. | Antisense TERRA, or ARRET, should increase telomerase activity by binding to TERRA, preventing it from binding to TERC. | Cifuentes-Rojas and Shippen (2012) Mutat. Res. 730: 20-27; doi: 10.1016/j.mrfmmm.2011.10.003 |
| TERC RNA | RNA component of telomerase, essential for its function, may be second-most limiting factor after TERT in most cells. | Increase telomerase activity. | |

Since TERT is most active during certain phases of the cell cycle, the compositions of the instant disclosure may also optionally include one or more transient activators of cellular proliferation, in order to enhance the effectiveness of the TERT treatment. Such agents may include, for example, an RNAi agent that transiently reduces the amounts of cell cycle inhibitors such as Rb or P19/Arf in the cell. Other transient activators of cellular proliferation may be usefully included in the instant compositions, as would be understood by one of ordinary skill in the art.

Methods of Extending Telomeres and Methods of Treatment

In another aspect, the instant disclosure provides methods of extending telomeres, comprising the step of administering any of the above-described compounds or compositions to a cell with shortened telomeres, wherein telomeres are extended within the cell. The instant disclosure also provides methods of treatment, comprising the step of administering any of the above-described compounds or compositions to an animal subject in need of, or that may benefit from, telomere extension.

In preferred embodiments, the compounds or compositions are administered to a cell, wherein the cell is an isolated cell or is part of a cell culture, an isolated tissue culture, an isolated organ, or the like (i.e., the administration is in vitro).

In other preferred embodiments, the compounds or compositions are administered without isolating the cell or cells, the tissue, or the organ from the subject (i.e., the administration is in vivo). In some of these embodiments, the compound or composition is delivered to all, or almost all, cells in the subject's body. In some embodiments, the compound or composition is delivered to a specific cell or tissue in the subject's body.

In some embodiments, the subject is a mammal, bird, fish, or reptile. In preferred embodiments, the subject is a mammal and more preferably a human. In other preferred embodiments, the subject is a pet animal, a zoo animal, a livestock animal, or an endangered species animal. Examples of preferred subject species are listed in Table 7.

TABLE 7

Subject animal species.

Dog (*Canis lupus familiaris*)
Sheep (*Ovis aries*)
Domestic pig (*Sus scrofa domesticus*)
Domestic goat (*Capra aegagrus hircus*)
Cattle (*Bos primigenius taurus*)
Zebu (*Bos primigenius indicus*)
Cat (*Felis catus*)
Chicken (*Gallus gallus domesticus*)
Guinea pig (*Cavia porcellus*)
Donkey (*Equus africanus asinus*)
Domesticated duck (*Anas platyrhynchos domesticus*)
Water buffalo (*Bubalus bubalis*)
Horse (*Equus ferus caballus*)
Domesticated Silkmoth (*Bombyx mori*)
Domestic Pigeon (*Columba livia domestica*)
Domestic goose (*Anser anser domesticus*)
Llama (*Lama glama*)
Alpaca (*Vicugna pacos*)
Domesticated guineafowl (*Numida meleagris*)
Ferret (*Mustela putorius furo*)
Ringneck dove (*Streptopelia risoria*)
Bali cattle (*Bos javanicus domestica*)
Gayal (*Bos frontalis*)
Domesticated turkey (*Meleagris gallopavo*)
Goldfish (*Carassius auratus auratus*)
Domestic rabbit (*Oryctolagus cuniculus*)
Domestic Canary (*Serinus canaria domestica*)
Carabao (*Bubalus bubalis carabenesis*)
Siamese fighting fish (*Betta splendens*)
Koi (*Cyprinus carpio haematopterus*)
Domesticated silver fox (*Vulpes vulpes*)
Domesticated hedgehog (*Atelerix albiventris*)
Society Finch (*Lonchura striata domestica*)
Yak (*Bos grunniens*)
Fancy rat and Lab rat
Domesticated Dromedary Camel (*Camelus dromedarius*)
Domesticated Bactrian Camel (*Camelus bactrianus*)
Guppy (*Poecilia reticulata* some strains)
Fancy mouse For in vitro applications, the compounds or compositions may be administered using any suitable technique, as would be understood by those skilled in the fields of cell biology, cell culture, tissue culture, organ culture, or the like. For in vivo applications, the compounds or compositions are usefully administered by injection, topical application, inhalation, or any other suitable administration technique, as would be understood by those of ordinary skill in the medical arts or the like.

As described above, cells usefully treated according to the methods of the disclosure include cells, either in a subject (for in vivo administration) or from a subject (for in vitro administration), that may benefit from telomere extension. Since short telomeres affect almost all cell types in most animals, telomere extension may benefit most animals. A telomere extension treatment that is transient and brief has the potential to be safe, as described above. Telomere extension using a transient treatment as disclosed herein may therefore be of use in all or most individuals either as a preventive measure, for example to prevent or delay onset of the many diseases and conditions in which short telomeres are implicated, or as a treatment for those diseases and conditions. The treatment may benefit subjects at risk of age-related diseases or conditions, or who are already suffering from such diseases, and may also benefit subjects who have experienced, are experiencing, or are at risk of experiencing physical trauma or chronic physical stress such as hard exercise or manual labor, or psychological trauma or chronic psychological stress, since all of these conditions cause telomere shortening; physical stress or trauma requires cell division in order to repair the resultant damage, thus shortening telomeres, and these conditions may also cause oxidative stress, which also shortens telomeres. Such diseases and conditions include, for example, metabolic syndrome, diabetes, diabetic ulcers, heart disease, many forms of cancer, vascular dementia, Alzheimer's, stroke, age-related macular degeneration, immunosenescence, bone marrow failure, gastrointestinal ulcers, cirrhosis, hernia, infection such as pneumonia secondary to impaired immune function, chronic infection, mild or severe cognitive impairment, impaired mobility, osteoporosis, osteoarthritis, rheumatoid arthritis, age-related anxiety, balance disorders, tinnitus, Bell's palsy, cataracts, COPD, corneal abrasion, coronary artery disease, peripheral artery disease, conjunctivitis, chalazion, dehydration, depression, emphysema, various eye diseases, failure to thrive, flu, generalized anxiety disorder, glaucoma, hearing loss, loss of sense of taste, loss of appetite, hip dislocation, memory loss, Parkinson's disease, spinal stenosis, urinary incontinence, vertebral fracture, and others.

Cells usefully treated according to the instant methods may also include cells in or from a subject that suffers from an age-related illness or condition or that is at risk of suffering from such an illness or condition. Such age-related illnesses and conditions may include genetic diseases in which genes encoding components of the telomerase complex or telomere complex are mutated, thus leading to short telomeres. Such diseases include, for example, forms of idiopathic pulmonary fibrosis, dyskeratosis congenita, and aplastic anemia.

In the case of genetic diseases, the compositions may therefore further include additional nucleic acids, such as the normal, functional versions of the coding sequences of the genes that are affected by such diseases, for example DKC1, TINF2, NOP10, NHP2, TERC, or other genes. Examples of such genes are listed in Table 8. See also Armanios (2009) *Ann. Rev. Genomics Hum. Genet.* 10: 45-61.

TABLE 8

Genes related to age-related diseases.

| Gene | Diagnosis | Age of onset in years (typical) |
| --- | --- | --- |
| hTR | Sporadic IPF 1-3% | Broad range of ages |
| hTERT | Familial IPF 8-15% | 5-77 |
|  | Sporadic and familial aplastic anemia ~3-5% |  |
|  | Autosomal dominant dyskeratosis congenital (DC) |  |
| DKC1 | X-linked DC | Less than 30 |
|  | Hoyeraal-Hreiderasson | Less than 5 |
| TINF2 | Sporadic DC | Less than 10 |
|  | Autosomal dominant DC | — |
|  | Hoyeraal-Hreiderasson | Less than 5 |
| NOP10 | Autosomal Recessive DC | — |
| NHP2 | Autosomal Recessive DC | — |

In addition, the treatment may benefit subjects suffering from, or at risk of, other types of genetic diseases in which short telomeres may play a role, such as, for example, muscular dystrophy. In such diseases, the need for cell replication to address the problem caused by the genetic mutation shortens telomeres more rapidly than normal, resulting in more rapid telomere shortening than normal, which in turn exhausts the replicative capacity of cells, leading to tissue dysfunction, exacerbated or additional symptoms, disability, and often death. In addition, various types of cancer may be prevented or delayed by treatment with compounds of the invention, and indeed chromosome-chromosome fusions caused by critically short telomeres are believed to be a cause of cancer. Telomeres may also be selectively lengthened in healthy cells in an individual, while not lengthening telomeres in cancer cells, which may allow the instant compounds, compositions, and methods to be used, for example, to lengthen telomeres of the immune system to increase its ability to fight a cancer. Further, immune system cells may be harvested from an individual for treatment using the invention ex vivo followed by reintroduction into the individual.

In some embodiments, the cells treated according to the instant methods are from subjects where no disease state is yet manifested but where the subject is at risk for a condition or disease involving short telomeres, or where the cells contain shortened telomeres. In some embodiments, the age-related illness is simply old age. The instant treatments may also be used as a cosmetic aid, to prevent, delay, or ameliorate age-related deterioration in appearance of skin, hair, bone structure, posture, eye clarity, or other traits that decline with aging. For example, the treatments may be used to help maintain skin elasticity, thickness, smoothness, and appearance, since telomere extension improves these parameters. In cases of physical trauma such as a bone fracture or a tissue crush or cut injury or burn, the invention may be used to increase the lengths of telomeres in cells which participate in healing the trauma, to increase their replicative capacity. In cases of chronic physical stress, which causes telomere shortening, treatment with the invention may lengthen telomeres in affected cells increasing their replicative capacity and ability to repair tissue damage. Since telomere shortening accumulates over generations, for example in humans with haploinsufficiency of telomerase components such as hTR or hTERT, Armanios (2009) *Annu. Rev. Genomics Hum. Genet.* 10:45-61, the treatments of the instant disclosure may be applied to germ line cells such as eggs, sperm, or their precursors, or to fertilized eggs or embryos, for example during in vitro fertilization procedures. The treatments may also be useful for aiding other treatments of various diseases or conditions, for example, transdifferentiation of cells in vivo. The treatment methods may also be useful in advance of or during surgery or chemotherapy, or radiotherapy, to increase the ability of cells to replicate to repair damage resulting from these procedures.

The methods may also be useful for treating cells in vitro for various applications, including autologous or heterologous cell therapy, bioengineering, tissue engineering, growth of artificial organs, generation of induced pluripotent stem cells (iPSC), and cellular differentiation, dedifferentiation, or transdifferentiation. In these applications, cells may be required to divide many times, which may lead to loss of telomere length, which may be counteracted by the invention before, during, or after the application.

In addition, various types of cancer may be considered age-related illnesses, particularly where the cancerous cells contain short telomeres. In some cases, the cells treated according to the instant methods are from subjects where no disease state is yet manifested but where the cells contain shortened telomeres. In some embodiments, the age-related illness is simply the altered form and function typically associated with old chronological age in humans.

The cells usefully administered compounds or compositions of the instant disclosure according to the instant methods include cells from any tissue or cell type that may suffer the effects of shortened telomeres or that may in any way benefit from lengthening of the cell's telomeres. Cells may include somatic cells or germ cells, as well as stem cells and other progenitor cells and/or undifferentiated cells. Cells may include tumor cells and non-tumor cells.

Examples of cells usefully administered compounds or compositions according to the instant methods include cells that are derived primarily from endoderm, cells that are derived primarily from ectoderm, and cells that are derived primarily from mesoderm. Cells derived primarily from the endoderm include, for example, exocrine secretory epithelial cells and hormone-secreting cells. Cells derived primarily from the ectoderm include, for example, cells of the integumentary system (e.g., keratinizing epithelial cells and wet stratified barrier epithelial cells) and the nervous system (e.g., sensory transducer cells, autonomic neuron cells, sense organ and peripheral neuron supporting cells, central nervous system neurons and glial cells, and lens cells). Cells derived primarily from the mesoderm include, for example, metabolism and storage cells, barrier-function cells (e.g., cells of the lung, gut, exocrine glands, and urogenital tract), extracellular matrix cells, contractile cells, blood and immune system cells, germ cells, nurse cells, and interstitial cells. Accordingly, in some embodiments of the instant methods, the cell administered the composition is a somatic cell of endodermal, mesodermal, or ectodermal lineage. In some embodiments the cell is a germ line cell or an embryonic cell.

Specific examples of cells that may be administered a compound or composition according to the instant methods include, e.g., salivary gland mucous cells, salivary gland serous cells, von Ebner's gland cells in tongue, mammary gland cells, lacrimal gland cells, ceruminous gland cells in ear, eccrine sweat gland dark cells, eccrine sweat gland clear cells, apocrine sweat gland cells, gland of Moll cells in eyelid, sebaceous gland cells, Bowman's gland cells in nose, Brunner's gland cells in duodenum, seminal vesicle cells, prostate gland cells, bulbourethral gland cells, Bartholin's gland cells, gland of Littre cells, uterus endometrium cells, isolated goblet cells of the respiratory and digestive tracts, stomach lining mucous cells, gastric gland zymogenic cells, gastric gland oxyntic cells, pancreatic acinar cells, paneth cells of the small intestine, type II pneumocytes of the lung, clara cells of the lung, anterior pituitary cells (e.g., somatotropes, lactotropes, thyrotropes, gonadotropes, and corticotropes), intermediate pituitary cells (e.g., those secreting melanocyte-stimulating hormone), magnocellular neurosecretory cells (e.g., those secreting oxytocin or vasopressin), gut and respiratory tract cells, (e.g., those secreting serotonin, endorphin, somatostatin, gastrin, secretin, cholecystokinin, insulin, glucagon, or bombesin), thyroid gland cells (e.g., thyroid epithelial cells and parafollicular cells), parathyroid gland cells (e.g., parathyroid chief cells and oxyphil cells), adrenal gland cells (e.g., chromaffin cells and cells secreting steroid hormones such as mineralcorticoids and glucocorticoids), Leydig cells of testes, theca interna cells of the ovarian follicle, corpus luteum cells of the ruptured ovarian follicle, granulosa lutein cells, theca lutein cells, juxtaglomerular cells, macula densa cells of the kidney, peripolar cells of the kidney, mesangial cells of the kidney, epidermal keratinocytes, epidermal basal cells, keratinocytes of fingernails and toenails, nail bed basal cells, medullary hair shaft cells, cortical hair shaft cells, cuticular hair shaft cells, cuticular hair root sheath cells, hair root sheath cells of Huxley's layer, hair root sheath cells of Henle's layer, external hair root sheath cells, hair matrix cells, surface epithelial cells of the stratified squamous epithelium of the cornea, tongue, oral cavity, esophagus, anal canal, distal urethra, and vagina, basal cells of the epithelia of the cornea, tongue, oral cavity, esophagus, anal canal, distal urethra, and vagina, urinary epithelium cells (e.g., lining the urinary bladder and urinary ducts), auditory inner hair cells of the organ of Corti, auditory outer hair cells of the organ of Corti, basal cells of the olfactory epithelium, cold-sensitive primary sensory neurons, heat-sensitive primary sensory neurons, Merkel cells of the epidermis, olfactory receptor neurons, pain-sensitive primary sensory neurons, photoreceptor cells of the retina in the eye (e.g., photoreceptor rod cells, photoreceptor blue-sensitive cone cells, photoreceptor green-sensitive cone cells, and photoreceptor red-sensitive cone cells), proprioceptive primary sensory neurons, touch-sensitive primary sensory neurons, type I and II carotid body cells, type I and II hair cells of the vestibular apparatus of the ear, type I taste bud cells, cholinergic neural cells, adrenergic neural cells, peptidergic neural cells, inner and outer pillar cells of the organ of Corti, inner and outer phalangeal cells of the organ of Corti, border cells of the organ of Corti, Hensen cells of the organ of Corti, vestibular apparatus supporting cells, taste bud supporting cells, olfactory epithelium supporting cells, Schwann cells, satellite glial cells, enteric glial cells, astrocytes, neuron cells, oligodendrocytes, spindle neurons, anterior lens epithelial cells, crystallin-containing lens fiber cells, hepatocytes, adipocytes (e.g., white fat cells and brown fat cells), liver lipocytes, kidney parietal cells, kidney glomerulus podocytes, kidney proximal tubule brush border cells, loop of Henle thin segment cells, kidney distal tubule cells, kidney collecting duct cells, type I pneumocytes, pancreatic duct cells, nonstriated duct cells (e.g., principal cells and intercalated cells), duct cells (of seminal vesicle, prostate gland, etc.), intestinal brush border cells (with microvilli), exocrine gland striated duct cells, gall bladder epithelial cells, ductulus efferens nonciliated cells, epididymal principal cells, epididymal basal cells, ameloblast epithelial cells, planum semilunatum epithelial cells of the vestibular apparatus of the ear, organ of Corti interdental epithelial cells, loose connective tissue fibroblasts, corneal fibroblasts (corneal keratocytes), tendon fibroblasts, bone marrow reticular tissue fibroblasts, other nonepithelial fibroblasts, pericytes, nucleus pulposus cells of the intervertebral disc, cementoblasts/cementocytes, odontoblasts/odontocytes, hyaline cartilage chondrocytes, fibrocartilage chondrocytes, elastic cartilage chondrocytes, osteoblasts/osteocytes, osteoprogenitor cells, hyalocytes of the vitreous body of the eye, stellate cells of the perilymphatic space of the ear, hepatic stellate cells (Ito cells), pancreatic stelle cells, skeletal muscle cells (e.g., red skeletal muscle cells (slow) and white skeletal muscle cells (fast)), intermediate skeletal muscle cells, nuclear bag cells of the muscle spindle, nuclear chain cells of the muscle spindle, satellite cells, heart muscle cells (e.g., ordinary heart muscle cells, nodal heart muscle cells, and Purkinje fiber cells, smooth muscle cells (various types), myoepithelial cells of the iris, myoepithelial cells of the exocrine glands, erythrocytes, megakaryocytes, monocytes, connective tissue macrophages (various types). epidermal Langerhans cells, osteoclasts, dendritic cells, microglial cells, neutrophil granulocytes, eosinophil granulocytes, basophil granulocytes, hybridoma cells, mast cells, helper T cells, suppressor T cells, cytotoxic T cells, natural killer T cells, B cells, natural killer cells, reticulocytes, stem cells and committed progenitors for the blood and immune system (various types), oogonia/oocytes, spermatids, spermatocytes, spermatogonium cells, spermatozoa, nurse cells, ovarian follicle cells, sertoli cells, thymus epithelial cells, and interstitial kidney cells.

In a preferred embodiment, the cells administered a compound or composition according to the instant methods are stem or progenitor cells, since these cells give rise to other cells of the body. In another preferred embodiment, the cells treated are cells in which telomeres shorten more quickly than in other cell types, for example endothelial cells, fibroblasts, keratinocytes, cells of the immune system including thyroid and parathyroid cells and leukocytes and their progenitors, cells of the intestines, liver, mucosal membrane cells, e.g. in the esophagus and colon, and cells of the gums and dental pulp.

Accordingly, in some embodiments, the cells are fibroblast cells, keratinocytes, endothelial cells, epithelial cells, or blood cells.

The administering step may be performed one or more times depending on the amount of telomere extension desired. In some embodiments of the instant methods, the cell is an isolated cell, and the administering step lasts no longer than 96 hours, no longer than 72 hours, no longer than 48 hours, no longer than 36 hours, no longer than 24 hours, no longer than 18 hours, no longer than 12 hours, no longer than 8 hours, no longer than 4 hours, or even shorter times. In some embodiments, the administering step lasts at least 2 hours, at least 4 hours, at least 8 hours, at least 12 hours, at least 18 hours, at least 24 hours, at least 36 hours, at least 48 hours, or even longer times. In preferred embodiments, the administering step lasts no longer than 48 hours, no longer than 96 hours, or no longer than 1 week. In other preferred embodiments, the administering step lasts at least 2 hours. It should be understood that, in the case where administration is by transfection, the time for administration includes the time for the cell to recover from the transfection method.

In some embodiments of the instant methods, the cell is an isolated cell, and the administering step is performed no more than 6 times, no more than 5 times, no more than 4 times, no more than 3 times, no more than 2 times, or even no more than 1 time. In some embodiments, the administering step is performed not less than 2 times, not less than 3 times, not less than 4 times, not less than 5 times, not less than 6 times, or even more often.

In some embodiments, the administering step is performed once or a few times over a relatively brief period to re-extend telomeres, and then not performed for a prolonged period until telomeres need to be extended again. This cycle may be repeated indefinitely. Such a treatment schedule allows telomeres to be periodically re-extended, with intervals in between administration steps during which telomeres shorten. Periodic treatment methods may be performed either by in vivo administration or by in vitro administration, as desired. In some embodiments, the administering step in such a series is performed no more than 6 times, no more than 5 times, no more than 4 times, no more than 3 times, no more than 2 times, or even no more than 1 time. In some embodiments, the administering step is performed not less than 2 times, not less than 3 times, not less than 4 times, not less than 5 times, not less than 6 times, or even more often. By varying the number of times the administering step is performed, and the dose of the compounds our compositions of the invention used, the amount of telomere extension achieved can be controlled.

In some embodiments, the methods of the instant disclosure further include the step of culturing the cell on a specific substrate, preferably an elastic substrate. Such substrates are known to prevent unwanted changes in the cell that would normally occur on other substrates due to the non-physiological elasticity of those substrates. See PCT International Publication No. WO2012/009682, which is incorporated by reference herein in its entirety. Elastic substrates may additionally promote cell survival.

Administration of the compounds or compositions of the instant disclosure results in the transient expression of a telomerase activity in the cell. The increased activity is readily measured by various assays, such as, for example, the Trapeze® RT telomerase detection kit (Millipore), which provides a sensitive, real-time in vitro assay using fluorimetric detection and quantitation of telomerase activity, although other measurement techniques are also possible. In some embodiments, the telomerase activity is increased by at least 5%, at least 10%, at least 20%, at least 30%, at least 50%, or even more. In preferred embodiments, the telomerase activity is increased by at least 5%.

As previously noted, one of the advantages of the instant techniques is that the expression of telomerase activity is transient in the treated cells. In particular, such transient expression is in contrast to previous techniques where a telomerase reverse transcriptase gene is inserted into the genomic sequence of the cell or otherwise permanently modifies the genetic make-up of the targeted cell and results in constitutive activity of the nucleic acid sequence.

Figure 3:
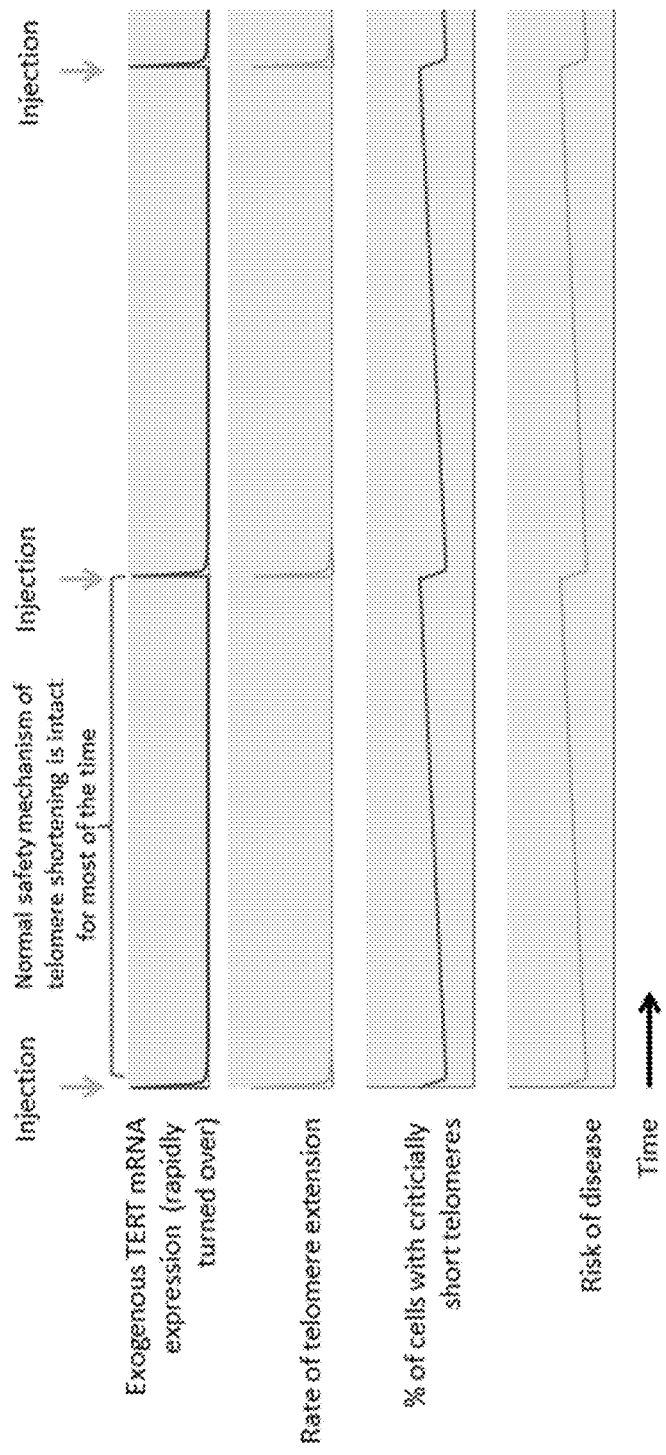
FIG. 3. Graphical illustration of the use of multiple rapid and transient telomerase treatments in the extension of telomeres in a cell.

FIG. 3 graphically illustrates some of the advantages of the compounds, compositions, and methods disclosed herein. In particular, the speed of telomere extension made possible with these compounds, compositions, and methods enables telomere maintenance by very infrequent delivery of TERT modRNA. The expressed telomerase activity rapidly extends telomeres in a brief period, before being turned over, thus allowing the protective anti-cancer mechanism of telomere-shortening to function most of the time. Between treatments, normal telomerase activity and telomere shortening is present, and therefore the anti-cancer safety mechanism of telomere shortening to prevent out-of-control proliferation remains intact, while the risk of short telomere-related disease remains low. In contrast, the best existing small molecule treatment for extending telomeres requires chronic delivery, and thus presents a chronic cancer risk, and even then has a small, inconsistent effect on telomere length, with no detectable effect on telomere length at all in about half of patients.

Accordingly, in some embodiments of the instant methods, the expression of telomerase reverse transcriptase activity, i.e., the half-life of telomerase activity, lasts no longer than 48 hours, no longer than 36 hours, no longer than 24 hours, no longer than 18 hours, no longer than 12 hours, no longer than 8 hours, no longer than 4 hours, or even shorter times. In some embodiments, the expression of telomerase reverse transcriptase activity lasts at least 2 hours, at least 4 hours, at least 8 hours, at least 12 hours, at least 18 hours, at least 24 hours, at least 36 hours, at least 48 hours, or even longer times. In preferred embodiments, the expression of telomerase reverse transcriptase activity lasts no longer than 48 hours. In other preferred embodiments, the expression of telomerase reverse transcriptase activity lasts at least 2 hours.

In some embodiments of the instant methods, the transient expression is independent of cell cycle.

As noted above, the transient expression of telomerase reverse transcriptase results in the extension of shortened telomeres in treated cells. Telomere length can be readily measured using techniques such as terminal restriction fragment (TRF) length analysis, qPCR, MMqPCR, and Q-FISH, as would be understood by one of ordinary skill in the art. See, e.g., Kimura et al. (2010) *Nat Protoc.* 5:1596-607; doi: 10.1038/nprot.2010.124. In some embodiments, the instant methods increase telomere length in treated cells by at least 0.1 kb, at least 0.2 kb, at least 0.3 kb, at least 0.4 kb, at least 0.5 kb, at least 1 kb, at least 2 kb, at least 3 kb, at least 4 kb, at least 5 kb, or even more.

One of the advantages of the instant compounds, compositions, and methods, is the rapidity of extension of telomeres achieved by these techniques. The techniques allow treatments to be brief and thus safe because the normal protective telomere shortening mechanism remains intact for most of the time. Treatment with the compounds and compositions disclosed herein result in delivery of tens or hundreds of copies of TERT modRNA per cell as measured by absolute RT-qPCR, which is substantially more than the average number of copies of endogenous TERT mRNA found even in cells with high telomerase activity. Typically such cells have less than one copy of TERT mRNA per cell (Yi et al. (2001) *Nucl. Acids Res.* 29:4818-4825). Thus the treatments transiently introduce a large number of copies of modRNA encoding TERT to a cell resulting in rapid telomere extension. Without intending to be bound by theory, the large number of copies of modRNA encoding TERT may transiently overwhelm the inhibitory regulatory mechanisms that normally prevent TERT, and other methods of telomere extension, from extending telomeres as rapidly as the compounds, compositions, and methods disclosed herein.

The transient expression of telomerase reverse transcriptase also results in an increased replicative capacity in treated cells. Increased replicative capacity is readily monitored in cells that are approaching replicative senescence by measuring additional population doublings in such cells. Senescent cells are not stimulated to divide by passage in culture or treatment with serum. Senescent cells are further often characterized by the expression of pH-dependent β-galactosidase activity, expression of cell cycle inhibitors p53 and p19, and other altered patterns of gene expression, and an enlarged cell size. Absent treatment with the compounds and compositions of the instant disclosure, human lung fibroblast cells typically double 50-60 times. With one set of one to three treatments lasting only a few days total, however, these cells achieve an additional 16-28 population doublings. If treated again several weeks later, additional proliferative capacity is conferred again. This process of intermittent treatments to periodically re-extend telomeres may be applied additional times, with the interval between treatments depending on factors such as the rate of telomere shortening, the rate of cell divisions, and the amount of telomere extension provided by the treatment. Likewise, human microvascular dermal endothelial cells from an aged individual, absent treatment with the instant compositions, may achieve only 1-2 population doublings, whereas treated cells may achieve 3, 4, or even more population doublings.

Accordingly, in some embodiments, the instant treatment methods increase the number of population doublings by at least one, two, four, or even more population doublings. In some embodiments, the treatment methods increase the number of population doublings by at least 5, 10, 15, 20, or even more population doublings.

In some of the instant method embodiments, the compounds or compositions of the invention are administered to the animal cell by electroporation. In specific embodiments, a compound of the invention is administered to the animal cell by electroporation in the absence of a delivery vehicle. In other specific embodiments a compound of the invention and a telomerase RNA component are administered to the animal cell by electroporation.

Kits

In another aspect, the instant disclosure provides ready-to-use kits for use in extending telomeres in a mammalian cell. The kits comprise any of the above-described compounds or compositions, together with instructions for their use. In some embodiments, the kits further comprise packaging materials. In preferred embodiments, the packaging materials are air-tight. In these embodiments, the packaging materials may optionally be filled with an inert gas, such as, for example, nitrogen, argon, or the like. In some embodiments, the packaging materials comprise a metal foil container, such as, for example, a sealed aluminum pouch or the like. Such packaging materials are well known by those of ordinary skill in the art.

In some embodiments, the kit may further comprise a desiccant, a culture medium, an RNase inhibitor, or other such components. In some embodiments, the kit may further comprise a combination of more than one of these additional components. In some kit embodiments, the composition of the kit is sterile.

Further Aspects

In yet another aspect, the invention provides novel compounds, compositions, kits, and methods according to the following numbered paragraphs:

1. A composition for the extension of telomeres comprising:
    a ribonucleic acid comprising at least one modified nucleoside and coding for a telomerase reverse transcriptase; and
    a delivery vehicle for the ribonucleic acid; wherein telomeres are extended within a cell treated with the composition.
2. The composition of paragraph 1, wherein the telomerase reverse transcriptase is a mammalian, avian, reptilian, or fish telomerase reverse transcriptase or a variant that retains telomerase catalytic activity.
3. The composition of paragraph 2, wherein the telomerase reverse transcriptase is a human telomerase reverse transcriptase.
4. The composition of paragraph 1, wherein the ribonucleic acid comprises a 5' cap, a 5' untranslated region, a 3' untranslated region, and a poly-A tail.
5. The composition of paragraph 4, wherein the poly-A tail increases stability of the ribonucleic acid.
6. The composition of paragraph 4, wherein the 5' untranslated region or the 3' untranslated region comprise a sequence from a stable mRNA or an mRNA that is efficiently translated.
7. The composition of paragraph 4, wherein the 5' untranslated region and the 3' untranslated region both comprise a sequence from a stable mRNA or an mRNA that is efficiently translated.
8. The composition of paragraph 4, wherein the 5' cap, the 5' untranslated region, or the 3' untranslated region stabilizes the ribonucleic acid, increases the rate of translation of the ribonucleic acid, or reduces the immunogenicity of the ribonucleic acid.
9. The composition of paragraph 1, wherein the at least one modified nucleoside reduces immunogenicity of the ribonucleic acid.
10. The composition of paragraph 1, wherein the ribonucleic acid is a synthetic ribonucleic acid.
11. The composition of paragraph 10, wherein the synthetic ribonucleic acid is a purified synthetic ribonucleic acid.
12. The composition of paragraph 11, wherein the synthetic ribonucleic acid is purified to remove immunogenic components.
13. The composition of paragraph 1, wherein the ribonucleic acid codes for a human, cat, dog, mouse, cow, sheep, pig, African elephant, chicken, rat, zebrafish, Japanese medaka, or chimpanzee telomerase reverse transcriptase, or a polypeptide with at least 95% sequence identity to the telomerase reverse transcriptase.
14. The composition of paragraph 1, wherein the composition further comprises a telomerase RNA component.
15. The composition of paragraph 14, wherein the telomerase RNA component is a mammalian, avian, reptilian, or fish telomerase RNA component.
16. The composition of paragraph 15, wherein the telomerase RNA component is a human telomerase RNA component.
17. The composition of paragraph 1, wherein the delivery vehicle is an exosome, a lipid nanoparticle, a polymeric nanoparticle, a natural or artificial lipoprotein particle, a cationic lipid, a protein, a protein-nucleic acid complex, a liposome, a virosome, or a polymer.
18. The composition of paragraph 17, wherein the delivery vehicle is a cationic lipid.
19. The composition of paragraph 1, wherein the delivery vehicle is non-immunogenic.
20. A method of extending telomeres, comprising the step of: administering the composition of any one of paragraphs 1 to 19 to an animal cell, wherein at least one telomere is extended within the cell.
21. The method of paragraph 20, wherein the cell has at least one shortened telomere prior to the administering step.
22. The method of paragraph 20, wherein the cell is from a subject suffering from or at risk of an age-related illness, an age-related condition, or an age-related decline in function or appearance.
23. The method of paragraph 20, wherein the cell is from a subject suffering from or at risk of cancer, heart disease, stroke, diabetes, Alzheimer's disease, osteoporosis, a decline in physical ability or appearance, physical trauma or chronic physical stress, or psychological trauma or chronic psychological stress.
24. The method of paragraph 20, wherein the cell is a somatic cell of endodermal, mesodermal, or ectodermal lineage, or a germ line or embryonic cell.
25. The method of paragraph 20, wherein the cell is an induced pluripotent stem cell or a cell used to produce an induced pluripotent stem cell.
26. The method of paragraph 20, wherein the cell is a transdifferentiated cell or a cell used to produce a transdifferentiated cell.
27. The method of paragraph 20, wherein the cell is an isolated cell, and the administering step lasts no longer than 48 hours.
28. The method of paragraph 20, wherein the cell is an isolated cell, and the administering step is performed no more than four times.
29. The method of paragraph 20, wherein the cell is an isolated cell, and the method further comprises the step of measuring telomerase activity in the cell.
30. The method of paragraph 29, wherein the administering step increases telomerase activity in the cell.
31. The method of paragraph 30, wherein the telomerase activity is transiently increased by at least 5%.
32. The method of paragraph 30, wherein the half-life of increased telomerase activity lasts no longer than 48 hours.
33. The method of paragraph 20, wherein the cell is an isolated cell, and the method further comprises the step of measuring average telomere length in the cell.
34. The method of paragraph 33, wherein average telomere length is increased by at least 0.1 kb.

35. The method of paragraph 20, wherein the cell is an isolated cell, and the method further comprises the step of measuring population doubling capacity in the cell.
36. The method of paragraph 35, wherein the population doubling capacity increases by at least 25%.
37. The method of paragraph 20, wherein the cell is from a mammalian subject.
38. The method of paragraph 37, wherein the cell is from a human subject.
39. The method of paragraph 20, wherein the cell is an isolated cell.
40. The method of paragraph 20, wherein the cell is not an isolated cell.
41. A kit for extending telomeres in an animal cell, comprising:
    the composition of any one of paragraphs 1 to 19; and
    instructions for using the composition to extend telomeres.
42. The kit of paragraph 41, further comprising packaging materials.
43. The kit of paragraph 42, wherein the packaging materials are air-tight.
44. The kit of paragraph 42, wherein the packaging materials comprise a metal foil container.
45. The kit of paragraph 41, further comprising a desiccant.
46. The kit of paragraph 41, further comprising a culture medium.
47. The kit of paragraph 41, further comprising an RNase inhibitor.
48. The kit of paragraph 41, wherein the composition is sterile.

It will be readily apparent to one of ordinary skill in the relevant arts that other suitable modifications and adaptations to the compounds, compositions, methods, and kits described herein may be made without departing from the scope of the invention or any embodiment thereof. Having now described the present invention in detail, the same will be more clearly understood by reference to the following Examples, which are included herewith for purposes of illustration only and are not intended to be limiting of the invention.

EXAMPLES

Example 1

Highly Efficient Telomere Extension in Human Cells Using Modified mRNA Encoding Telomerase Diseases of inadequate telomere length maintenance and the need for increased cell replicative capacity for cell therapies and bioengineering applications motivate development of safe methods for telomere extension. Blackburn et al. (2010) *Cancer Prev Res (Phila)* 3:394-402; Calado et al. (2012) *Leukemia* 26:700-707; Alter et al. (2009) *Blood* 113:6549-6557; Mohsin et al. (2012) *Journal of the American College of Cardiology* doi:10.1016/j.jacc.2012.04.047. mRNA delivery to transiently increase the amount of protein encoded by the mRNA for therapeutic applications is facilitated by incorporation of modified nucleosides reduce immunogenicity and increase stability. Karikó et al. (2005) *Immunity* 23:165-175; Karikó et al. (2011) *Nucleic Acids Res.* 39:e142; doi: 10.1093/nar/gkr695.

To be therapeutically useful, a telomere extension treatment should ideally be non-immunogenic; specific; capable of being initiated before telomeres shorten to the critically short lengths that cause chromosomal instability and increased cancer risk (Wentzensen et al. (2011) *Cancer Epidemiol. Biomarkers Prev.* 20:1238-1250; Calado et al. (2012) *Leukemia* 26:700-707; Artandi and DePinho (2010) *Carcinogenesis* 31:9-18); transient and intermittent, to allow the normal anti-cancer telomere shortening mechanism to function almost continuously; effective even in slow-dividing cells such as some progenitor and stem cell populations; deliverable in vitro and in vivo using non-immunogenic vehicles; and, finite, enabling only enough additional cell divisions to potentially ameliorate or prevent diseases of inadequate telomere maintenance, or to enable sufficient amplification of cells for cell therapies or bioengineering applications. Existing treatments, including treatments using small molecules, do not meet all of these criteria. Harley et al. (2011) *Rejuvenation Res.* 14:45-56. Viral delivery of TERT, while possibly inducible, risks insertional mutagenesis and thus presents serious safety concerns. Treatments involving continuous telomerase overexpression are potentially unsafe, because in a cell with an oncogenic mutation, either due to critically short telomeres and resulting chromosomal instability (O'Sullivan and Karlseder (2010) *Nat. Rev. Mol. Cell Biol.* 11:171-181) or another cause, constitutive telomerase expression, either due to a second mutation or a drug, may support malignancy by enabling unlimited proliferation. Artandi and DePinho (2010) *Carcinogenesis* 31:9-18; Ding et al. (2012) *Cell* 148:896-907.

The criteria for safe telomere extension are met by an RNA-based approach, facilitated by the recent discovery that certain naturally-occurring nucleosides found in RNA increase the stability and reduce the immunogenicity of exogenous RNA when delivered to cells. Karikó et al. (2005) *Immunity* 23:165-175. Examples of such nucleosides are listed in Table 4. Without intending to be bound by theory, these modified versions of canonical nucleosides may allow Toll-like receptors of the innate immune system to distinguish endogenous modRNA from foreign RNA not containing these nucleotides. Delivery of sufficiently purified synthetic modRNA containing these non-canonical nucleosides to cells results in increased stability of the modRNA and transient elevation of the protein encoded by the modRNA with reduced or abrogated immune response. Karikó et al. (2011) *Nucleic Acids Res.* 39:e142; doi: 10.1093/nar/gkr695. Thus, delivery of exogenous modRNA presents unprecedented opportunities for applications which require transient protein production. For example, biomimetic modRNA has been transfected into fibroblasts, thus reprogramming them to pluripotent stem cells. Yakubov et al. (2010) *Biochem. Biophys. Res. Commun.* 394:189-193. Biomimetic modRNA has also been injected into mice to rescue a model of pulmonary surfactant protein deficiency and to elevate erythropoietin and hematocrit levels. Kormann et al. (2011) *Nat. Biotechnol.* 29:154-157. As described above, the nucleosides used in the modRNAs used herein were chosen not only to increase the stability but also to reduce or abrogate immunogenicity and to increase translational efficiency of the RNA. Transfection of dendritic cells using an unmodified mRNA encoding hTERT, while resulting in an increase in telomerase activity within the cells also elicited a strong hTERT-specific cytotoxic T lymphocyte response. Saeboe-Larssen et al. (2002) *Journal of Immunological Methods* 259: 191-203. Approaches using unmodified RNAs are therefore not likely to be effective in extending telomeres in cells.

Thus, delivery of modRNA encoding TERT to cells may be used to transiently increase levels of TERT protein and telomerase activity sufficiently to extend telomeres and increase replicative capacity by a finite amount. The increased levels of telomerase activity occur rapidly enough to enable a telomere extension treatment that is brief and infrequent (see FIG. 1A and FIG. 3).

To demonstrate the approach, TERT modRNA was synthesized using ratios of canonical and non-canonical nucleosides that confer stability, efficient translation, and reduced or abrogated immunogenicity. Yakubov et al. (2010) *Biochem. Biophys. Res. Commun.* 394:189-193; Karikó et al. (2011) *Nucleic Acids Res.* 39:e142; doi: 10.1093/nar/gkr695. The synthetic modRNA contains the 5' and 3' UTRs of beta globin mRNA, which has a relatively long half-life. To further enhance stability the modRNA has a long, 151 nucleotide poly-A tail. To maximize the fidelity of the long TERT DNA template used in the in vitro transcription reaction to generate RNA, the DNA templates were generated using a plasmid—rather than PCR-based approach.

To distinguish bona fide telomere extension from selection of cells with long telomeres from a heterogeneous starting population, a control modRNA was synthesized that encodes a catalytically inactive form of TERT (CI TERT) with the single residue mutation D712A, in which one of the triad of metal-coordinating aspartates at the catalytic site of the reverse transcriptase domain is substituted with alanine, abrogating the catalytic activity of CI TERT but leaving it structurally intact to the extent of being able to bind template DNA, and as stable as TERT in reticulocyte lysate. Wyatt (2009) "Structure-Function Analysis of the Human Telomerase Reverse Transcriptase" University of Calgary, Ph.D. Thesis (http://dspace.ucalgary.ca/bitstream/1880/47511/1/2009_Wyatt_PhD.pdf).

MRC-5 human fetal lung fibroblasts were chosen as test cells in this example because these and other human fibroblast strains have served for decades as workhorses in the telomere field and there is thus abundant data to inform experimental design and analysis. MRC-5 cells also have relatively low endogenous telomerase activity, and exhibit telomere shortening and eventual senescence. Since oxidative stress increases the rate of telomere shortening in MRC-5 cells (von Zglinicki et al. (2000) *Free Radic. Biol. Med.* 28:64-74), and causes TERT to localize to the cytoplasm where it cannot extend telomeres (Ahmed et al. (2008) *J. Cell. Sci.* 121:1046-1053), the cells were cultured in 5% rather than ambient oxygen. To further increase the likelihood of success the cells were also cultured in medium optimized for protein production in MRC-5 cells (Wu et al. (2005) *Cytotechnology* 49:95-107).

Figure 1B:
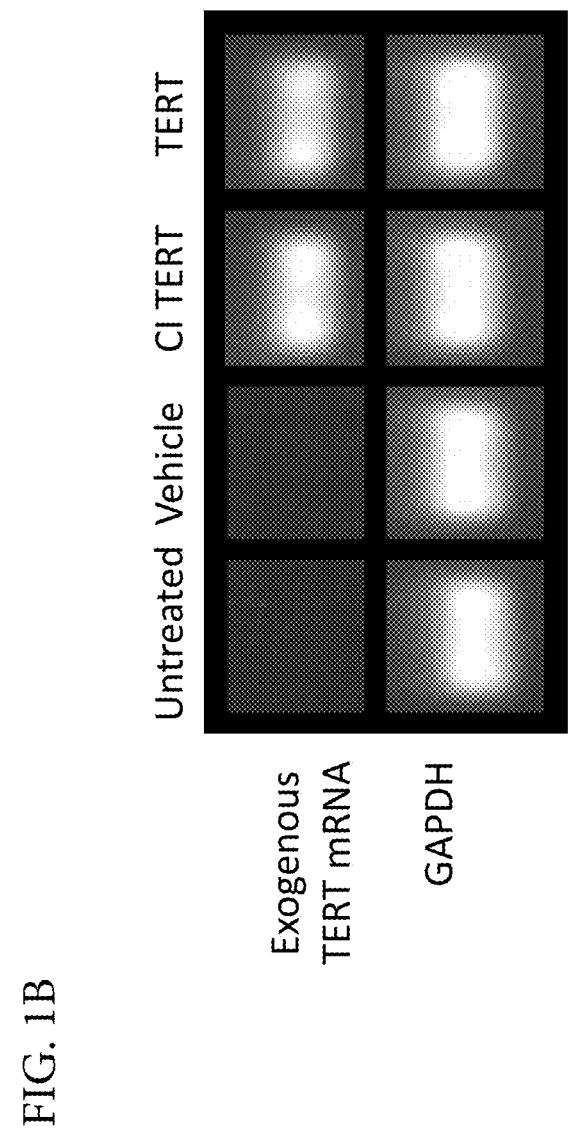
Figure 1C:
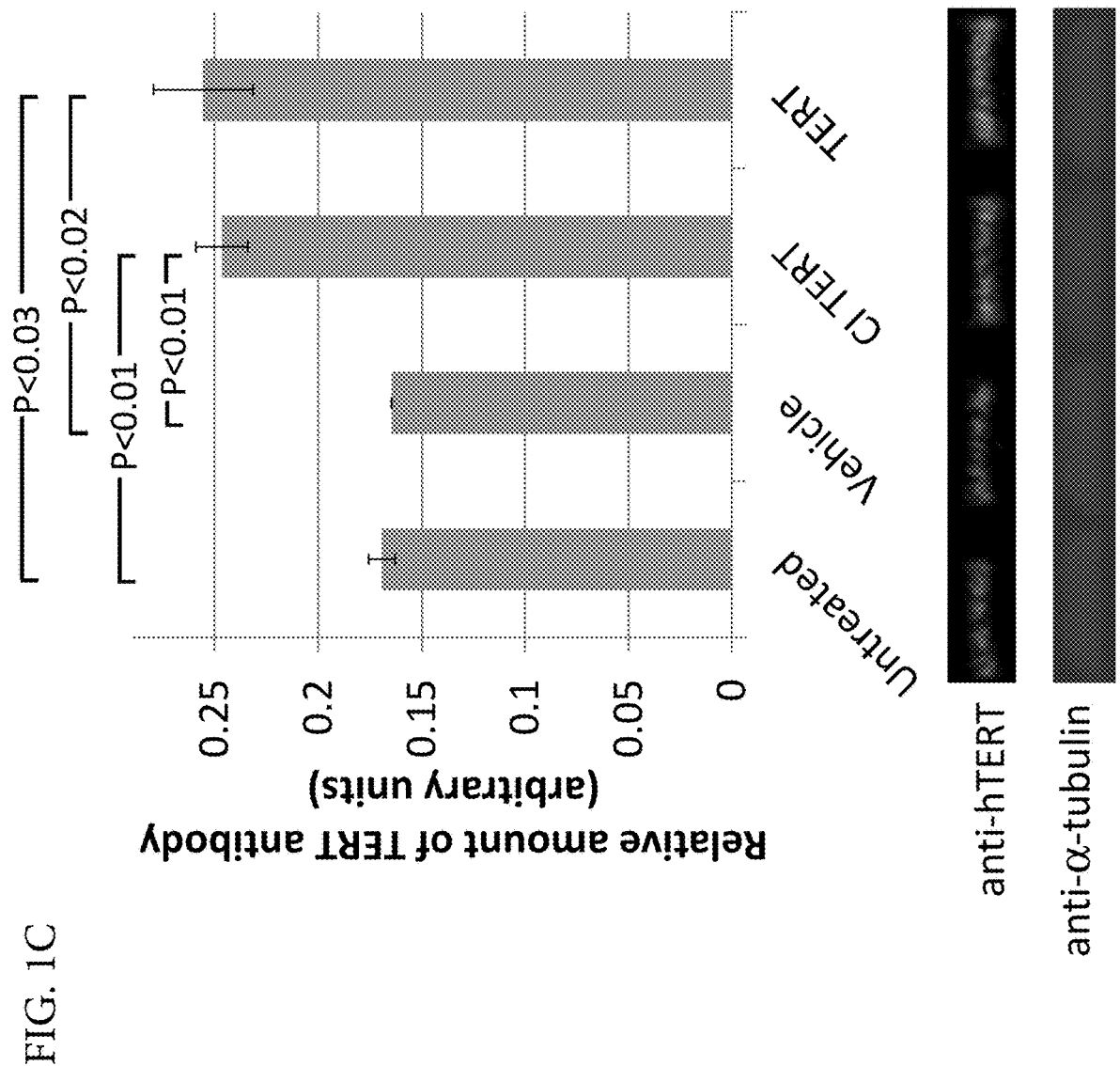
Figure 6C:
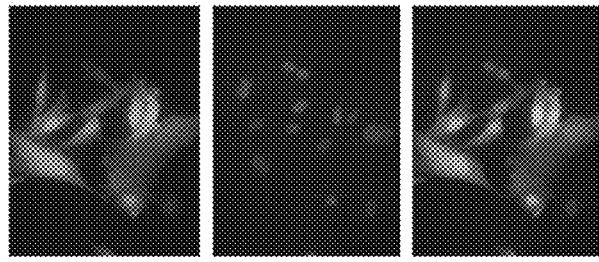
FIGS. 6A-6C. High efficiency of transfection of MRC-5 cells treated with modRNA encoding nuclear GFP (nGFP).
Figure 6A:
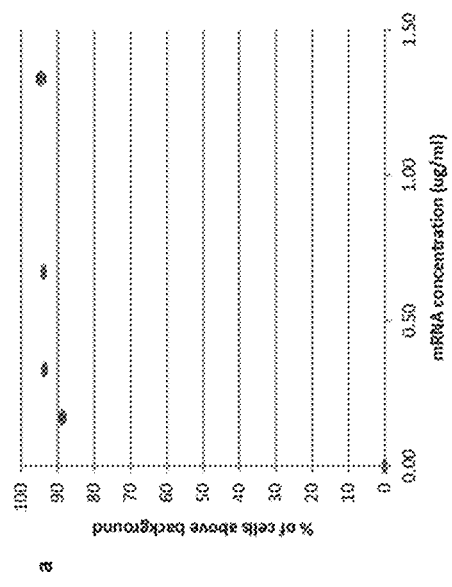
Figure 6B:
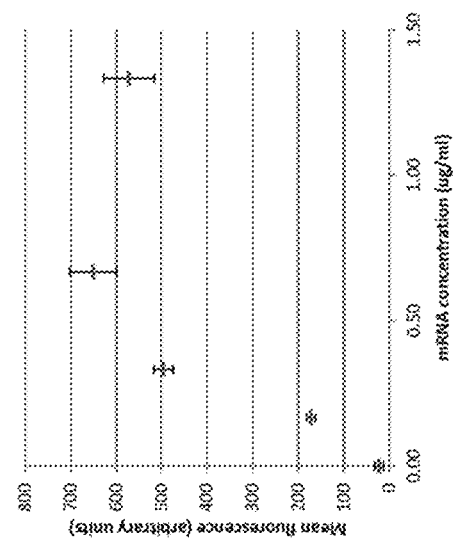

The efficiency of modRNA-based telomere extension is subject to several factors, including efficiency of transfection, translation, and folding into functional telomerase, and ability to at least transiently escape the extensive mechanisms of post-translational regulation that inhibit TERT and telomerase in many cell types including MRC-5 cells. While the transfection efficiencies with smaller modRNA species such as nGFP (0.8 kb) in MRC-5 cells are typically over 90% even with low concentrations of modRNA (FIGS. 6A-6C), the TERT open reading frame is relatively large (3399 bp), and the modRNA TERT construct includes UTRs and a poly-A tail, thus making the construct even larger (3751 bp). As shown in FIG. 1B, however, both TERT and CI TERT were efficiently transfected into MRC-5 cells by cationic lipid (as measured by RT-PCR of mRNA harvested at end of treatment from MRC-5 cells treated with 1 ug/ml TERT modRNA for 5 hours). Further, delivery of TERT or CI TERT modRNA resulted in equivalent and significant ($P<0.03$ and $<0.01$, respectively) increases in the amount of protein recognized by anti-TERT antibody, with a size of approximately 122 kDa, close to the estimated size of TERT of 127 kDa (FIG. 1C). Wick et al. (1999) *Gene* 232:97-106. Protein levels were measured by quantitative infrared fluorescence Western blot. TERT protein levels do not differ significantly between cells treated with TERT and cells treated with CI TERT (n=3).

Figure 1D:
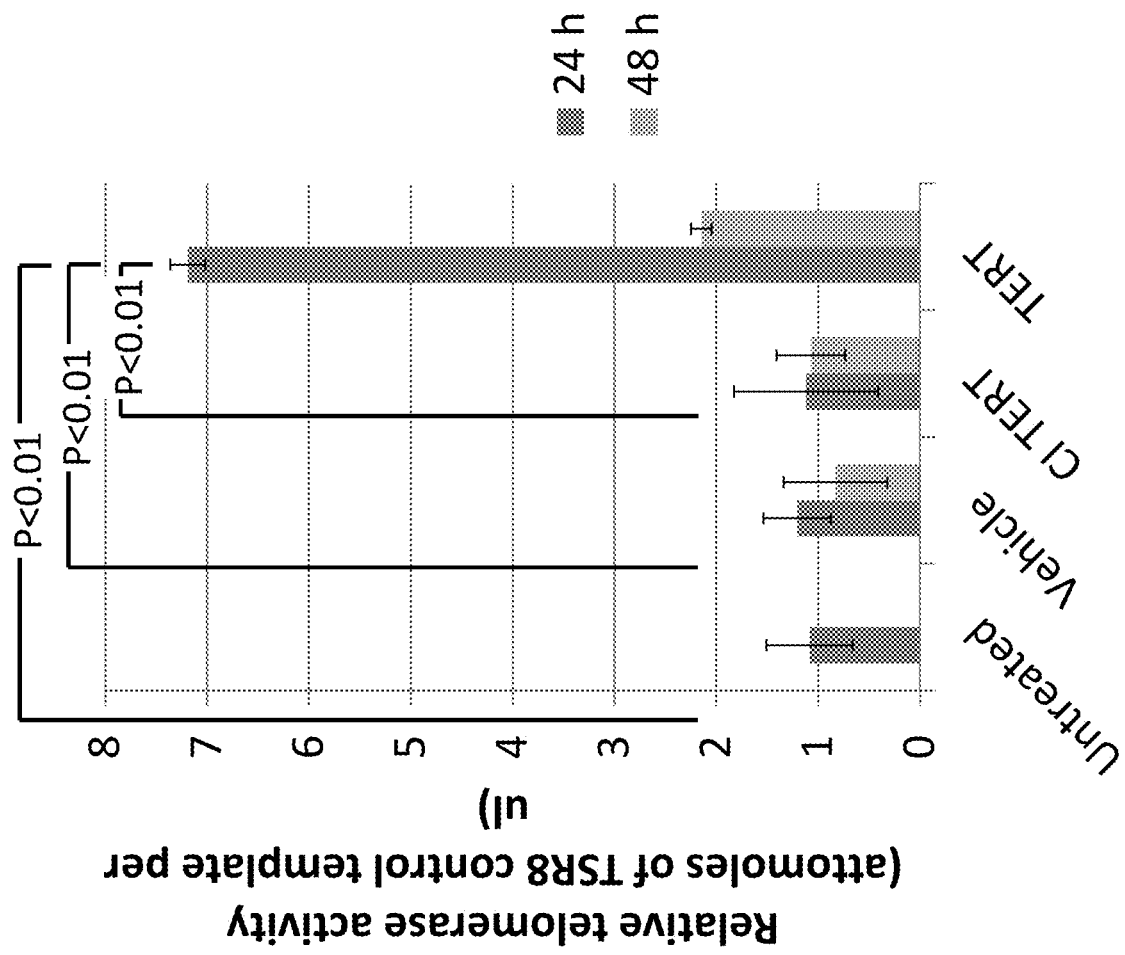
Figure 7:
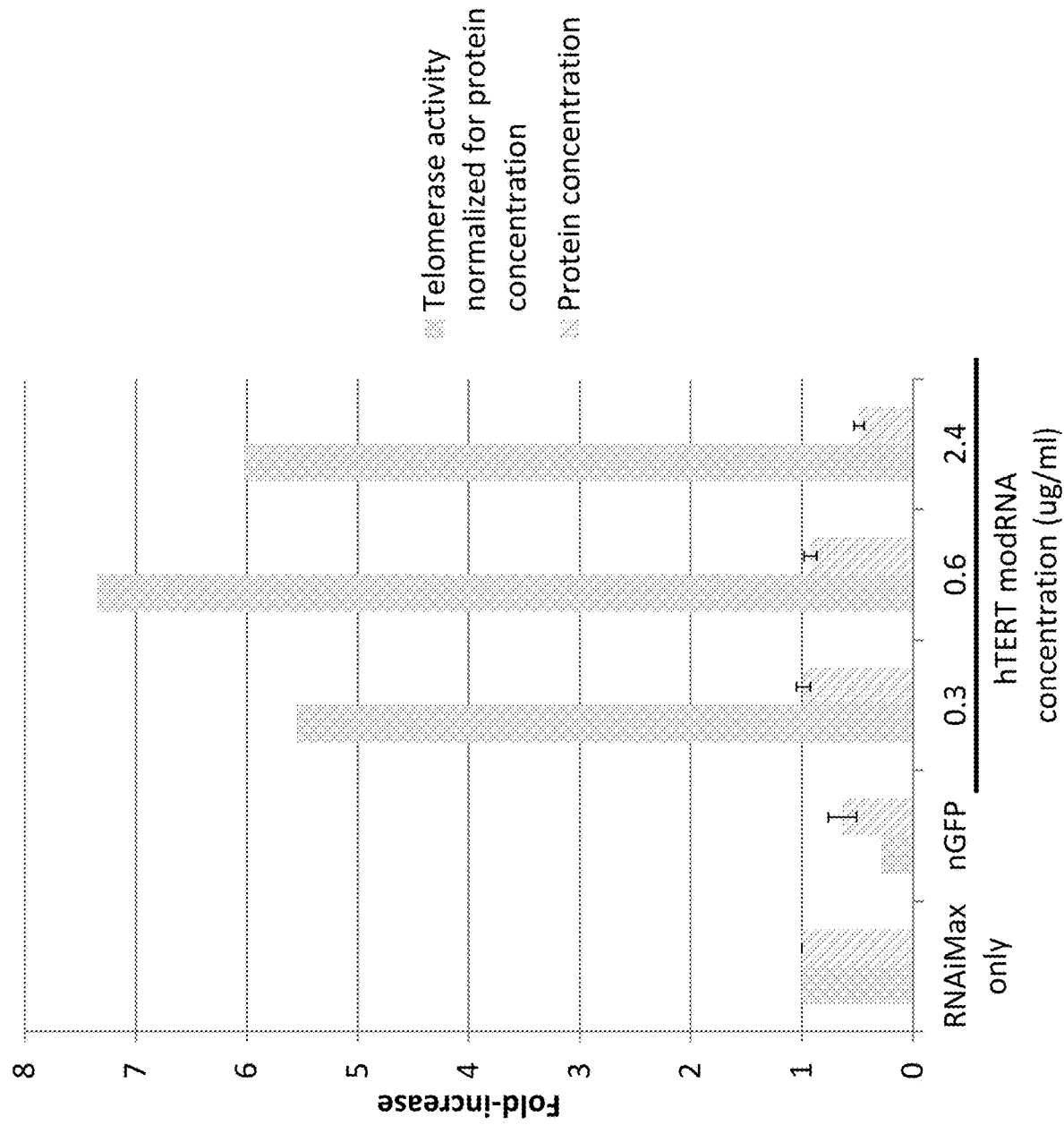
FIG. 7. Dose-response of telomerase activity.

To form functional telomerase, TERT must fold properly and form a complex with at least TERC. Telomerase is also heavily regulated post-translationally, including by cytoplasmic localization and inhibitory phosphorylation. Cifuentes-Rojas and Shippen (2012) *Mutat. Res.* 730:20-27; doi:10.1016/j.mrfmmm.2011.10.003. Indeed not all cells expressing TERT are able to maintain telomeres. Counter et al. (1998) *Proc. Natl. Acad. Sci. U.S.A.* 95:14723-14728. Delivery of TERT modRNA increased telomerase activity in a dose-dependent manner up to a maximum at a concentration of approximately 0.6 ug/ml (see FIG. 7), and a concentration of 1 ug/ml was used for subsequent experiments. Telomerase activity levels increased rapidly but returned to baseline levels within approximately 48 hours, and CI TERT modRNA caused no change in telomerase activity (FIG. 1D). Telomerase activity was measured by qPCR-based TRAPeze® RT assay (n=3).

Since post-translational regulation of TERT is mediated in part by cytoplasmic sequestration in a cell cycle-dependent manner, the subcellular localization of TERT in treated and untreated cells was also investigated. Cifuentes-Rojas et al. (2011) *Mutat. Res. doi:*10.1016/j.mrfmmm.2011.10.003. Consistent with the Western blot results, immunocytochemistry showed abundant, though possibly inhibited, protein recognized by TERT antibody in untreated MRC-5 cells, making it difficult to distinguish endogenous from exogenous TERT (data not shown).

Cells within approximately 10 population doublings (PD) of the onset of replicative senescence were used to measure the effect of TERT modRNA treatment on telomere length and replicative capacity. The decision to use such cells was based on at least two factors. First, cells at this stage have relatively short telomeres, and since telomerase preferentially extends short telomeres, including in MRC-5 cells, treatment of cells at this stage should result in a larger, more easily measured effect. Britt-Compton et al. (2009) *FEBS Lett.* 583:3076-3080. Second, by treating cells at this stage, the amount of time required to determine whether the treatment increased replicative capacity is reduced. Under the instant conditions, replicative senescence begins approximately 50 PD after receipt of MRC-5 cells from the supplier (see Methods for details), and thus it was decided to treat cells at approximately PD 40. MRC-5 cells at this stage have average telomere lengths of approximately 5-7 kb, depending on culture history and PD on receipt from suppliers. Sitte et al. (1998) *Free Radic. Biol. Med.* 24:885-893; MacKenzie et al. (2000) *Exp. Cell Res.* 259:336-350.

Figure 4A:
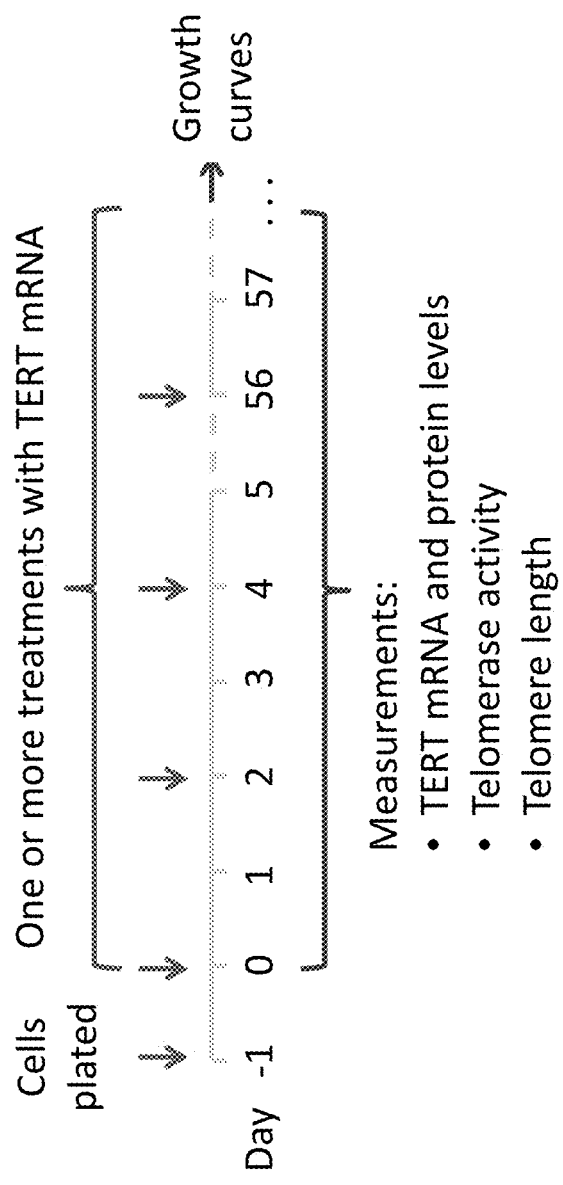
FIGS. 4A-4G. Treatment with TERT modRNA rapidly extends telomeres in MRC-5 cells.
Figure 4B:
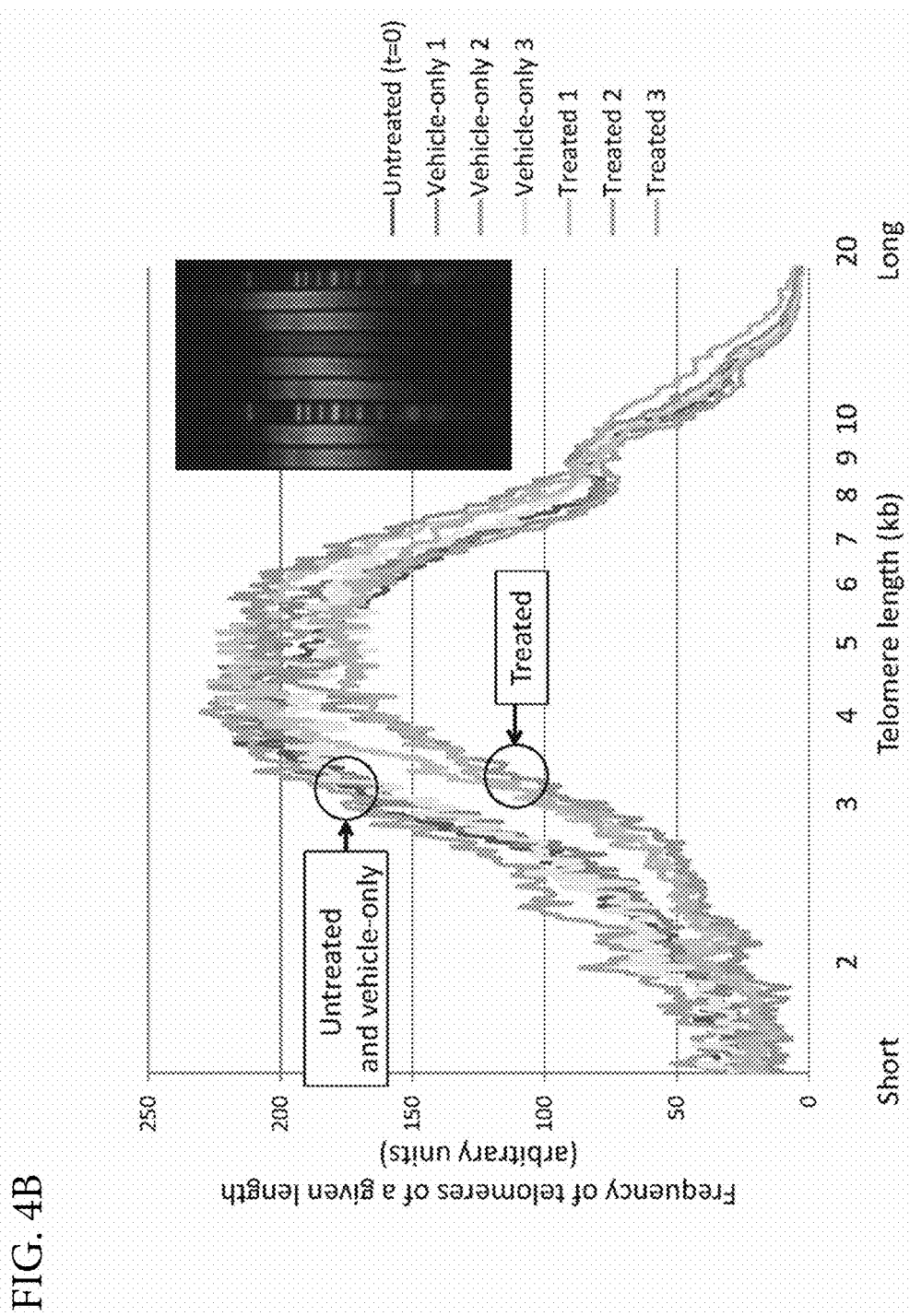
Figure 4C:
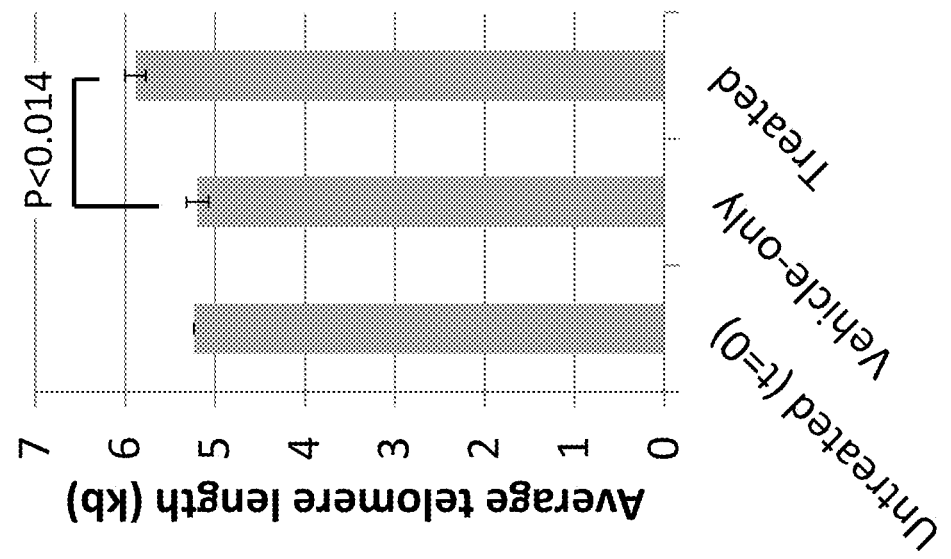
Figure 4D:
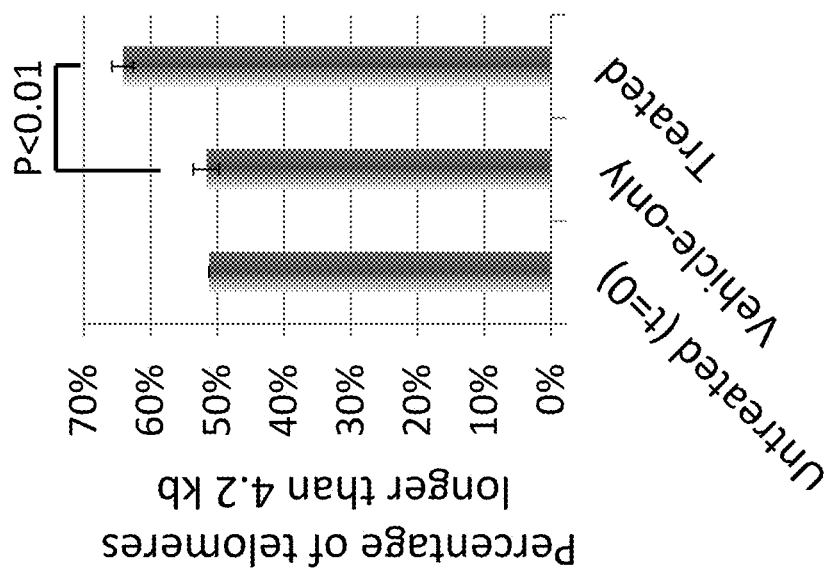

Several considerations were taken into account in designing the treatment schedule (FIG. 4A). Rates of telomere extension obtained using viral transduction of TERT into MRC-5 cells vary but are on the order of about 0.2 kb per division. MacKenzie et al. (2000) *Exp. Cell Res.* 259:336-350. Rates of telomere shortening in MRC-5 cells vary with culture conditions and practices (Sitte et al. (1998) *Free Radic. Biol. Med.* 24:885-893; von Zglinicki et al. (2000) *Free Radic. Biol. Med.* 28:64-74), but are approximately 0.1 kb per PD in ambient oxygen (Sitte et al. (1998) *Free Radic. Biol. Med.* 24:885-893). Cells were cultured in 5% oxygen, as MRC-5 cell telomeres shorten more slowly under less oxidative conditions. von Zglinicki et al. (2000) *Free Radic. Biol. Med.* 28:64-74. The PD time in PD 40 MRC-5 cells was found to be approximately 33 hours. Given these data, it might be expected that multiple treatments would be required in order to detect telomere extension within the resolution of the chosen methods of telomere length measurement, telomere restriction fragment (TRF) analysis and quantitative fluorescence in situ hybridization (Q-FISH). The interval between treatments was chosen to be 48 hours since it was found that telomerase activity levels returned to baseline levels by this time after a single treatment.

Figure 4E:
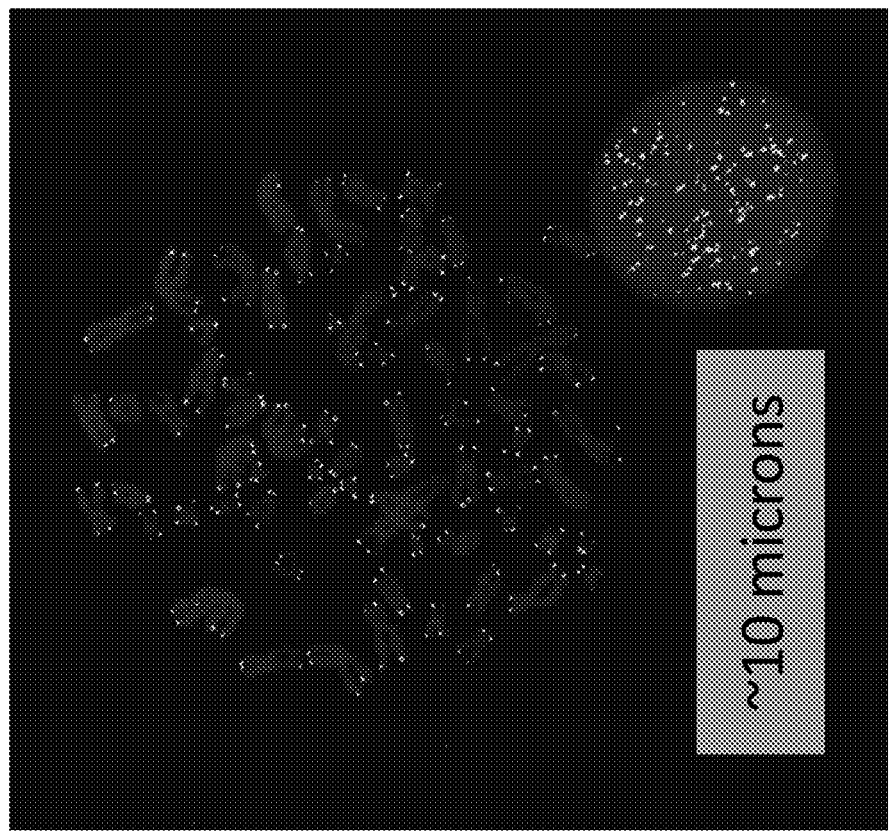

As shown in FIGS. 3B-3D, treatment of MRC-5 cells with hTERT modRNA results in a significant increase in telomere length in these cells compared to cells that are either untreated or treated with the delivery vehicle only. Fluorescence micrographs of metaphase MRC-5 cells following treatment shows the location of a telomere probe on the chromosomes in these cells (FIG. 4E).

Figure 4F:
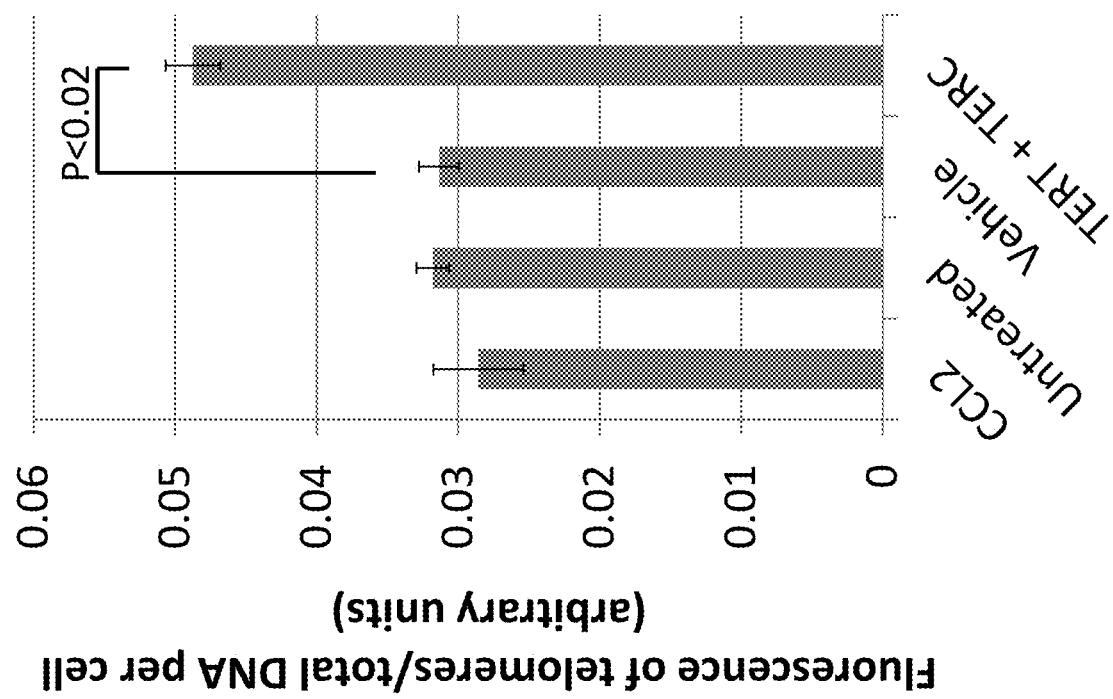
Figure 4G:
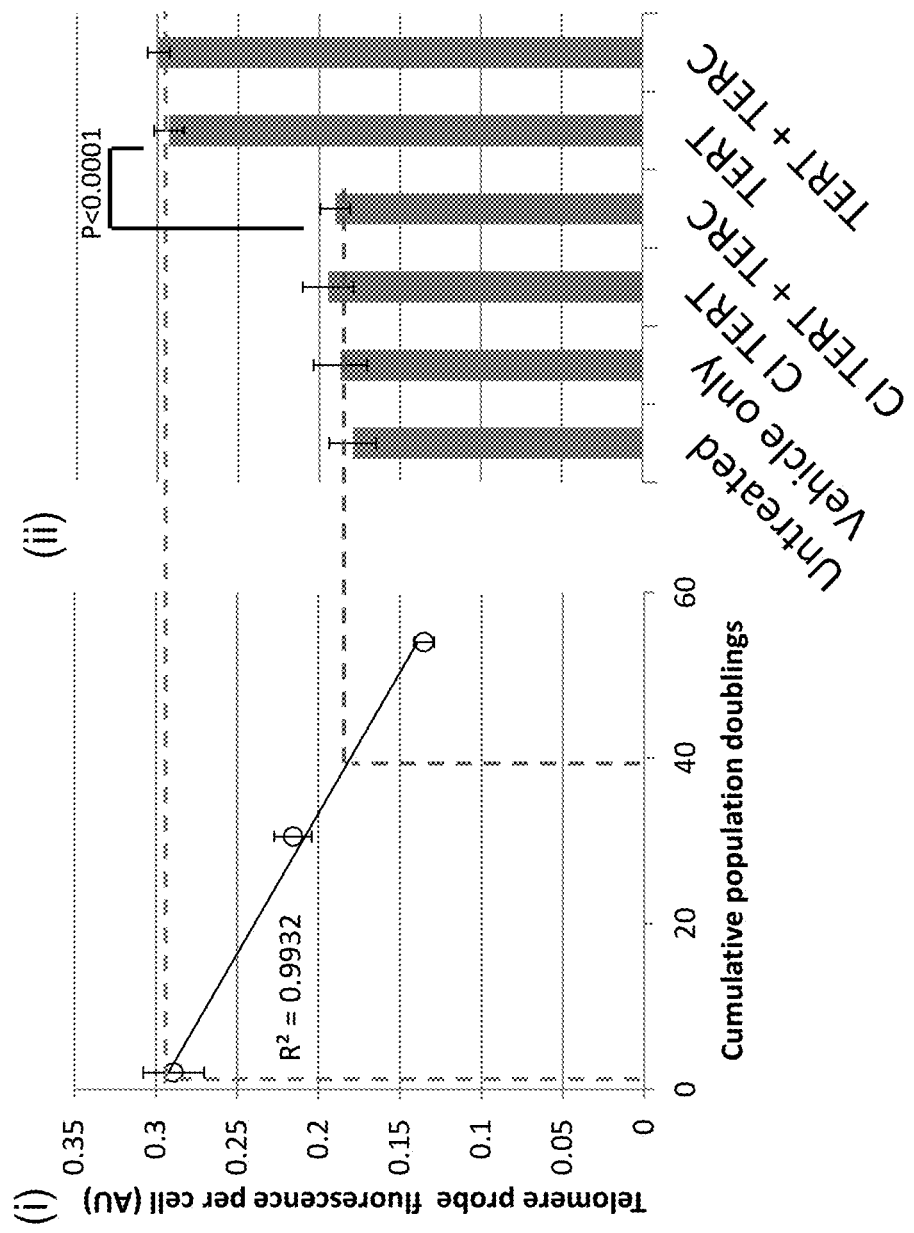

The effect of the treatment on telomere length was also measured by quantitative fluorescence in situ hybridization (Q-FISH) (FIG. 4F), because this technique provides relatively high resolution (0.3 kb) and because the fluorescence of Q-FISH telomere probes is directly proportional to telomere length. Lansdorp et al. (1996) *Hum. Mol. Genet.* 5:685-691; Martens et al. (1998) *Nat. Genet.* 18:76-80. Because replicative capacity is the functional parameter of most interest in increasing as a result of extending telomeres, a standard curve relating population doubling number of MRC-5 cells to telomere length as measured using Q-FISH was constructed (FIG. 4G(i)). After three treatments of PD 40 MRC-5 with TERT mRNA at 48 hour intervals, average total telomere length per cell increased by 56+/−5% (n=15 cells for each of two biological replicates for each treatment; error bars represent s.e.m.). Telomere lengths in treated PD 40 cells were similar to those of untreated PD 3 cells (FIG. 4G(ii)) (upper dashed line), and thus the treatment extended telomeres by the amount by which telomere shorten in these cells over 37 PD. In this number of PD under standard culture conditions, MRC-5 telomeres shorten by over >1 kb. Sitte et al. (1998) *Free Radic. Biol. Med.* 24:885-893. Consistent with this, the observed increase in telomere length of 56% corresponds to an increase in average telomere length of approximately 0.6-2.5 kb, based on the fact that PD 40 MRC-5 cells have average telomere lengths of approximately 5-7 kb as measured using TRF (Sitte et al. (1998) *Free Radic. Biol. Med.* 24:885-893; MacKenzie et al. (2000) *Exp. Cell Res.* 259:336-350), which overestimates telomere length by approximately 2.5-4 kb, and thus actual average telomere lengths in PD 40 MRC-5 cells are in the range of 1-4.5 kb. Aubert et al. (2012) *Mutat. Res.* 730:59-67. Since the treatment lasted a total of 144 hours, and the population doubling time of the cells was approximately 33 h. during this time, the cells underwent approximately 4-5 PD. Thus, the rate of telomere extension was approximately 0.1-0.6 kb per PD, the upper range of which approaches the maximum rates ever reported following viral transduction of DNA encoding TERT, and the lower range of which is comparable to typical rates seen using viral delivery. As expected, the untreated cells have telomere lengths equivalent to PD 40 cells during generation of the standard curve (lower dashed line in FIG. 4G).

Figure 5A:
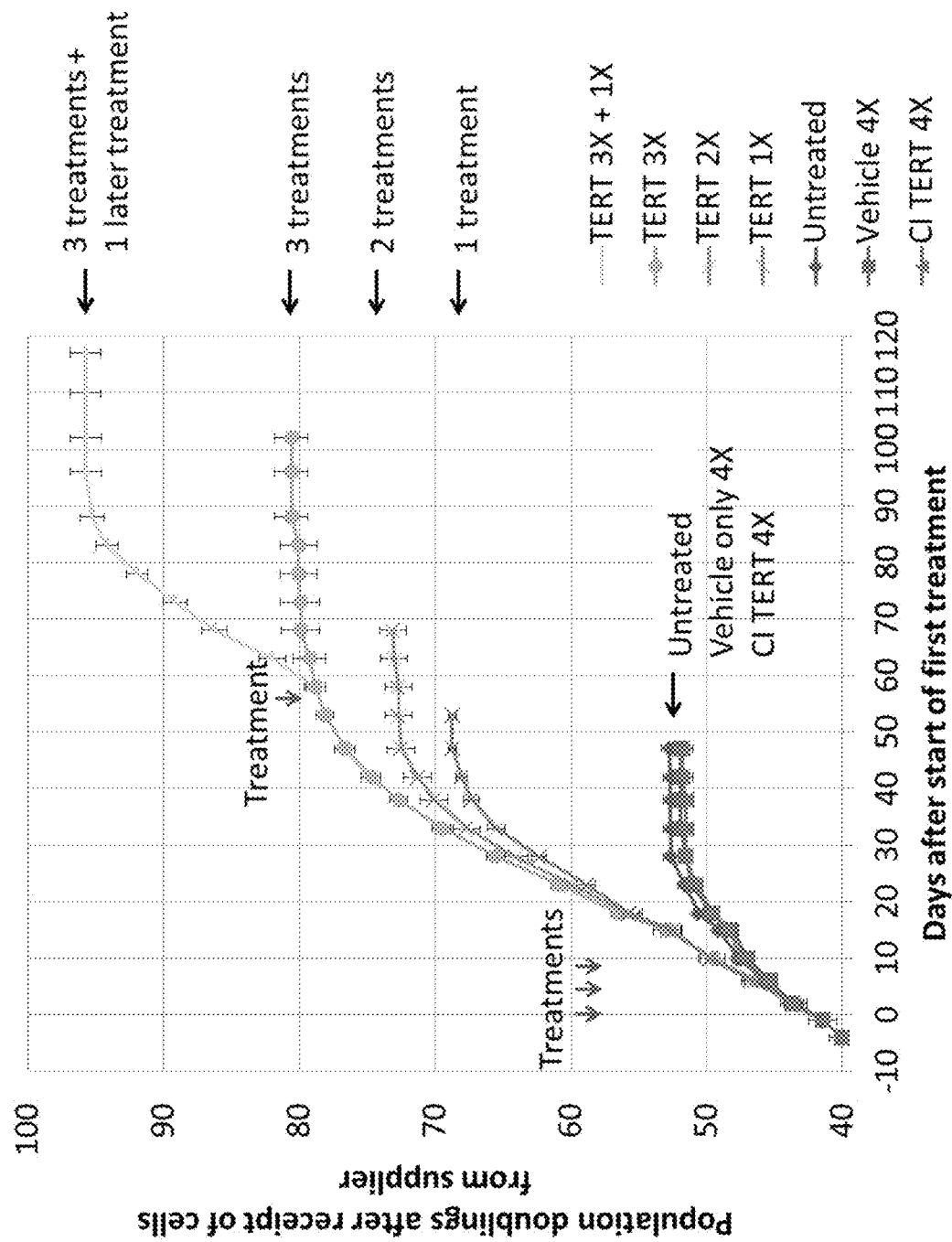
FIGS. 5A-5C. Brief treatment with TERT modRNA increases replicative capacity of, but does not immortalize, MRC-5 cells in a dose-dependent manner.
Figure 5B:
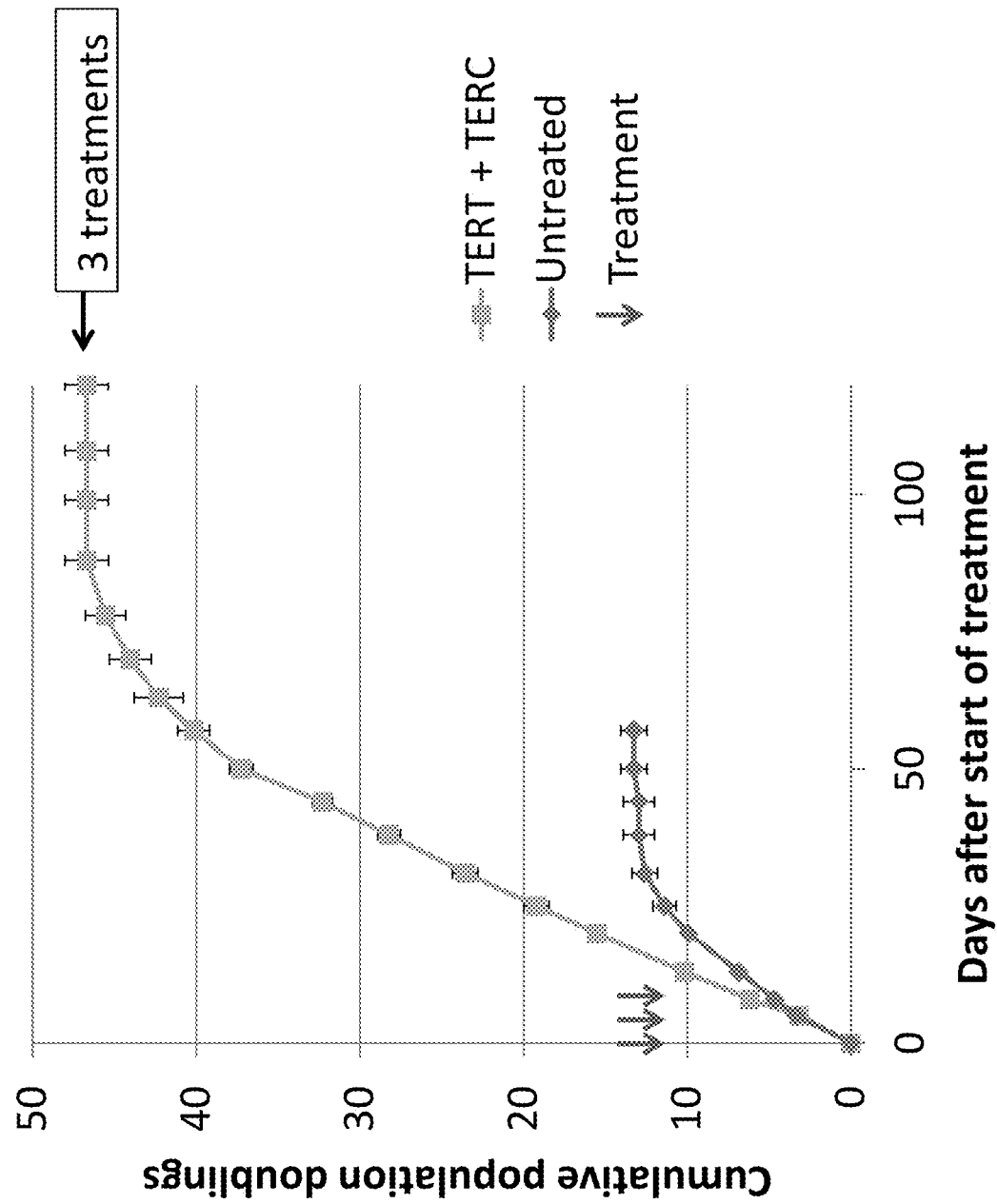
Figure 5C:
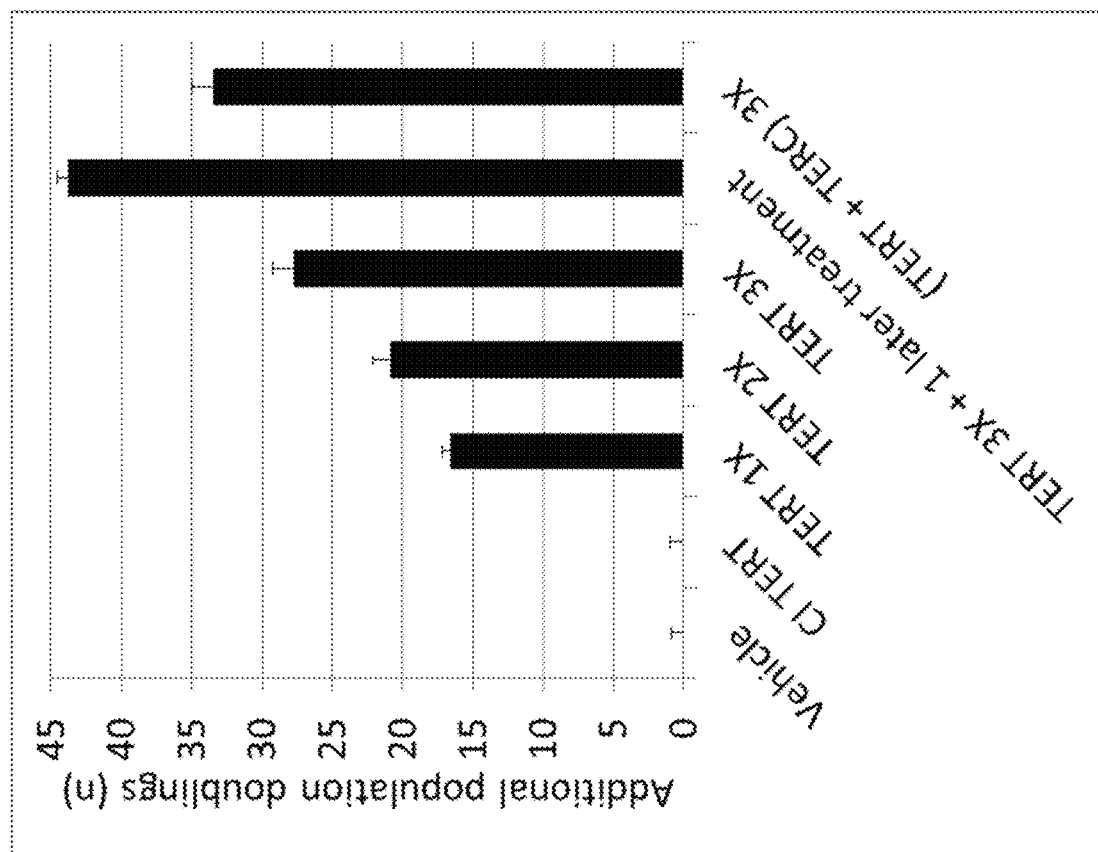

Next, the effect of TERT mRNA treatment on cell replicative capacity was examined. As expected, untreated and vehicle only-treated cells senesced within the normal range of 50-60 PD (FIG. 5A). In striking contrast, cells treated with TERT mRNA continued to proliferate beyond the PD at which the control populations reached replicative senescence in a dose-dependent fashion, with each additional treatment conferring significantly more extra PD.

Three treatments with TERT mRNA resulted in an increase in replicative capacity of 28+/−1.5 PD. This result is consistent with an estimate that telomeres were extended by >1 kb, as MRC-5 telomeres shorten by approximately 0.1 kb per PD (Sitte et al. (1998) *Free Radic. Biol. Med.* 24:885-893) in ambient (20%) oxygen, and the treated cells were cultured in 5% oxygen, in which telomeres shorten more slowly. The observed increase in replicative capacity of treated cells of 28 PD is equivalent to the loss of replicative capacity that occurs in normal fibroblasts over more than a decade of normal human aging. Takubo et al. (2010) *Geriatr Gerontol Int.* 10 Suppl 1:S197-206; doi: 10.1111/j.1447-0594.2010.00605.x.; Allsopp, R. C. et al. (1992) *Proc. Natl. Acad. Sci. U.S.A.* 89:10114-10118.

Importantly for therapeutic applications, all of the treated cells studied to date eventually senesced, and indeed senesced in fewer PD than untreated cells with equivalent telomere lengths, as might be expected since the treated cells have undergone dozens of additional PD, compared to the untreated cells with similar-length telomeres, in which to accumulate non-telomeric DNA damage or other damage that might affect rates of telomere shortening or otherwise support induction of replicative senescence.

Figure 8A:
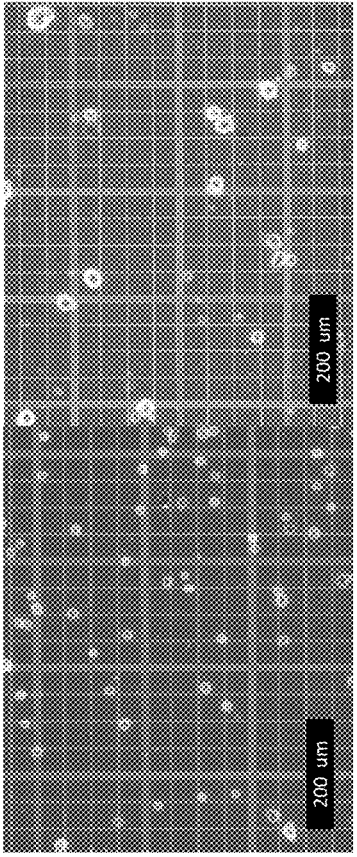
FIGS. 8A-8B. TERT modRNA treatment delays cell swelling in MRC-5 cells.
Figure 8B:
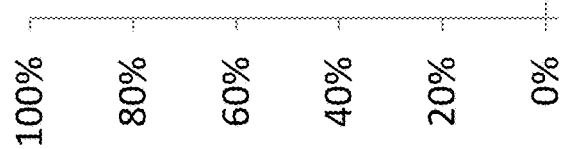

As MRC-5 cells approached and entered replicative senescence, they tended to swell to several times the diameter of early passages (FIG. 8A). As with replicative senescence, this transition was delayed in cells treated with TERT modRNA, but not in cells receiving CI TERT modRNA or vehicle only (FIG. 8B).

Consistent with the finding that CI TERT modRNA caused no increase in telomerase activity (FIG. 1D), CI TERT modRNA treatment did not change telomere length distribution relative to untreated cells, and nor did CI TERT modRNA increase replicative capacity, despite causing an increase in TERT protein level equivalent to that caused by TERT modRNA (FIG. 1C). Since the only difference between TERT and CI TERT is a single-residue substitution which abrogates the ability of CI TERT to transfer nucleotides to telomeres, these results strongly support the hypothesis that the increase in telomere length and replicative capacity observed in cells treated with TERT modRNA is due to bona fide telomere extension in at least some of the treated cells, rather than selection of a pre-existing subpopulation of cells with longer telomeres.

The results of this example show that delivery of TERT modRNA to human cells transiently elevates telomerase activity, rapidly extends telomeres, and increases replicative capacity by a finite, and thus potentially safe, amount. Purified biomimetic modRNA is also hypo-immunogenic. Karikó et al. (2011) *Nucleic Acids Res.* 39:e142; doi: 10.1093/nar/gkr695. Thus modRNA delivery meets several important criteria for a therapeutic telomere extension treatment, and also has promise with regard to other criteria including specificity, targeted delivery, and ability to overcome post-translational regulation. Regarding specificity, TERT overexpression may also affect other genes such as Wnt (Park et al. (2009) *Nature* 460:66-72), but such effects may be avoided by delivering modRNA encoding a TERT mutated at binding sites of factors that mediate any such non-specific effects. Regarding delivery, the recent discovery that in humans modRNA is transported in exosomes between cells via blood and other body fluids enables exosome-based modRNA delivery for telomere extension and other applications. Lakhal and Wood (2011) *Bioessays* 33:737-741. Exosomes have been used successfully to deliver biomimetic modRNA to cells in vitro (data not shown). Regarding post-translational regulation, cell cycle-dependent and independent inhibitory post-translational regulation of TERT may be avoided by delivering modRNA encoding TERT mutated at one or more known sites that mediate those activities, such as the nuclear export sequence, or by co-delivering modRNA encoding other members of the telomerase or telomere complexes. These approaches enable telomere extension even in slowly- or non-dividing cells, making TERT modRNA treatment appropriate for quiescent or slow-dividing stem and progenitor cell populations. modRNA-based telomere extension thus finds immediate use in increasing the replicative capacity of cells for research, and additionally for cell therapies, bioengineering applications, and in vivo treatments that address diseases and conditions of inadequate telomere maintenance.

In summary, modRNA encoding human telomerase reverse transcriptase (TERT) was delivered to MRC-5 human lung fibroblasts three times over 96 hours. Telomeres in treated cells were extended by >1 kb, an amount by which fibroblast telomeres shorten over more than a decade of aging in humans on average. Takubo et al. (2010) *Geriatr Gerontol Int.* 10 Suppl 1:S197-206; doi: 10.1111/j.1447-0594.2010.00605.x. Telomerase activity returned to pre-treatment levels within 48 hours and the onset of replicative senescence in the treated cells was delayed by approximately 30 population doublings, in a dose-dependent manner. Thus delivery of telomerase RNA containing modified nucleosides to cells allows for the rapid and hypoimmunogenic or nonimmunogenic and RNA is a useful approach to telomere extension for diverse applications.

Methods modRNA template generation and synthesis. The wild type (WT) human TERT open reading frame (ORF) used to generate the DNA templates for modRNA synthesis is identical to the NCBI human TERT transcript variant 1 reference sequence NM_198253.2, and was generated by making the modification G516D to the ORF of the pBABE-neo-hTERT plasmid (Addgene plasmid 1774). Residue 516 is in the QFP motif of the N-terminal extension of TERT, a motif associated with multimerization and RNA binding of TERT. The catalytically inactive TERT (CI TERT) mutant was generated from the WT TERT sequence by introducing the mutation D712A. The WT and CI, TERT ORFs were inserted into the MCS of a starting plasmid containing the T7 promoter, the 5' UTR of human beta globin (hBB), the MCS, the 3' UTR of hBB, a 151 bp poly-A sequence, and a restriction site for linearization with class IIs enzyme following the poly-A sequence. The resulting intermediate plasmid was sequenced in at least quadruplicate to ensure fidelity, linearized, and transcribed to capped RNA using the RNA polymerase from the MEGAscript T7 Kit (Ambion, Austin, Texas) and a custom nucleotide mix of canonical and non-canonical nucleotides (TriLink BioTechnologies) in which the final nucleotide concentrations per 40 ul IVT reaction were 7.5 mM for each of adenosine-5'-triphosphate (ATP), 5-methylcytidine-5'-triphosphate (m5C), and pseudouridine-5'-triphosphate (Ψ), 1.5 mM for guanosine-5'-triphosphate (GTP), and 6 mM for the cap analog (ARCA, NEB), or a molar ratio of ATP:m5C:Ψ:GTP:ARCA of 1:1:1:0.2:0.8. To further decrease potential immunogenicity of the mRNA related to the 5'-3P-bearing fraction (~20% of total) the IVT products were treated with phosphatase (Antarctic Phosphatase, NEB). The size and integrity of the modRNA products was verified using denaturing agarose gel electrophoresis.

Cells and cell culture. MRC-5 human fetal lung fibroblasts (ATCC CCL-171) were received from ATCC at passage 14, the current passage number of their distribution inventory. Since ATCC does not indicate the PD number, the PD values cited herein refer to the number of PD after receipt of cells from ATCC, defined here as PD 0. To shorten their telomeres in preparation for telomere extension experiments, cells were cultured using ATCC guidelines in DMEM with 10% FBS, in ambient oxygen and 5% $CO_2$. Telomere extension treatment began at approximately PD 40 after receipt of cells from ATCC. At least 48 hours before the start of modRNA treatment cells were transferred to 5% oxygen and DMEM medium containing 20% FBS and penicillin-streptomycin. Cells were treated at least 24 hours after plating and 24 hours before trypsinization.

modRNA transfection. Cells were transfected with 0.4 nM TERT modRNA and 2.0 nM TERC RNA unless otherwise specified, using Lipofectamine RNAiMax (Invitrogen), a cationic lipid, in Opti-MEM Reduced Serum Media (Invitrogen) for 4-5 hours, after which they were returned to normal medium.

Telomerase activity measurement. 24 hours after the start of transfection period, cells were washed with PBS, trypsinized, pelleted at 500 g for 5 min. and washed with PBS, repelleted, and then lysed following the instructions in the TRAPeze RT kit (Millipore). The reverse transcription and qPCR steps were carried out in a Roche LightCycler 480 II and an ABI 7900 HT. Telomerase activity of samples was always compared to the reference standard provided with the kit, as we found that fold-increase was prone to be highly variable, probably due to the low telomerase activity in MRC-5 cells.

Immunocytochemistry. 24 hours after the start of transfection period, cells were washed with PBS, fixed in 2% paraformaldehyde for 20 minutes, washed three times with PBS, blocked in PBS containing 7.5% BSA and 0.1% Triton X-100 for 1 hour, washed three times, incubated overnight at 4oC on a rocker in anti-TERT antibody (ABCAM 32020 at 1:50 or Rockland 600-401-252S at 1:500) in PBS with 5% BSA, washed three times, incubated for one hour in secondary antibody, washed two times then two more times on a shaker for 3 minutes each time, then incubated in 0.1 ug/ml DAPI for 3 minutes, and washed four times in PBS.

Flow cytometry. Cells treated with 0.5-1.5 ug/ml of TERT modRNA and controls were trypsinized 22 h. after start of transfection, washed, fixed in 2% paraformaldehyde, permeabilized in 7.5% BSA with 0.1% Triton X-100 for 20 min., washed three times in PBS, blocked in 7.4% BSA for 1 h, incubated in anti-TERT antibody (ABCAM 32020 at 1:50) in PBS with 5% BSA, washed three times, incubated in secondary antibody (1:200) in PBS, then washed three times and resuspended in FACS buffer and analyzed on a Accuri C6 Flow Cytometer (Becton Dickinson). Mean fluorescence intensity was calculated as the average fluorescence of all cells in treated and control samples. Data were analyzed using CFlow Plus software.

RT-PCR Total RNA was harvested using the RNeasy Mini kit (Qiagen) and converted to cDNA using the High-Capacity RNA-to-cDNA Kit (Invitrogen). cDNA was amplified using PCR with the following primers:

| | | |
|---|---|---|
| hTERT-F: | 5'-GCCCTCAGACTTCAAGACCA | (SEQ ID NO: 1) |
| 3'-hBB-R: | 5'-AGGCAGAATCCAGATGCTCA | (SEQ ID NO: 2) |
| GAPDH-F: | 5'-GTGGACCTGACCTGCCGTCT | (SEQ ID NO: 3) |
| GAPDH-R: | 5'-GGAGGAGTGGGTGTCGCTGT | (SEQ ID NO: 4) |

Western blot. Protein was harvested by washing cells once with PBS and then lysing cells in RIPA buffer. Protein was run on NuPAGE Novex Tris-Acetate Gels, transferred to PVDF membrane for 2 h. at 35 V, then hybridized to anti-alpha tubulin (Sigma at 1:10,000) and anti-TERT antibody (ABCAM 32020 at 1:1000 or Rockland 600-401-252S at 1:500) and anti-overnight at 4° C. Secondary detection was performed using infrared (680 nm and 800 nm) antibodies (LI-COR) and the Odyssey imager (LI-COR). Images were analyzed using ImageJ.

Q-FISH. Cells were incubated in 0.1 ug/ml colcemid for 4 hours before fixation and preparation of metaphase spreads following the procedure of Lansdorp et al. 41 Slides were then stained using the Telomere PNA FISH Kit/FITC kit (Dako, Denmark), substituting AlexaFluor 555-labeled telomere probe (Bio-Synthesis, USA) for the kit probe. Each cell was imaged on a DeltaVision (Applied Precision, Inc., Washington) microscope using SoftWoRx software using either a 60× or 100× oil objective at 0.2 micron intervals over a range of 3 microns using a motorized stage, and custom software was used to identify the image in which each telomere spot was in focus and integrate its intensity in that in-focus image. Temporal variation in illumination intensity was compensated for using the DeltaVision photosensor which recorded the illumination intensity of each image, and variation in spatial intensity and CCD dark current and read error was compensated for by acquiring flat field images and dark field images, respectively. At least 15 metaphase cells contributed to each replicate and each sample was measured in at least duplicate over at least two separate experiments.

Growth curves. Cells were harvested and counted on a hemocytometer as an automated counter was unable to accurately count the cells when the population became heterogeneous with respect to diameter as the population entered replicative senescence. Images were acquired to allow measurement of cell diameters. PD were calculated as the log 2 of the ratio of cell numbers at end and start of each culture period between passages.

Statistics. Statistical analysis was performed using Microsoft Excel. Error bars represent the mean±s.e.m. Telomere lengths were compared using T-tests with $P<0.05$ (two-tailed) considered to be statistically significant.

Example 2

Effects of TERT ModRNA Treatment on Human Endothelial Cells

Figure 9:
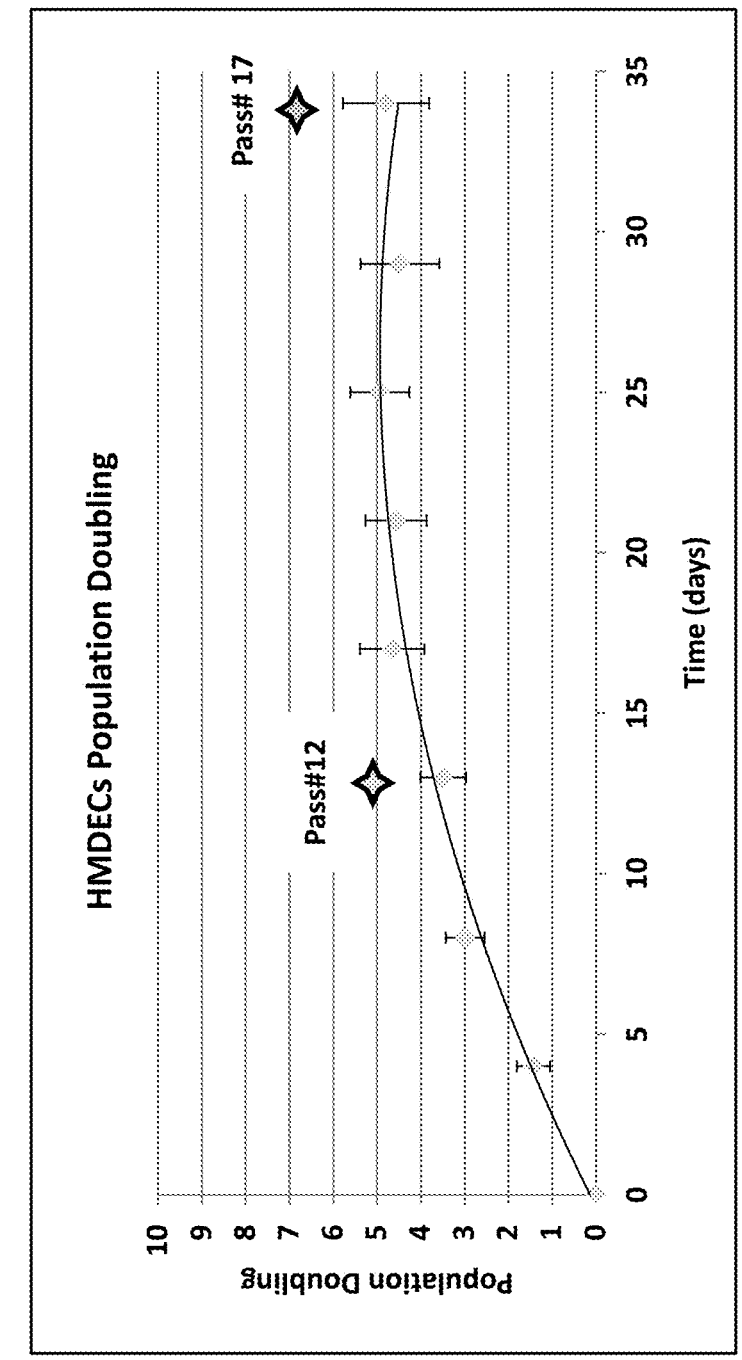
FIG. 9. Growth curve for human microvascular dermal endothelial cells (HMDECs).
Figure 10:
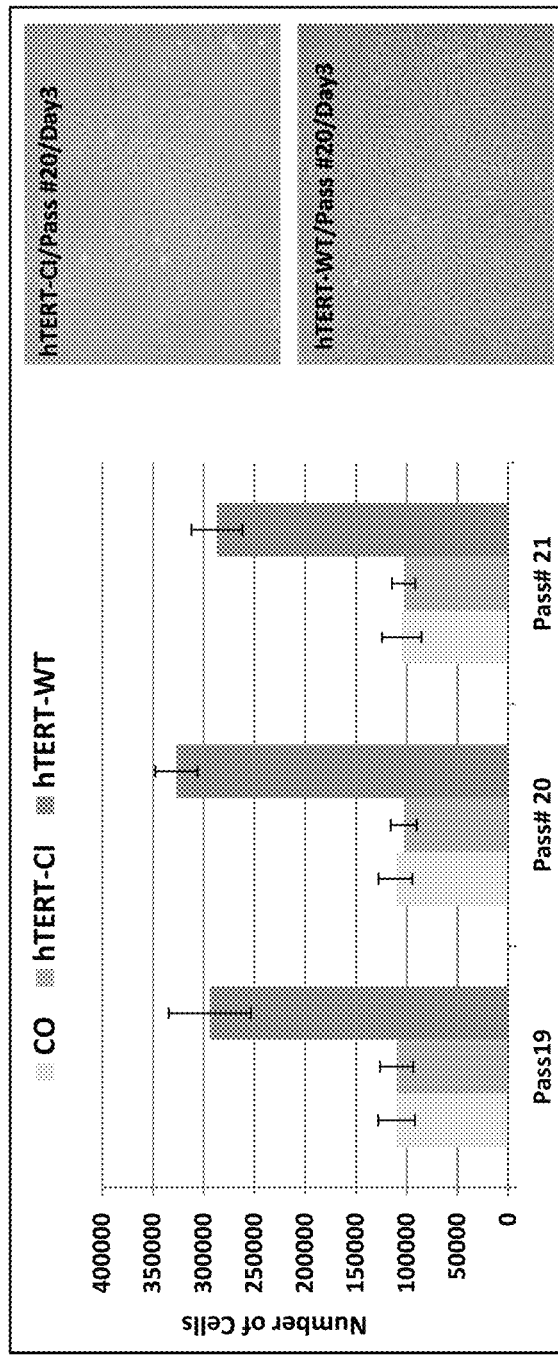
FIG. 10. Effect of TERT modRNA treatment on cell number in HMDECs. CO: control treatment; hTERT-CI: catalytically-inactive hTERT; hTERT-WT: wild-type hTERT.

The effects of TERT modRNA treatment is not limited to fibroblast cells. As shown in FIG. 9, human microvascular dermal endothelial cells ("HMDEC") display typical doubling curves, with early onset of senescence at approximately passage #12 and with cells completely senescent at passage #17. As shown in FIG. 10, treatment of these cells at passage #18 with wild-type hTERT modRNA (right bar in each series) results in the reversal of senescence, whereas control treatment (left bar in each series), or treatment with mutant hTERT modRNA (middle bar in each series), had no effect on cellular senescence.

Figure 11:
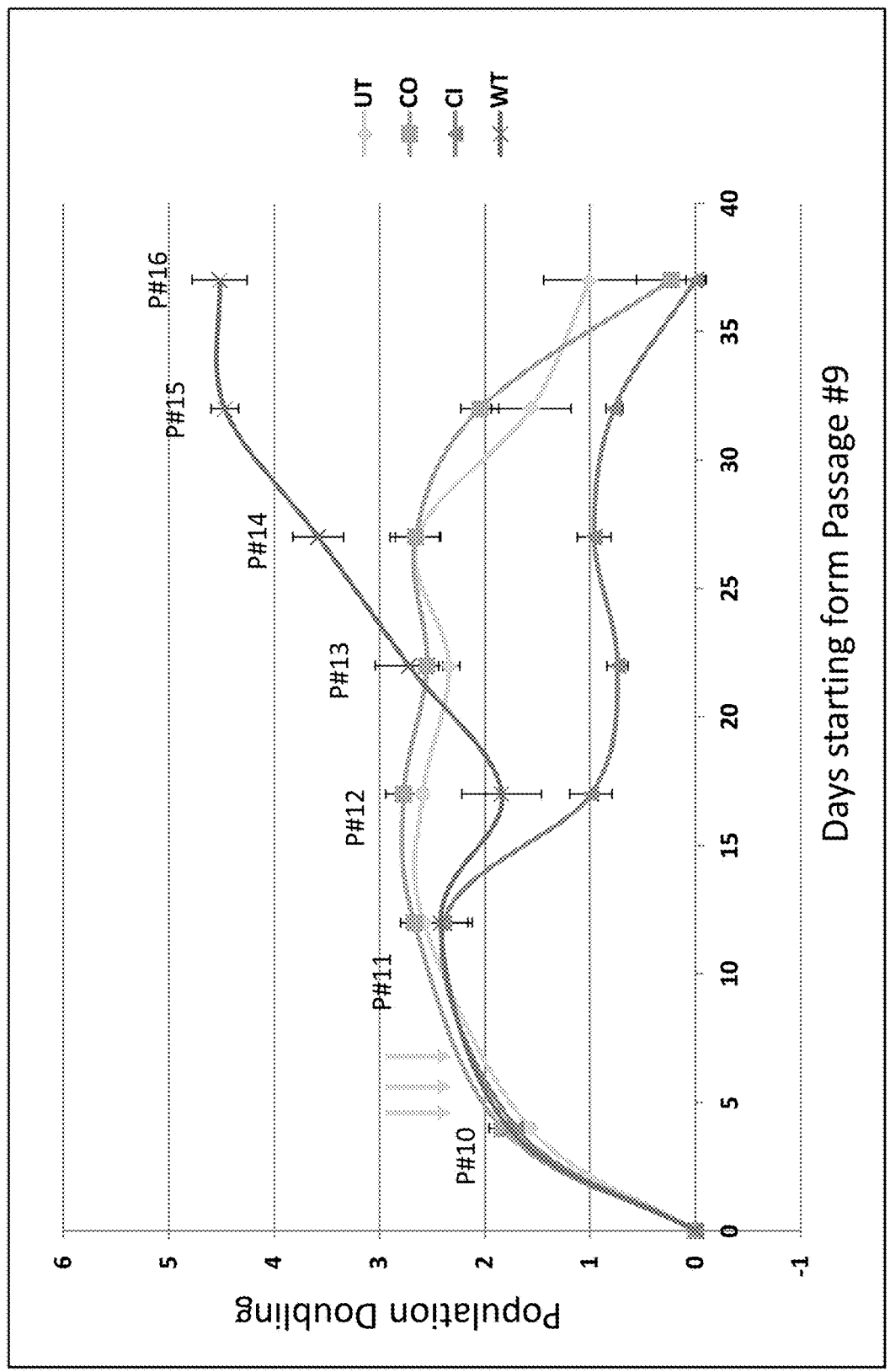
FIG. 11. Effect of TERT modRNA treatment on growth of HMDECs. UT: untreated; CO: control treatment; CI: catalytically-inactive hTERT; WT: wild-type hTERT.

FIG. 11 demonstrates the effects of various treatments on the growth of HMDECs. Specifically, cells treated three times with wild-type TERT modRNA (WT) between passage #10 and passage #11 continued to grow, whereas untreated cells (UT), cells treated with carrier only (CO), and cells treated with a catalytically-inactive TERT (CI) stopped doubling.

Figure 12:
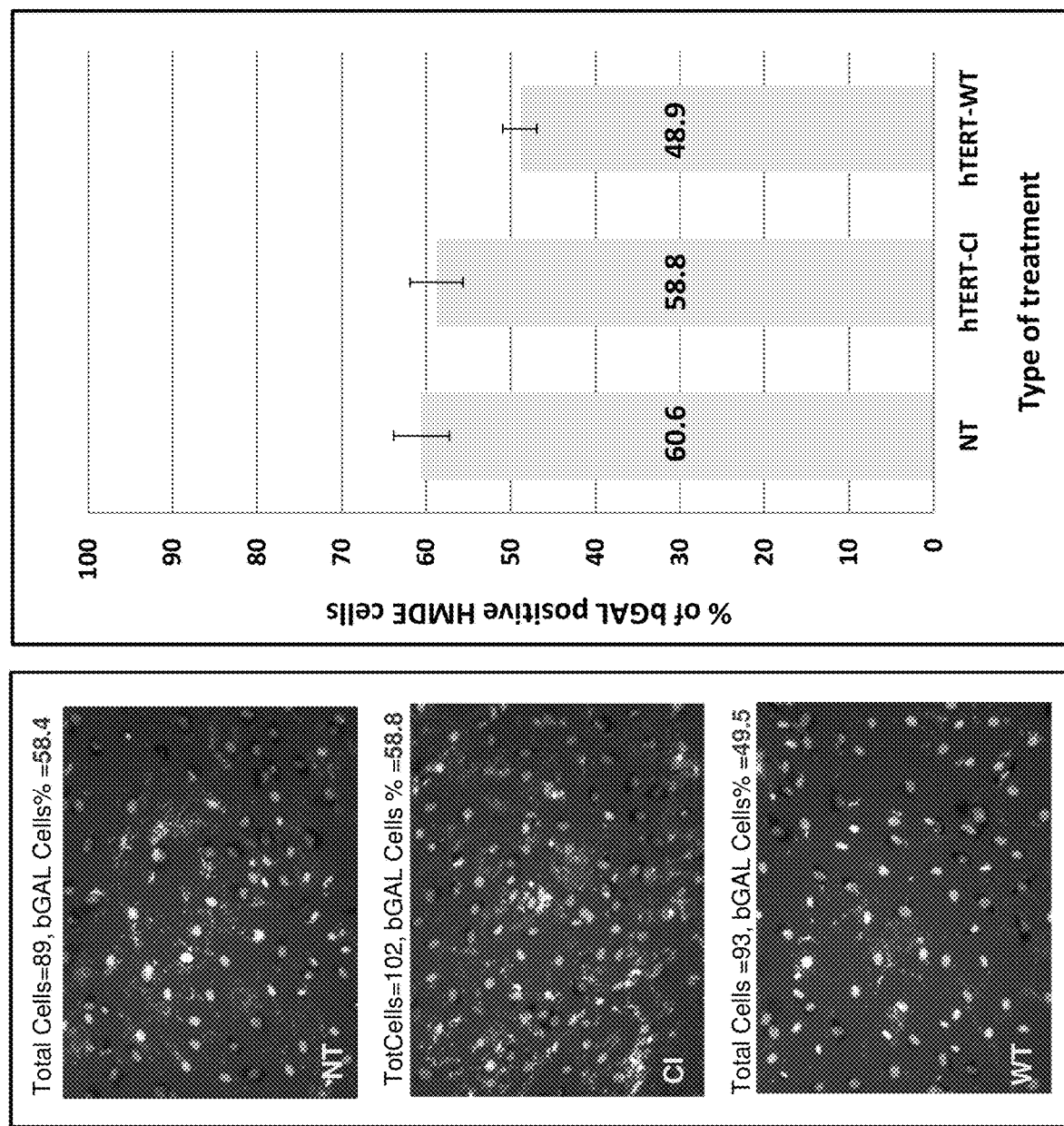
FIG. 12. Effect of TERT modRNA treatment on senescence in HMDECs. NT: untreated; hTERT-CI: catalytically-inactive hTERT; hTERT-WT: wild-type hTERT.

FIG. 12 shows the results of β-galactosidase (bGAL) staining of HMDECs at passage #14 following treatment with WT and CI modRNAs. This staining measures β-galactosidase activity at pH 6, which is a property of senescent cells that is not found in presenescent, quiescent, or immortal cells. See Dimri et al. (1995) *Proc. Nat'l Acad. Sci. USA* 92:9363-7.

Methods

The HMDECs Cumulative Population Doubling Curve was built using a 12-well plate format. Approximately $10^5$ of HMDECs were at each time point replated in triplicates and cell counting was done on day 4 after the previous replating. As shown in FIG. 9, passage #12 was determined as the early onset point of HMDECs senescence.

As shown in FIG. 10, approximately $10^5$ HMDECs were transfected twice every other day with 0.75 mg of modRNAs encoding hTERT-CI, and -WT in present of Carrier Only (CO, RNiMAX) control. Cell counting was done on Passages #19, 20, and 21 each time on day 5 after replating.

For the experiment shown in FIG. 11, in the interval between passage #10 and #11 (and, as noted above, passage #12 corresponds to the early onset of HMDEC senescence), approximately $5\times10^5$ HMDECs per 75 cm³ flask were cultivated on EBM-2 medium supported with EGM-2 MV supplement (both from Lonza, Walkersville, MD USA, catalogue nos. CC-3156 and CC-4176, respectively). Microvascular cells were transfected three times every other day with 5 µg of modRNAs encoding hTERT-WT (WT) and hTERT-CI (CI) in the presence of untreated (UT) and carrier only (CO, RNAiMAX) control flasks. At each time point, $5\times10^5$ cells were plated and, starting from passage #11, a cell count via hemocytometer was done on 5 days after replating. For each time point, each experimental condition was performed in triplicate.

For the experiments shown in FIG. 12, approximately $10^5$ of each NT, hTERT-CI and hTERT-WT HMDECs of passage #14 were treated as described in FIG. 10. The cells were then subjected to senescent cell analysis based on a histochemical stain for β-galactosidase activity at pH 6 using a Senescence Cells Histochemical Staining Kit (Sigma, catalogue no. CS0030). The left side of the slide shows representative images of non-treated (NT) cells and cells treated with hTERT-CI (CI) or hTERT-WT (WT) modRNAs. All images were obtained under identical image-acquisition conditions. Each experimental condition was performed in triplicate, and the percent of cells positive for β-galactosidase activity (as represented in the chart) for each condition was calculated as an average of positive cells in three randomly captured areas.

Example 3

Further Characterization of the Effects of TERT ModRNA Treatment on Human Cells

Figures 13A, 13B, 13C, 13D:
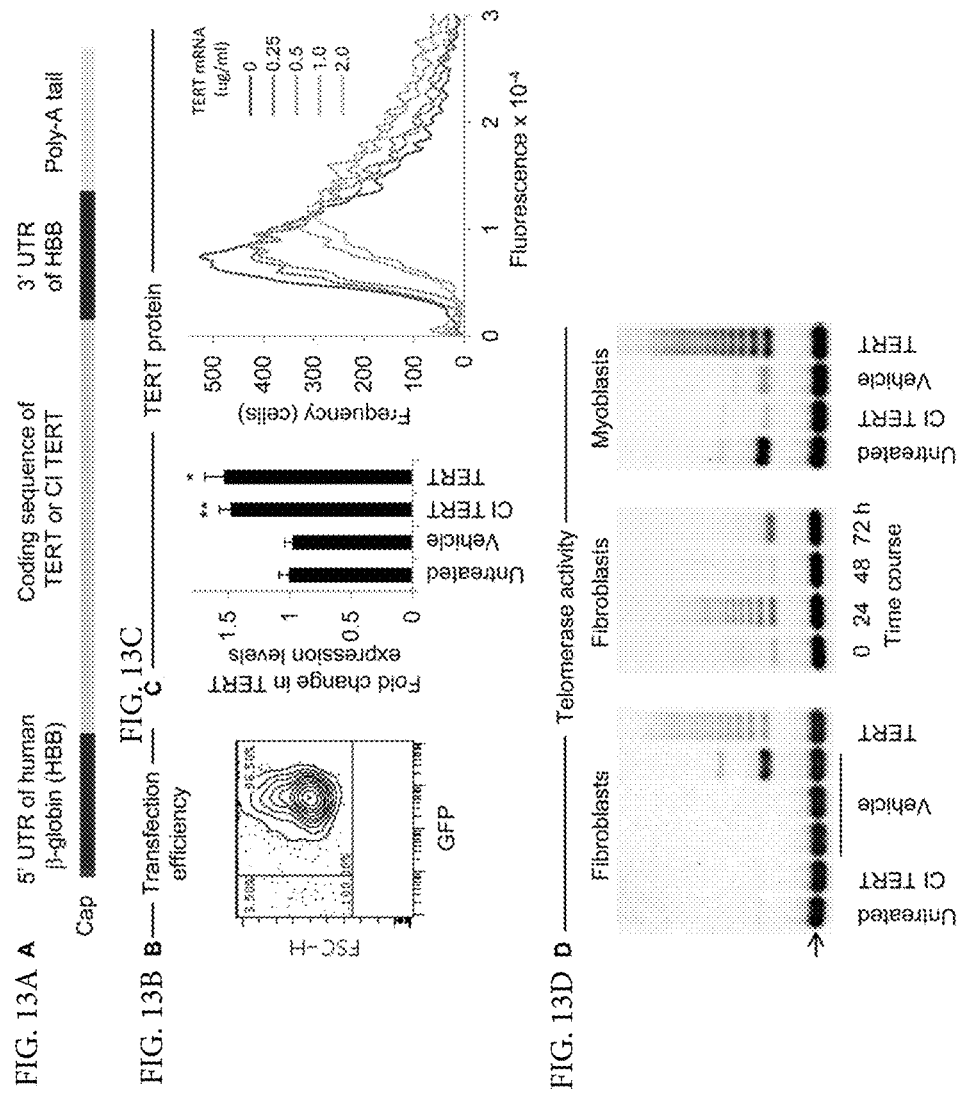
FIGS. 13A-13D. Increases in TERT protein and telomerase activity following modified TERT mRNA delivery.

In this example, the mRNA was transfected via a cationic lipid into primary human fibroblasts and myoblasts (FIG. 13A), cells known to have limited proliferative capacity. Webster and Blau (1990) *Somat Cell Mol Genet.* 16:557-565; Hayflick and Moorhead (1961) *Exp Cell Res.* 25:585-621; Yakubov et al. (2010) *Biochem Biophys Res Commun.* 394:189-193. Transfection efficiency was determined using flow cytometric single cell quantitation of fluorescence following delivery of GFP mRNA, which showed that most cells (>90%) were transfected even at relatively low concentrations of modified mRNA (0.1 µg/ml) (FIG. 13B and FIGS. 16A-16C). Treatment of cells with equal concentrations of exogenous TERT mRNA or mRNA encoding a catalytically inactive (CI) form of TERT resulted in internalization of similar amounts of mRNA (FIG. 16D), as measured by RT-qPCR 24 h after the first treatment. CI TERT has a substitution mutation at one of the triad of metal-coordinating aspartates at the catalytic site of the reverse transcriptase domain of TERT. As a result, CI TERT cannot add nucleotides to telomeres, yet remains structurally intact, able to bind template DNA, and exhibits stability comparable to wild type TERT in reticulocyte lysates. Wyatt (2009) *Structure-Function Analysis of the Human Telomerase Reverse Transcriptase*. Neither TERT nor CI TERT mRNA treatment affected levels of endogenous TERT mRNA relative to untreated cells as measured by RT-qPCR (FIG. 16E). Transfection with 1 μg/ml of either TERT or CI TERT mRNA resulted in equivalent 50% increases (P<0.05 and <0.01, respectively) in the amount of TERT protein in fibroblasts (FIG. 13C, left panel). Wick et al. (1999) *Gene.* 232:97-106; Ahmed et al. (2008) *J Cell Sci.* 121:1046-1053. The presence of endogenous TERT protein in cells with little endogenous telomerase activity is consistent with the relative abundance of inactive splice variants of TERT in many cell types and extensive post-translational inhibitory regulation of TERT activity as previously reported by others. Yi et al. (2001) *Nucleic Acids Res.* 29:4818-4825; Cifuentes-Rojas and Shippen (2011) *Mutat Res.* [published online ahead of print: Oct. 18, 2011]; doi:10.1016/j.mrfmmm.2011.10.003. Treatment with increasing amounts of TERT mRNA resulted in a dose-dependent increase of TERT protein expression as measured in single cell assays by flow cytometry (FIG. 13C, right panel).

Telomerase activity is transiently increased. To test whether modified TERT mRNA delivery resulted in the generation of functional TERT protein, telomerase activity was quantified using a gel-based TRAP assay. Telomerase activity was detected in fibroblasts and myoblasts at all doses of TERT mRNA tested (0.25, 0.5, 1.0, and 2.0 μg/ml), and was not detected in untreated cells or cells treated with either vehicle only or modified mRNA encoding CI TERT, even at the highest dose of 2.0 μg/ml (FIG. 13D). Although TERT requires TERC to form a functional telomerase complex, delivery of TERT alone was sufficient to increase telomerase activity, consistent with previous findings that TERT is often limiting as TERC RNA copy number is high in many cell types lacking telomerase activity, including fibroblasts. Yi et al. (2001) *Nucleic Acids Res.* 29:4818-4825. A time course revealed that telomerase activity peaked at 24 hours and returned to baseline levels within 48 hours after a single transfection. This time frame is consistent with previously reported half-lives of human TERT mRNA (2-4 h), human β-globin mRNA (17-18 h: our exogenous TERT mRNA is flanked by β-globin 5' and 3' UTRs), and telomerase activity in cells exposed to an inhibitor of protein synthesis (cell type dependent, but typically >24 h). Kabnick and Housman (1988) *Mol Cell Biol.* 8:3244-3250; Holt et al. (1997) *Proc Natl Acad Sci USA.* 94:10687-10692; Xu et al. (1999) *Br J Cancer.* 80:1156-1161.

Figures 14A, 14B, 14C, 14D, 14E:
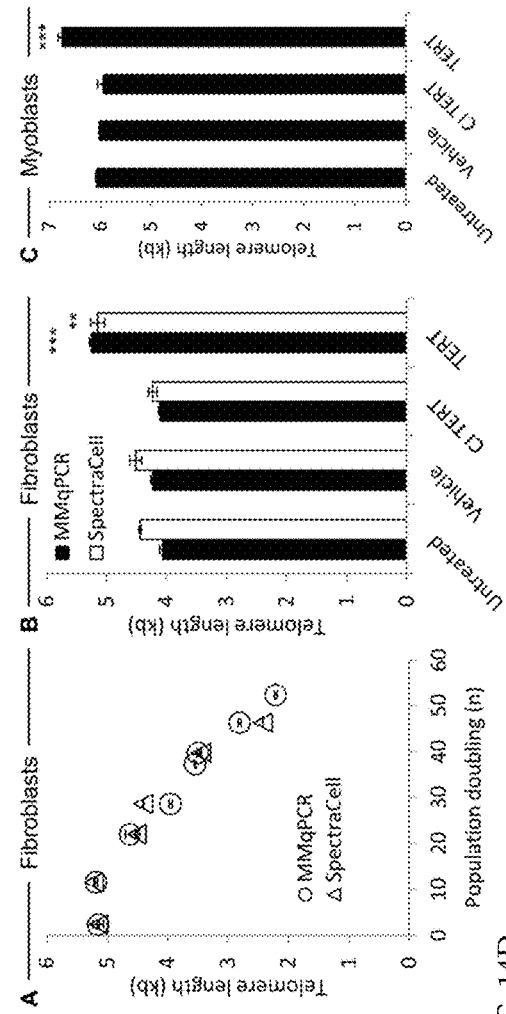
FIGS. 14A-14E. Increases in telomere length and proliferative capacity following modified TERT mRNA (modRNA) delivery.

Lengthening of telomeres. Telomere lengths in untreated fibroblasts declined over time (3 months) as expected (62) (FIG. 14A) and was quantified using two different methods. The monochrome multiplex qPCR method (MMqPCR) was used to assess length, and measurements were validated independently with a qPCR method performed by Spectra-Cell Laboratories, Inc. (correlation coefficient 0.97, P<0.001). Delivery of TERT mRNA three times in succession at 48-hour intervals to fibroblasts or myoblasts starting at population doubling (PD) 25 and 6, respectively, extended telomeres by 0.9±0.1 kb (22±3%), and 0.7±0.1 kb (12±2%), respectively (FIGS. 14B, 14C). Treatment with vehicle only or CI TERT mRNA had no significant effect on telomere length relative to untreated cells. The average rate of telomere extension in fibroblasts was 135±15 bp/PD.

Cell type-dependent increases in proliferative capacity. To test the effect of modified TERT mRNA delivery and consequent telomere extension on cell proliferative capacity, human fibroblasts were transfected either once, twice, or three times in succession. Treatments were delivered at 48-hour intervals. Untreated, vehicle only-treated, and CI TERT mRNA-treated fibroblasts exhibited an equivalent plateau in cell number after approximately 50-60 PD, whereas cells treated three times with TERT mRNA continued to proliferate for a finite additional 28±1.5 PD with an overall increase in cell number of $2.7 \times 10^8$ beyond untreated cells (FIG. 14D, left panel). The effect was dose-dependent with each additional treatment conferring additional PD (FIG. 14D, right panel). The incremental increase in proliferative capacity was greater with the first treatment than with the second or third treatments. Human myoblasts treated three times in succession every 48 hours gained 3.4±0.4 PD, equivalent to a 10-fold increase in cell number compared to untreated or vehicle treated controls (FIG. 14E). Such differences in PD between myoblasts and fibroblasts are not unexpected, as prior studies found similar limited effects of TERT overexpression to a few PD and showed that this limitation was due to a p16-mediated growth arrest in human myoblasts, in contrast to fibroblasts. Bodnar et al. (1998) *Science.* 279:349-352; Zhu et al. (2007) *Aging Cell.* 6:515-523. In both fibroblasts and myoblasts, vehicle only or CI TERT mRNA had no effect on proliferative capacity compared to untreated controls. These data show that delivery of modified TERT mRNA is an effective method for increasing PD in culture. Importantly, all of the treated cells studied exhibited a significant increase in cell numbers, but eventually reached a plateau in their growth curves, demonstrating absence of immortalization.

Figure 15A:
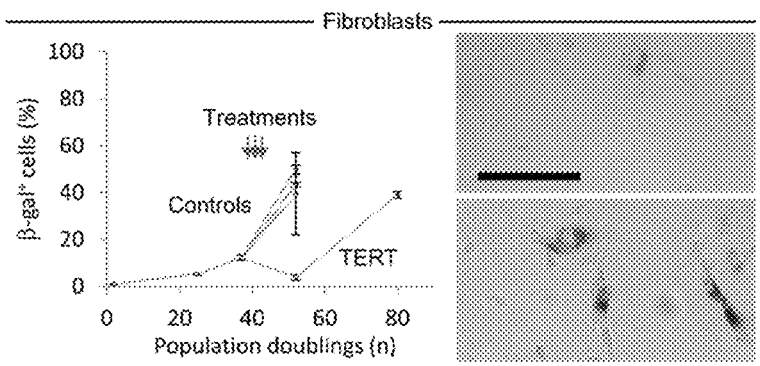
FIGS. 15A-15C. Transient reduction of senescence-associated markers following modified TERT mRNA delivery.
Figure 15B:
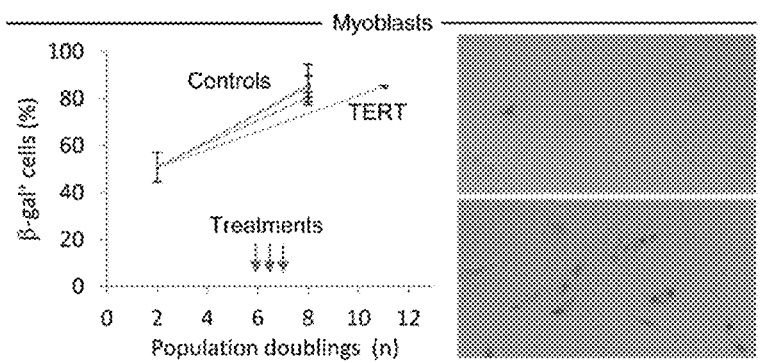
Figure 15C:
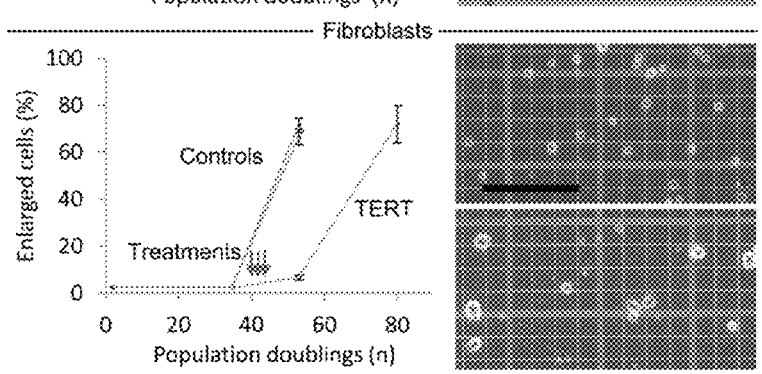
Figure 17:
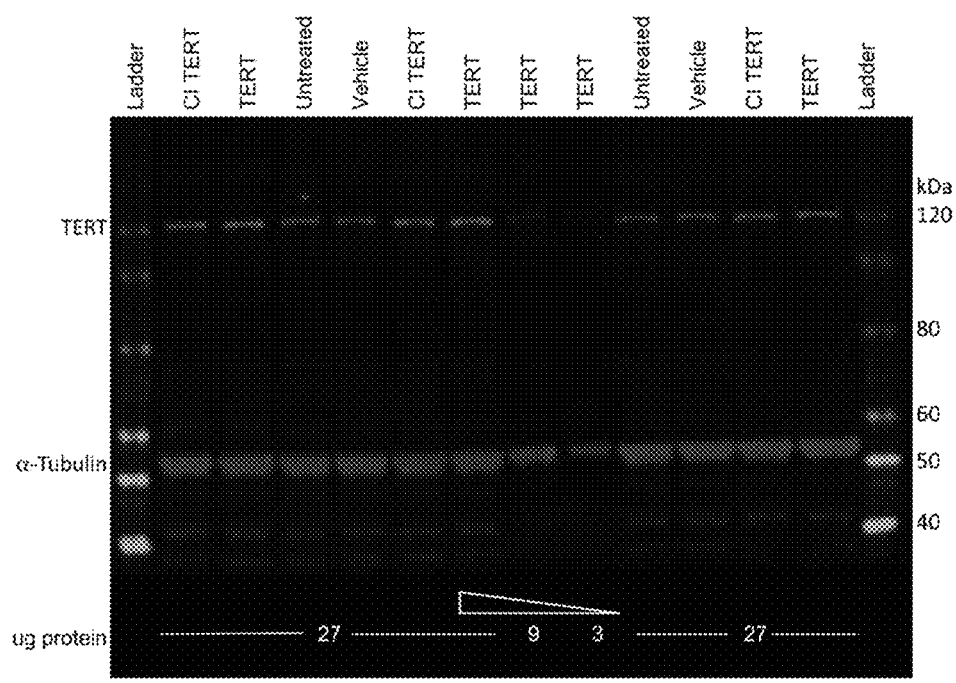
FIG. 17). Quantification of TERT protein levels 24 hours after transfection with 1 µg/ml of either TERT or CI TERT mRNA (n=3). Quantification of TERT protein in response to various doses of mRNA was measured at the single cell level by flow cytometry (n=10,000) (panel C, right). *P<0.05, **P<0.01 compared to untreated cells. Error bars represent s.e.m.

Transient reduction in markers of senescence. As the fibroblast populations stopped growing they exhibited markers of senescence including senescence-associated β-galactosidase (β-gal) staining and enlarged size (FIGS. 15A-15C). Cristofalo and Kritchevsky (1969) *Med Exp Int J Exp Med.* 19:313-320; Dimri et al. (1995) *Proc Natl Acad Sci U S A.* 92:9363-9367; Cristofalo et al. (2004) *Mech Ageing Dev.* 125:827-848; Lawless et al. (2010) *Exp Gerontol.* 45:772-778. These changes were transiently reduced in fibroblasts treated with TERT mRNA relative to untreated cells and cells receiving CI TERT mRNA or vehicle only. In accordance with findings by others, not all cells in the populations that had entered a growth plateau expressed β-galactosidase at detectable levels. Lawless et al. (2010) *Exp Gerontol.* 45:772-778; Binet et al. (2009) *Cancer Res.* 69:9183-9191. However, TERT mRNA-transfected fibroblasts and myoblasts expressed β-galactosidase to the same degree as the control cells of each type after the two populations reached a growth plateau. These data demonstrate that cells treated with TERT mRNA eventually and predictably cease division and express markers of senescence, and are therefore unlikely to be transformed.

This example demonstrates that transient delivery of TERT mRNA comprising modified nucleotides extends human telomeres and increases cell proliferative capacity without immortalizing the cells. The rate of telomere extension in fibroblasts observed here of 135±15 bp/PD is comparable to rates reported using viral methods, from 94 to >150 bp/PD (22, 69). Modified TERT mRNA extended telomeres in fibroblasts in a few days by 0.9±0.1 kb. Fibroblast telomere lengths have been reported to shorten over a human lifetime by approximately 1-2 kb on average. Allsopp et al. (1992) *Proc Natl Acad Sci USA.* 89:10114-10118. Thus, modified TERT mRNA is efficacious, yet transient and non-integrating, overcoming major limitations of constitutively expressed viral TERT mRNA delivery.

Human cells of greatest interest are often limited in number, including stem cells for use in experimentation or regenerative medicine. This problem is currently being addressed by various methods including somatic nuclear transfer, viral methods for gene delivery, and the use of culture conditions that lessen the rate of telomere shortening. Le et al. (2013) *Cell Stem Cell.* [published online ahead of print: Nov. 19, 2013]; doi:10.1016/j.stem.2013.11.005; Zimmermann and Martens (2008) *Cell Tissue Res.* 331:79-90; Mohsin et al. (2013) *Circ Res.* 113:1169-1179. The modified TERT mRNA treatment described here provides an advantageous complement or alternative to these methods that is brief, extends telomeres rapidly, and does not risk insertional mutagenesis. The brevity of TERT mRNA treatment is particularly attractive in that it can avert the loss of stem cell phenotype that can occur over time in culture (Gilbert et al. (2010) *Science.* 329:1078-1081) and shorten the post-reprogramming stage of iPSC generation during which telomeres extend (Wang et al. (2012) *Cell Res.* 22:757-768). Such a method of extending telomeres has the potential to increase the utility of diverse cell types for modeling diseases, screening for ameliorative drugs, and use in cell therapies.

A spectrum of effects on proliferative capacity was observed for the cell types tested, in agreement with previous studies demonstrating different effects of TERT overexpression on myoblast and fibroblast proliferative capacity. Bodnar et al. (1998) *Science.* 279:349-352; Zhu et al. (2007) *Aging Cell.* 6:515-523. Moreover, the amount of telomere extension did not correlate with proliferative capacity. Thus, cell context determines the efficacy of TERT expression on proliferative capacity and an understanding of the factors mediating this effect is of interest in overcoming this limitation. Factors that have been implicated in limiting myoblast proliferative capacity upon viral TERT overexpression include p16-mediated growth arrest, cell type and strain, and culture conditions. Zhu et al. (2007) *Aging Cell.* 6:515-523. More generally, the effect may be mediated by non-telomeric DNA damage, age, and mitochondrial integrity. Sahin et al. (2011) *Nature.* 470:359-365; Mourkioti et al. (2013) *Nat Cell Biol.* 15:895-904; Lopez-Otín et al. (2013) *Cell.* 153:1194-1217. The absence of an increase in telomere length or cell proliferative capacity in CI TERT mRNA-transfected cells is consistent with the treatment acting through the catalytic site of TERT by which nucleotides are added directly to telomeres. TERT mRNA-treated cell populations increased in number exponentially for a period of time and then eventually ceased expanding and exhibited markers of senescence to a similar degree as untreated populations, consistent with the absence of immortalization.

The transient non-integrating nature of modified mRNA and finite increase in proliferative capacity observed here render it safer than currently used viral or DNA vectors. Further, the method extends telomeres rapidly so that the treatment can be brief, after which the protective telomere shortening mechanism remains intact. This method can be used ex vivo to treat cell types that mediate certain conditions and diseases, such as hematopoietic stem cells or progenitors in cases of immunosenescence or bone marrow failure. In addition, modified mRNA may be delivered to certain tissues in vivo. Kormann et al. (2011) *Nat Biotechnol.* 29:154-157. In summary, the rapid and safe method for rapid extension of telomeres described here leads to delayed senescence and increased cell proliferative capacity without immortalizing human cells.

METHODS mRNA template generation and synthesis. To generate modified mRNA encoding GFP, TERT, and CI TERT, their respective open reading frames (ORFs) were inserted into the MCS of a starting plasmid containing the T7 promoter, the 5' UTR of human b-globin (HBB), the MCS, the 3' UTR of HBB, a 151 bp poly-A sequence, and a restriction site for linearization with a class II enzyme following the poly-A sequence. The resulting intermediate plasmids were sequenced, linearized, and transcribed using the buffer and RNA polymerase from the MEGAscript T7 Kit (Ambion, Austin, Texas, USA), and a custom mix of canonical and non-canonical nucleotides (TriLink BioTechnologies, San Diego, CA, USA) in which the final nucleotide concentrations per 40 µl IVT reaction were 7.5 mM for each of adenosine-5'-triphosphate (ATP), 5-methylcytidine-5'-triphosphate (m5C), and pseudouridine-5'-triphosphate ($\Psi$), 1.5 mM for guanosine-5'-triphosphate (GTP), and 6 mM for the cap analog (ARCA) (New England Biolabs, Ipswitch, MA, USA), or a molar ratio of ATP:m5C:$\Psi$:GTP:ARCA of 1:1:1:0.2:0.8. To further decrease potential immunogenicity of the mRNA related to the 5'-3P-bearing fraction, the IVT products were treated with Antarctic Phosphatase (New England Biolabs). The size and integrity of the mRNA products were verified using denaturing agarose gel electrophoresis. The wild type human TERT ORF used to generate the DNA templates for mRNA synthesis is identical to the NCBI human TERT transcript variant 1 (reference sequence NM_198253.2). The ORF was generated from the pBABE-neo-hTERT plasmid (Counter et al. (1998) *Proc Natl Acad Sci USA.* 95:14723-14728) (plasmid 1774, Addgene, Cambridge, MA, USA). The pBABE-neo-hTERT plasmid had a non-silent mutation at residue 516 in the QFP motif of TERT, a motif associated with multimerization and TERT interaction with TERC RNA, and thus to avoid the possibility of artifacts due to this mutation we made the sequence identical to the NCBI reference sequence by correcting the mutation with the change G516D. The CI TERT mutant was generated from the TERT sequence by introducing the mutation D712A.

Cell culture and treatment. Human primary fetal lung MRC5 fibroblasts were obtained from ATCC (Manassas, VA, USA) at passage 14. ATCC does not indicate the PD number, thus, our PD values cited herein refer to the number of PD after receipt of cells from ATCC. MRC5 cells were cultured in DMEM with 20% FBS and penicillin-streptomycin. Human 30 year-old primary skeletal muscle myoblasts (Lonza, Allendale, NJ, USA) were cultured in SkGM-2 media (Lonza) according to the vendor's instructions. Population doublings were calculated as the base 2 log of the ratio between cells harvested and cells plated at the previous passaging, and were considered to be zero if fewer cells were harvested than plated. Cells were transfected with modified TERT mRNA using Lipofectamine RNAiMax (Life Technologies, Grand Island, NY, USA) prepared in OptiMEM Reduced Serum Media (Life Technologies, Grand Island, NY, USA) and added to the cells in a 1:5 v:v ratio with their normal media to achieve the final concentrations indicated herein.

Telomerase activity measurement. Twenty-four hours after the start of the transfection period, cells were harvested and lysed in CHAPS buffer. The TRAP assay was performed using a modified version of the TRAPeze kit (EMD Millipore, Billerica, MA, USA), in which the primers and polymerase were added after, rather than before, the step during which the artificial telomere substrate is extended. The PCR program was 94° C. 30 s/59° C. 30 s/72° C. 45 s for 30 cycles, and the products were run on a 15% polyacrylamide gel in 0.5×TBE stained with SYBR Gold Nucleic Acid Gel Stain (Life Technologies, Grand Island, NY, USA). The time course of telomerase activity was performed using the TRAPeze RT kit (EMD Millipore, Billerica, MA, USA).

Western blot. Protein was harvested by washing cells once with PBS and then lysing cells in RIPA buffer (Cell Signaling Technology, Danvers MA, USA). Protein was run on NuPAGE Novex Tris-Acetate Gels (Life Technologies, Grand Island, NY, USA), transferred to PVDF membrane for 2 h at 35V, then hybridized to anti-α tubulin (Sigma, St. Louis, MO, USA) at 1:10,000 and anti-TERT antibody (ABCAM, Cambridge, MA, USA, 32020 at 1:1000; or Rockland Immunochemicals, Gilbertsville, PA, USA, 600-401-252S at 1:500) and incubated overnight at 4° C. Detection was performed using infrared (680 nm and 800 nm) antibodies (LI-COR, Lincoln, NE, USA) and the Odyssey imager (LI-COR). Total intensity of each band was quantified using ImageJ (NIH, Bethesda, MD, USA). The intensity of each TERT band was normalized by its corresponding a tubulin band.

Flow cytometry. Cells were harvested 24 h after transfection with the indicated doses (FIGS. 16A-16C) of TERT mRNA and stained with anti-TERT antibody (Rockland Immunochemicals, Gilbertsville, PA, USA; 600-401-252S) at 1:500.

Telomere length measurement by SpectraCell Laboratories, Inc. Genomic DNA was extracted using phenol chloroform and quantified using the Quant-iT™ PicoGreen® dsDNA Assay Kit (Life Technologies, Grand Island, NY, USA). Telomere length analysis was performed at Spectra-Cell Laboratories Inc. (Houston, TX, USA) using a CLIA approved, high throughput qPCR assay, essentially as described by Cawthon et al. Cawthon (2002) *Nucleic Acids Res.* 30(10):e47; Cawthon (2009) *Nucleic Acids Res.* 37(3): e21. The assay determines a relative telomere length by measuring the factor by which the sample differs from a reference DNA sample in its ratio of telomere repeat copy number to singe gene (36B4) copy number. This ratio (T/S ratio) is thought to be proportional to the average telomere length. All samples were run in at least duplicate with at least one negative control and two positive controls of two different known telomere lengths (high and low) and an average variance of up to 8% was seen. The results were reported as a telomere score equivalent to the average telomere length in kb.

Telomere length measurement by MMqPCR. Telomere length was measured using a modified version of the MMqPCR protocol developed by Cawthon (Cawthon (2009) *Nucleic Acids Res.* 37(3):e21) with the following changes: Additional PCR pre-amplification cycles were added to make the telomere product amplify earlier, widening the gap between telomere and single-copy gene signals; a mixture of two Taq polymerases was experimentally determined to result in better PCR reaction efficiencies than each on its own; reducing the SYBR Green concentration from 0.75× to 0.5× resulted in earlier signal. Genomic DNA was harvested from cells using the PureGene kit (Qiagen Germantown, MD, USA) with RNase digestion, quantified using a NanoDrop 2000 (ThermoFisher Scientific, Waltham, MA, USA), and 10-40 ng was used per 15 µl qPCR reaction performed in quadruplicate using a LightCycler 480 PCR System (Roche, Basel, Switzerland). A serial dilution of reference DNA spanning five points from 100 ng/µl to 1.23 ng/µl was included in each assay to generate a standard curve required for sample DNA quantification. The final concentrations of reagents in each 15 µl PCR reaction were: 20 mM Tris-HCl pH 8.4, 50 mM KCl, 3 mM MgCl2, 0.2 mM each dNTP, 1 mM DTT, 1 M betaine (Affymetrix, Santa Clara, CA, USA), 0.5×SYBR Green I (Life Technologies, Grand Island, NY, USA), 0.1875U Platinum Taq (Life Technologies, Grand Island, NY, USA), 0.0625×Titanium Taq (Clontech), and 900 nM each primer (telg, telc, hbgu, and hbgd primer sequences specified in Cawthon (2009) *Nucleic Acids Res.* 37(3):e21. The thermal cycling program was: 2 minutes at 95° C.; followed by 6 cycles of 15 s at 95° C., 15 s at 49° C.; followed by 40 cycles of 15 s at 95° C., 10 s at 62° C., 15 s at 72° C. with signal acquisition, 15 s at 84° C., and 10 s at 88° C. with signal acquisition. The Roche LightCycler 480 software was used to generate standard curves and calculate the DNA concentrations of telomere and single-copy genes for each sample. T/S ratios were calculated for each sample replicate, and the result averaged to yield the sample T/S ratio which was calibrated using blinded replicate samples of reference cells sent to Spectra-Cell as described above. The independently obtained relative values of T/S ratios measured using MMqPCR and by SpectraCell for the same samples were highly consistent (correlation coefficient=0.97, P<0.001).

Reverse transcription qPCR. Primers were designed using Primer3 (Untergasser et al. (2012) *Nucleic Acids Res.* 40:e115) and are listed in Table 9 except where otherwise noted. Twenty-four hours after start of treatment, cells were washed three times with PBS before harvesting in Buffer RLT (Qiagen, Germantown, MD, USA). RNA was converted to cDNA using High Capacity RNA-to-cDNA Master Mix (Life Technologies, Grand Island, NY, USA). Endogenous TERT mRNA was amplified using a forward primer in the open reading frame of TERT and a reverse primer in the 3' UTR of endogenous TERT mRNA. Exogenous TERT mRNA was amplified using a forward primer in the open reading frame of TERT mRNA and a reverse primer in the 3' UTR of HBB present in our exogenous TERT and CI TERT mRNA, but not in endogenous TERT mRNA. Relative levels were calculated using the Pfaffl method. Reference genes were RPL37A (using primers specified in Greber et al. (2011) *EMBO J.* 30:4874-4884) and GAPDH, neither of which exhibited a significant change in Ct value in control or treated cells.

TABLE 9

Primer sequences.

| Target | Forward primer (5'-3') | Reverse primer (5'-3') | Product length (bp) |
|---|---|---|---|
| Exogenous TERT | hTERT (NM_198253.2) GTCACCTACGTGCCACTCCT (SEQ ID NO: 5) | 3' UTR of HBB AGCAAGAAAGCGAGCCAAT (SEQ ID NO: 6) | 162 |

TABLE 9-continued

Primer sequences.

| Target | Forward primer (5'-3') | Reverse primer (5'-3') | Product length (bp) |
|---|---|---|---|
| Endogenous TERT | hTERT (NM_198253.2) GCCCTCAGACTTCAAGACCA (SEQ ID NO: 7) | 3' UTR of hTERT (NM_198253.2) GCTGCTGGTGTCTGCTCTC (SEQ ID NO: 8) | 74 |
| GAPDH | CAATGACCCCTTCATTGACC (SEQ ID NO: 9) | TTGATTTTGGAGGGATCTCG (SEQ ID NO: 10) | 159 |

Senescence-associated β-galactosidase staining and cell size scoring. β-gal staining was performed using the Senescence β-Galactosidase Staining Kit (Cell Signaling Technology, Danvers MA, USA). At least 50 cells per population were scored in duplicate. Cell diameter was scored manually after trypsinization on a hemocytometer grid. Cristofalo and Kritchev sky (1969) *Med Exp Int J Exp Med.* 19:313-320.

Statistics. Student's T-tests and Pearson correlation coefficient calculations were performed using Microsoft Excel. Error bars represent the mean±s.e.m.

Example 4

Delivery of TERT ModRNA to Cells by Electroporation

Figure 18:
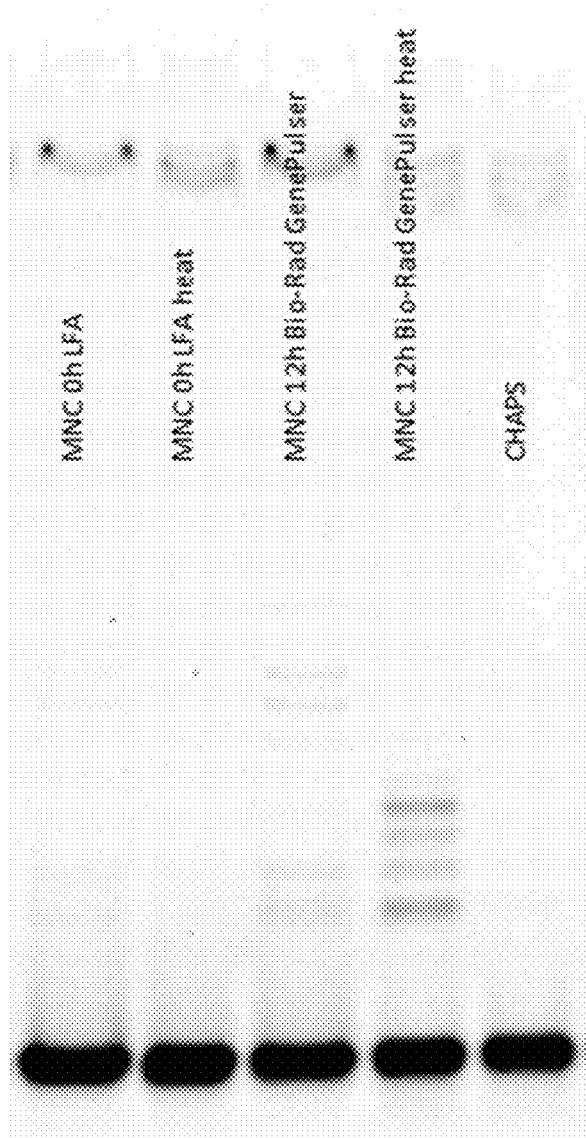
FIG. 18. TRAP gel showing increased telomerase activity in mononuclear cells electroporated with TERT modRNA at a setting of 200 V, 25 uF, 1000 Ohm, in a 1 mm cuvette with 10 ul of cell suspension and TERT modRNA. The heat treated sample lane contains a primer dimer artifact of the method as indicated by the strong band at the fourth rung of the ladder.
Figure 19:
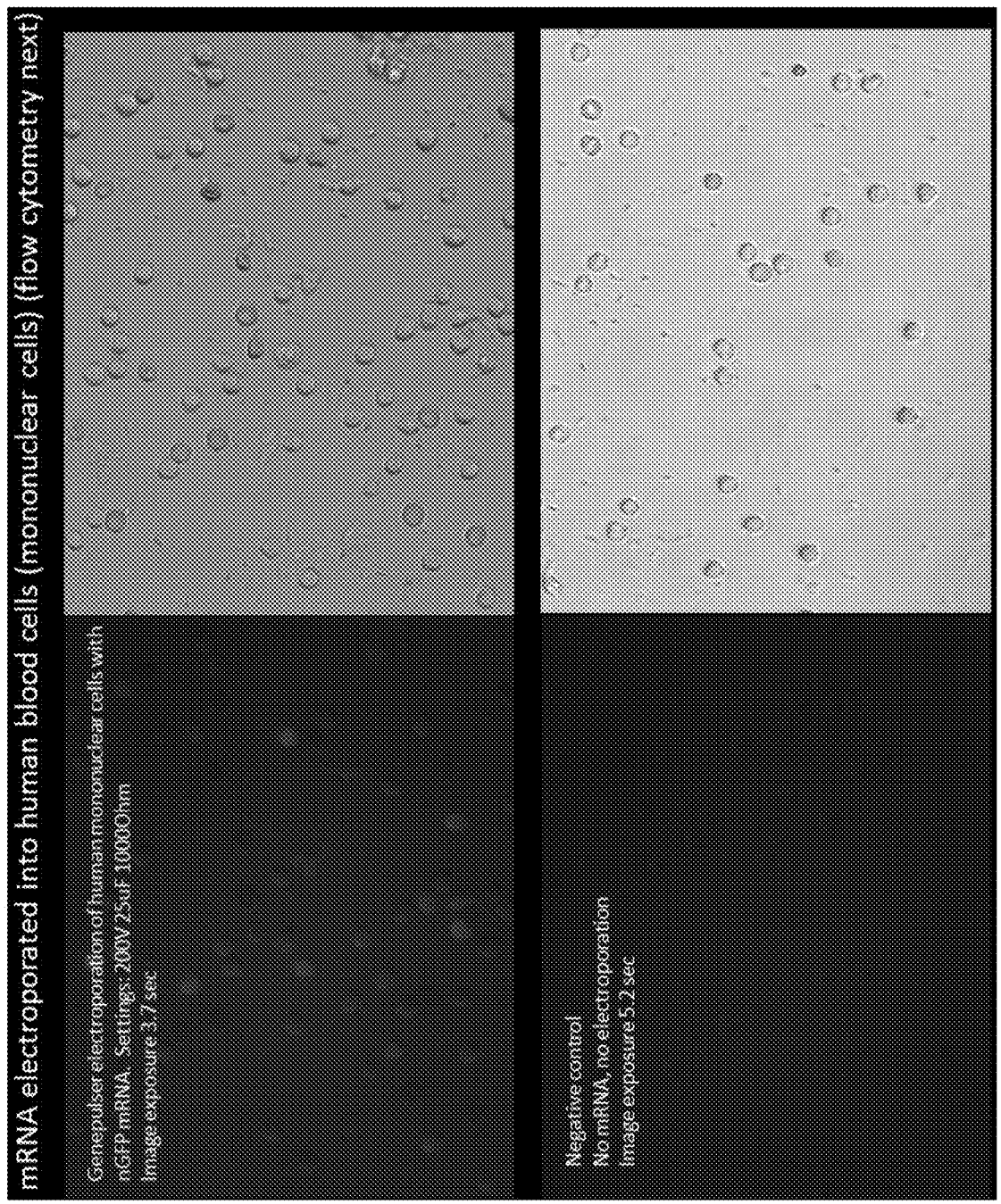
FIG. 19. Microscope images of mononuclear cells fluorescing after electroporation with modRNA encoding GFP.
Figure 21:
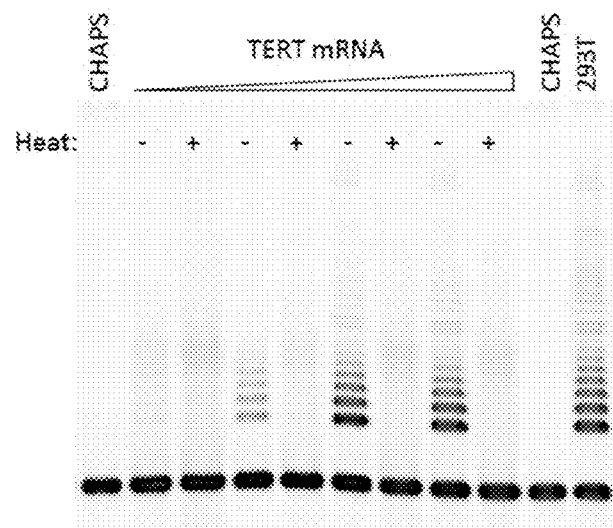
FIG. 21. Image of gel from TRAP assay showing increasing telomerase activity in fibroblasts electroporated with increasing doses of TERT modRNA.

The TERT modRNA compounds of the invention may also be delivered to cells by electroporation, as illustrated in FIGS. 18-20, using electroporation parameters, including the concentration of TERT modRNA, voltage wave form, and electrode geometry appropriate for achieving optimal transfection efficiency and viability in a given cell type. FIG. 21 shows the dependence of telomerase activity of the dose of TERT modRNA delivered by electroporation.

Example 5

Delivery of a ModRNA to Human Blood Cells

Figure 22:
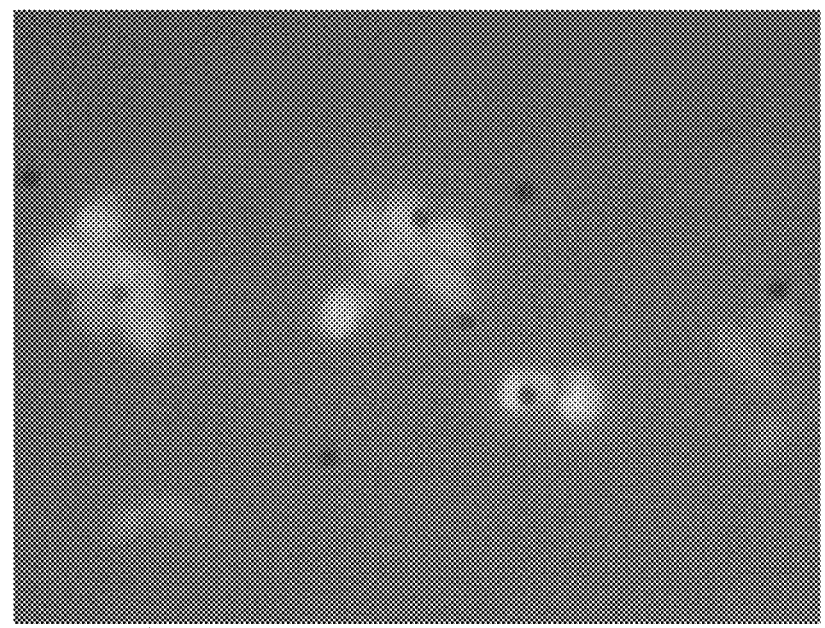
FIG. 22. Fluorescent micrographs showing that CD8+ T-cells activated with CD3/CD28 and electroporated with GFP modRNA express GFP activity. Dark dots are CD3/CD28-coated beads.

CD8+ T-cells were transfected with modRNA as follows. The buffy layer from whole human blood centrifuged on Lymphoprep (Axis-Shield) density gradient medium to obtain mononuclear cells which were washed twice and then depleted of non-CD8+ leukocytes using the Dynabeads Untouched Human CD8 T Cells Kit (Life Technologies). The CD8+ cells were stimulated using Dynabeads Human T-Activator CD3.CD28 (Life Technologies) and cultured for 4 days using OpTimizer T-Cell media supplemented with 30,000 U/ml IL-2. The T-cells were then transfected with modRNA encoding nuclear GFP and TERT at a concentration of 50 µg/ml in a volume of 20 µl Nucleofector P3 solution containing Supplement 1. Cells were assayed for fluorescence and viability 24 hours after transfection. Results of the transfection are shown in FIG. 22. The bright fluorescence demonstrates high copy number, with transfection efficiency over 90% with high viability.

Example 6

Expression of Telomerase in Human Keratinocytes Using a Telomerase ModRNA

Figure 23:
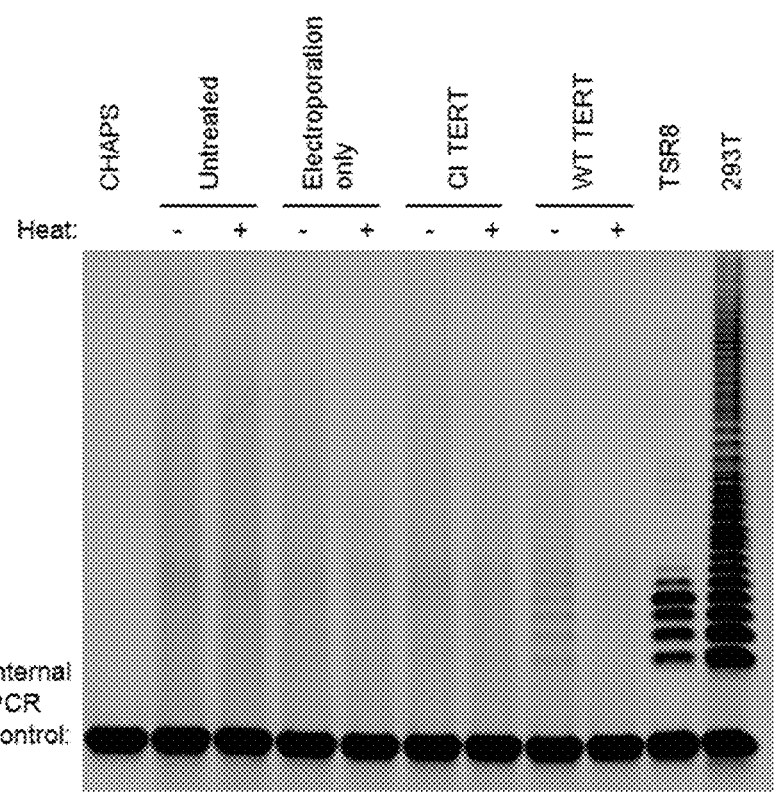
FIG. 23. Electroporation of human keratinocytes with TERT modRNA results in expression of telomerase activity.

As shown in FIG. 23, electroporation of human keratinocytes with TERT modRNA results in the expression of telomerase activity in the cells. Human primary keratinocytes (Lonza) were suspended at a density of $3 \times 10^7$ cells/ml in OptiMEM media (Life Technologies) containing 50 µg/ml of modRNA encoding either catalytically inactive (CI) TERT or wild type TERT. 10 µl of the cell suspension was placed in a 1 mm gap cuvette and electroporated using a Gene Pulser (BioRad) using 200 V, 1000 Ohms, and 25 microfarads. The cells were immediately returned to KGM-2 media (Lonza) and incubated for 24 hours before being harvested for measurement of telomerase activity using the gel-based TRAPeze assay (Millipore). Each 25 µl TRAP reaction was performed using 1 µg of total protein, with duplicate samples heated at 85° C. for 10 minutes to inactivate telomerase. Untreated, electroporation only, and CI TERT samples served as negative controls, and 293T cells and TSR8 served as positive controls.

Example 6

Figure 24:
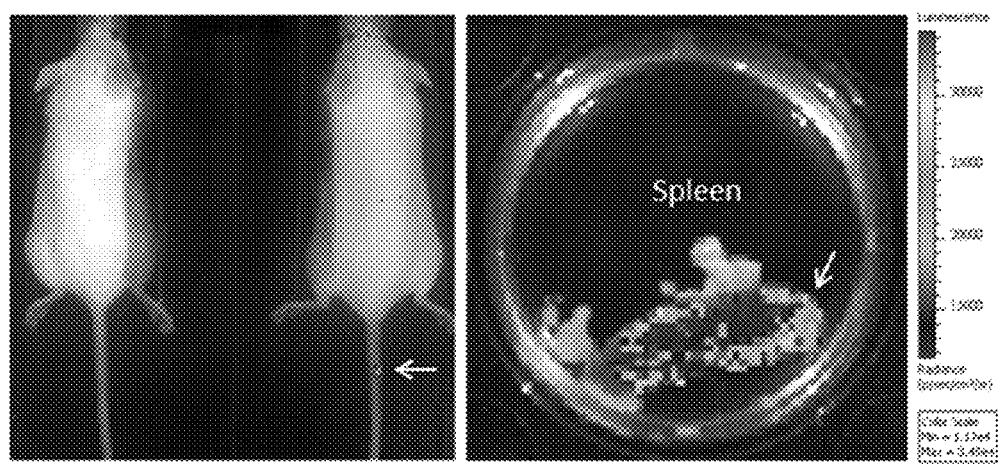
FIG. 24. Expression of a luciferase modRNA after in vivo delivery to a rodent.

Expression of a ModRNA-Encoded Protein by Delivery in Vivo modRNA delivered in vivo can result in the expression of a functional protein encoded by the modRNA. Kormann et al. (2012) *Nature Biotechnology* 29:154-157; Kariko et al. (2012) *Molecular Therapy* 20:948-93. This has been confirmed here by complexing 2 µg of modRNA encoding luciferase with a cationic lipid vehicle (TransIT) and injecting intravenously in 50 µl of OptiMEM (Life Technologies) in a rodent tail. The spleen was harvested and treated with luciferin and assayed for luciferase activity using an IVIS bioluminescence imager (Perkin-Elmer). As shown in FIG. 24, luciferase activity was detected at the injection site and in the spleen (arrows).

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

What is claimed is:

1. A method of treating an animal subject, comprising:
   administering a compound to the animal subject,
   wherein the compound comprises a synthetic ribonucleic acid comprising at least one modified nucleoside and coding for a telomerase reverse transcriptase,
   wherein the animal subject suffers from or is at risk of a disease resulting from shortened telomeres; and
   wherein at least one telomere is extended within a cell in the animal subject.

2. The method of claim 1, wherein the disease is selected from the group consisting of metabolic syndrome, diabetes, diabetic ulcers, heart disease, cancer, vascular dementia, Alzheimer's disease, stroke, age-related macular degeneration, immunosenescence, bone marrow failure, gastrointestinal ulcers, cirrhosis, hernia, infection, chronic infection, mild or severe cognitive impairment, impaired mobility, osteoporosis, osteoarthritis, rheumatoid arthritis, age-related anxiety, balance disorders, tinnitus, Bell's palsy, cataracts, chronic obstructive pulmonary disease, corneal abrasion, coronary artery disease, peripheral artery disease, conjunctivitis, chalazion, dehydration, depression, emphysema, eye disease, failure to thrive, flu, generalized anxiety disorder, glaucoma, hearing loss, loss of sense of taste, loss of appetite, hip dislocation, memory loss, Parkinson's disease, spinal stenosis, urinary incontinence, and vertebral fracture.

3. The method of claim 1, wherein the animal subject suffers from or is at risk of an age-related illness, an age-related condition, or an age-related decline in function or appearance.

4. The method of claim 1, further comprising the step of:
   measuring telomere length of a cell in or from the subject animal and administering the compound if a shortened telomere length is detected.

5. The method of claim 4, wherein the measuring and administering steps are repeated at least once.

6. The method of claim 1, wherein the at least one telomere is transiently extended within the cell of the subject animal.

7. The method of claim 1, comprising:
   administering a composition to the animal subject;
   wherein the composition comprises the compound of claim 1; and
   a telomerase RNA component, a delivery vehicle, or both a telomerase RNA component and a delivery vehicle.

8. The method of claim 7, wherein the telomerase RNA component is a mammalian, avian, reptilian, or fish telomerase RNA component.

9. The method of claim 8, wherein the telomerase RNA component is a human telomerase RNA component.

10. The method of claim 7, wherein the delivery vehicle is an exosome, a lipid nanoparticle, a polymeric nanoparticle, a natural or artificial lipoprotein particle, a cationic lipid, a protein, a protein-nucleic acid complex, a liposome, a virosome, or a polymer.

11. The method of claim 10, wherein the delivery vehicle is a cationic lipid.

12. The method of claim 11, wherein the delivery vehicle is non-immunogenic.

13. The method of claim 1, wherein the telomerase reverse transcriptase is a mammalian, avian, reptilian, or fish telomerase reverse transcriptase or a variant that retains telomerase catalytic activity.

14. The method of claim 13, wherein the telomerase reverse transcriptase is a human telomerase reverse transcriptase.

15. The method of claim 1, wherein the ribonucleic acid comprises a 5' cap, a 5' untranslated region, a 3' untranslated region, and a poly-A tail.

16. The method of claim 15, wherein the 5' cap is non-immunogenic.

17. The method of claim 15, wherein the 5' cap has been treated with phosphatase.

18. The method of claim 15, wherein the poly-A tail increases stability of the ribonucleic acid.

19. The method of claim 15, wherein the 5' untranslated region or the 3' untranslated region comprise a sequence from a stable mRNA or an mRNA that is efficiently translated.

20. The method of claim 15, wherein the 5' untranslated region and the 3' untranslated region both comprise a sequence from a stable mRNA or an mRNA that is efficiently translated.

21. The method of claim 15, wherein the 5' cap, the 5' untranslated region, or the 3' untranslated region stabilizes the ribonucleic acid, increases the rate of translation of the ribonucleic acid, or modulates the immunogenicity of the ribonucleic acid.

22. The method of claim 1, wherein the at least one modified nucleoside modulates immunogenicity of the ribonucleic acid.

23. The method of claim 1, wherein the synthetic ribonucleic acid is a purified synthetic ribonucleic acid.

24. The method of claim 23, wherein the synthetic ribonucleic acid is purified to remove immunogenic components.

25. The method of claim 1, wherein the ribonucleic acid codes for a human, cat, dog, mouse, horse, cow, sheep, pig, African elephant, chicken, rat, zebrafish, Japanese medaka, or chimpanzee telomerase reverse transcriptase, or a polypeptide with at least 95% sequence identity to the telomerase reverse transcriptase.

26. The method of claim 25, wherein the ribonucleic acid codes for a human telomerase reverse transcriptase, or a polypeptide with at least 95% sequence identity to the human telomerase reverse transcriptase.

27. The method of claim 1, wherein the animal subject is a mammal.

28. The method of claim 27, wherein the animal subject is a human.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: PCR Primer

<400> SEQUENCE: 1
gccctcagac ttcaagacca 20

<210> SEQ ID NO 2
<211> LENGTH: 20
<212> TYPE: DNA
<213> ORGANISM: Artificial Sequence
<220> FEATURE:
<223> OTHER INFORMATION: PCR Primer

<400> SEQUENCE: 2
aggcagaatc cagatgctca 20

<210> SEQ ID NO 3
<211> LENGTH: 20
<212> TYPE: DNA
<213> ORGANISM: Artificial Sequence
<220> FEATURE:
<223> OTHER INFORMATION: PCR Primer

<400> SEQUENCE: 3
gtggacctga cctgccgtct 20

<210> SEQ ID NO 4
<211> LENGTH: 20
<212> TYPE: DNA
<213> ORGANISM: Artificial Sequence
<220> FEATURE:
<223> OTHER INFORMATION: PCR Primer

<400> SEQUENCE: 4
ggaggagtgg gtgtcgctgt 20

<210> SEQ ID NO 5
<211> LENGTH: 20
<212> TYPE: DNA
<213> ORGANISM: Artificial Sequence
<220> FEATURE:
<223> OTHER INFORMATION: PCR Primer

<400> SEQUENCE: 5
gtcacctacg tgccactcct 20

<210> SEQ ID NO 6
<211> LENGTH: 19
<212> TYPE: DNA
<213> ORGANISM: Artificial Sequence
<220> FEATURE:
<223> OTHER INFORMATION: PCR Primer

<400> SEQUENCE: 6
agcaagaaag cgagccaat 19

<210> SEQ ID NO 7
<211> LENGTH: 20
<212> TYPE: DNA
<213> ORGANISM: Artificial Sequence

```
<220> FEATURE:
<223> OTHER INFORMATION: PCR Primer

<400> SEQUENCE: 7
gccctcagac ttcaagacca                                            20

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
gctgctggtg tctgctctc                                             19

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
caatgacccc ttcattgacc                                            20

<210> SEQ ID NO 10
<211> LENGTH: 20
<212> TYPE: DNA
<213> ORGANISM: Artificial
<220> FEATURE:
<223> OTHER INFORMATION: PCR Primer

<400> SEQUENCE: 10
ttgattttgg agggatctcg                                            20
```